US012378286B2

(12) United States Patent
Levy et al.

(10) Patent No.: US 12,378,286 B2
(45) Date of Patent: Aug. 5, 2025

(54) METHODS AND COMPOSITIONS USEFUL FOR INHIBITING GROWTH OF CERTAIN BACTERIA

(71) Applicants: The Regents of the University of California, Oakland, CA (US); ETH-Zurich, Zurich (CH); Virginia Tech Intellectual Properties, Inc., Blacksburg, VA (US); The University of North Carolina at Chapel Hill, Chapel Hill, NC (US)

(72) Inventors: Asaf Levy, Concord, CA (US); Maximilian Mittelviefhaus, Zurich (CH); Jiamin Miao, Lanzhou (CN); Kunru Wang, Blacksburg, VA (US); Bingyu Zhao, Blacksburg, VA (US); Julia Vorholt-Zambelli, Zurich (CH); Jeffrey L. Dangl, Chapel Hill, NC (US)

(73) Assignees: The Regents of the University of California, Oakland, CA (US); ETH-Zurich, Zürich (CH); Virginia Tech Intellectual Properties, Inc., Blacksburg, VA (US); The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/866,308

(22) Filed: May 4, 2020

(65) Prior Publication Data

US 2021/0101931 A1 Apr. 8, 2021

Related U.S. Application Data

(63) Continuation of application No. PCT/US2018/059277, filed on Nov. 5, 2018.

(60) Provisional application No. 62/581,556, filed on Nov. 3, 2017.

(51) Int. Cl.

| | |
|---|---|
| ***C07K 14/195*** | (2006.01) |
| ***A01N 63/20*** | (2020.01) |
| ***C07K 7/06*** | (2006.01) |
| ***C07K 7/08*** | (2006.01) |
| *A61K 38/00* | (2006.01) |

(52) U.S. Cl.

CPC ................ *C07K 7/06* (2013.01); *A01N 63/20* (2020.01); *C07K 7/08* (2013.01); *C07K 14/195* (2013.01); *A61K 38/00* (2013.01)

(58) Field of Classification Search

None

See application file for complete search history.

(56) References Cited

U.S. PATENT DOCUMENTS 7,723,468 B2 * 5/2010 Daffre ...................... C07K 7/64 530/300

OTHER PUBLICATIONS

Johnson et al. ('Efficacy of a nonpathogenic Acidovorax citrulli strain as a biocontrol seed treatment for bacterial fruit blotch of cucurbits' Plant Disease Jun. 2011 pp. 697-704) (Year: 2011).*
Microbiology Society website (retrieved from https://microbiologysociety.org/why-microbiology-matters/what-is-microbiology/microbes-and-the-human-body/microbes-and-disease.html on Nov. 18, 2021, 3 pages) (Year: 2021).*
Levy et al. ('Genomic features of bacterial adaptation to plants' Nature Genetics January v50 2018 pp. 138-150) (Year: 2018).*
Panchenko et al. ('Prediction of functional sites by analysis of sequence and structure conservation' Protein Science 2004 v13 pp. 884-892) (Year: 2004).*
Agler et al., "Microbial hub taxa link host and abiotic factors to plant microbiome variation." PLOS Biol. 14:e1002352 (2016).
Alexeyev, "The pKNOCK series of broad-host-range mobilizable suicide vectors for gene knockout and targeted DNA insertion into the chromosome of gram-negative bacteria." Biotechniques. 26828:824-828 (1999).
Bai et al., "Functional overlap of the *Arabidopsis* leaf and root microbiota." Nature. 528:364-369 (2015).
Basler et al., "Tit-for-Tat: Type VI Secretion System Counterattack during Bacterial Cell-Cell Interactions.", Cell. 152:884-894 (2013).
Baumann, "Biology of bacteriocyte-associated endosymbionts of plant sap-sucking insects.", Annu Rev Microbiol.; 59:155-189 (2005).
Benjamini et al., "Controlling the false discovery rate: A practical and powerful approach to multiple testing." J R Stat Soc Ser B.; 57(1) 289-300 (1995).
Beszteri et al., "Average genome size: a potential source of bias in comparative metagenomics." ISME J., 4:1075-1077 (2010).
Bokulich et al., "Microbial biogeography of wine grapes is conditioned by cultivar, vintage, and climate.", Proc Natl Acad Sci U S A.; 111:E139-E148 (2014).
Brynildsrud et al., "Rapid scoring of genes in microbial pan-genome-wide association studies with Scoary." Genome Biol.; 17:238, 9 pages (2016).
Buchfink et al., "Fast and sensitive protein alignment using Diamond." Nat Methods.; 12:59-60 (2014).

(Continued)

*Primary Examiner* — Ronald T Niebauer
(74) *Attorney, Agent, or Firm* — Robin C. Chiang; LAWRENCE BERKELEY NATIONAL LABORATORY

(57) ABSTRACT

The present invention provides for a composition comprising a purified or isolated Hyde1 gene product, or a functional fragment thereof; a modified host cell capable of expressing a Type VI secretion system (T6SS), Hyde1, and/or Hyde2, or a functional fragment thereof; a method of treating a disease caused all or in part by a bacterial cell, comprising administering a composition of the present invention to a subject in need thereof; and a method to limit or reduce growth of a pathogenic bacteria in an environment, comprising: introducing a non-pathogenic bacterial capable of expressing a Type VI secretion system (T6SS), Hyde1, and/or Hyde2, or functional fragment thereof, to an environment.

1 Claim, 23 Drawing Sheets

Specification includes a Sequence Listing.

(56) References Cited

OTHER PUBLICATIONS

Bulgarelli et al., "Revealing structure and assembly cues for *Arabidopsis* root-inhabiting bacterial microbiota." Nature, 488:91-95 (2012).
Burstein et al., "Genome-scale identification of Legionella pneumophila effectors using a machine learning approach." PLoS Pathog., 5:e1000508, (2009), 12 pages.
Büttner et al., "Type III protein secretion in plant pathogenic bacteria." Plant Physiol., 150:1656-1664 (2009).
Cesari et al., "A novel conserved mechanism for plant NLR protein pairs: the 'integrated decoy' hypothesis." Frontiers in Plant Sci., 5, (2014), 10 pages.
Chowdhury et al., "Biocontrol mechanism by root-associated Bacillus amyloliquefaciens FZB42—a review." Front Microbiol. 6:780 (2015), 11 pages.
Cole et al., "Genome-wide identification of bacterial plant colonization genes." PLOS Biol. 15:e2002860 (2017), 24 pages.
Coleman-Derr et al., "Plant compartment and biogeography affect microbiome composition in cultivated and native *Agave* species." New Phytol. 209:798-811 (2016).
Coutinho et al., "Plant-Influenced Gene Expression in the Rice Endophyte *Burkholderia kururiensis* M130." Mol Plant-Microbe Interact. 28:10-21 (2015).
De Jonge et al., "Conserved fungal LysM efector Ecp6 prevents chitin-triggered immunity in plants." Science, 329: 953-955 (2010).
De Weert S et al., "Flagella-Driven Chemotaxis Towards Exudate Components Is an Important Trait for Tomato Root Colonization by Pseudomonas fluorescens." Molecular Plant-Microbe Interactions, 15:1173-1180 (2002).
De Weger et al., "Flagella of a plant-growth-stimulating Pseudomonas fluorescens strain are required for colonization of potato roots." J Bacteriol. 169: 2769-2773 (1987).
Dean, "Functional domains and motifs of bacterial type III effector proteins and their roles in infection.", FEMS Microbiol Rev 35: 1100-1125 (2011).
Doty et al., "Diazotrophic endophytes of native black cottonwood and willow." Symbiosis. 47:23-33 (2009).
Edgar, "Search and clustering orders of magnitude faster than Blast." Bioinformatics. 26:2460-2461 (2010).
Edwards et al., "Structure, variation, and assembly of the root-associated microbiomes of rice.", Proc Natl Acad Sci. 112:E911-E920 (2015).
Emms, "OrthoFinder: solving fundamental biases in whole genome comparisons dramatically improves orthogroup inference accuracy.", Genome Biol. 16:157 (2015).
Fibach-Paldi et al., "Key physiological properties contributing to rhizosphere adaptation and plant growth promotion abilities of Azospirillum brasilense.", FEMS Microbiol Lett. 326:99-108 (2012).
Finkel et al., "Global abundance of microbial rhodopsins." ISME J. 7:448-451 (2013).
Finn RD, et al. HMMER web server: 2015 update. Nucleic Acids Res. 2015; 43:W30-W38. [PubMed: 25943547].
Finn et al., "The Pfam protein families database: towards a more sustainable future." Nucleic Acids Res. 44:D279-D285 (2016).
Gao et al., "Genome-wide RNA sequencing analysis of quorum sensing-controlled regulons in the plant-associated Burkholderia glumae PG1 strain." Appl Environ Microbiol. 81:7993-8007 (2015).
Gottel et al., "Distinct microbial communities within the endosphere and rhizosphere of Populus deltoides roots across contrasting soil types." Appl Environ Microbiol. 77:5934-5944 (2011).
Hacquard et al., "Microbiota and host nutrition across plant and animal kingdoms.", Cell Host Microbe. 17:603-616 (2015).
Hadjithomas et al., "IMG-ABC: a knowledge base to fuel discovery of biosynthetic gene clusters and novel secondary metabolites." MBio.6:e00932 (2015), 10 pages.
Haft et al., "The TIGRFAMs database of protein families." Nucleic Acids Res. 31:371-373 (2003).
Hardoim et al., "The hidden world within plants: ecological and evolutionary considerations for defining functioning of microbial endophytes." Microbiol Mol Biol Rev. 79:293-320 (2015).
Hershey et al., "Functional conservation of the capacity for ent-kaurene biosynthesis and an associated operon in certain rhizobia." J Bacteriol. 196:100-106 (2014).
Hiei et al., "Efficient transformation of rice (*Oryza sativa* L) mediated by Agrobacterium and sequence analysis of the boundaries of the T-DNA." Plant J. 6:271-82 (1994).
Ho et al., "A view to a kill: the bacterial type VI secretion system." Cell Host Microbe. 15:9-21 (2014).
Hueck, "Type III protein secretion systems in bacterial pathogens of animals and plants.", Microbiol Mol Biol Rev. 62:379-433 (1998).
Hultman et al., "Multi-omics of permafrost, active layer and thermokarst bog soil microbiomes." Nature. 521:208-212 (2015).
Huntemann et al., The standard operating procedure of the DOE-JGI Microbial Genome Annotation Pipeline (MGAP v. 4)., Stand Genomic Sci. 1-6 (2015).
Immunology of fungal infections. Springer; Netherlands: 2007.
Ives et al., "Phylogenetic logistic regression for binary dependent variables." Syst Biol. 59:9-26 (2010).
Kanehisa et al., "KEGG as a reference resource for gene and protein annotation." Nucleic Acids Res. 44:D457-D462 (2016).
Katoh et al., "MAFFT: a novel method for rapid multiple sequence alignment based on fast Fourier transform." Nucleic Acids Res. 30:3059-3066 (2002).
Kerepesi et al., "AmphoraNet: The webserver implementation of the AMPHORA2 metagenomic workflow suite." Gene. 533:538-540 (2014).
Kroj et al., "Integration of decoy domains derived from protein targets of pathogen effectors into plant immune receptors is widespread." New Phytol. 210:618-626 (2016).
Le Roux C et al., "A receptor pair with an integrated decoy converts pathogen disabling of transcription factors to immunity." Cell. 161:1074-1088 (2015).
Ley et al. "Evolution of mammals and their gut microbes." Science. 320:1647-1651 (2008).
Long, "Rhizobium-legume nodulation: Life together in the underground." Cell. 56:203-214 (1989).
Louca et al., "Integrating biogeochemistry with multiomic sequence information in a model oxygen minimum zone." Proc Natl Acad Sci USA. 113:E5925-E5933 (2016).
Lundberg et al., "Defining the core *Arabidopsis thaliana* root microbiome." Nature. 488:86-90 (2012).
Ma et al., "Overexpression of a wheat jasmonate-regulated lectin increases pathogen resistance." Biochimie. 92:187-193 (2010).
MacIntyre et al., "The Vibrio cholerae type VI secretion system displays antimicrobial properties." Proc Natl Acad Sci U S A. 107:19520-19524 (2010).
Mukhtar et al., "Independently evolved virulence effectors converge onto hubs in a plant immune system network." Science. 333:596-601 (2011).
Nett et al., "Elucidation of gibberellin biosynthesis in bacteria reveals convergent evolution." Nat Chem Biol. 13:69-74 (2016).
Ofek-Lalzar et al., "Niche and host-associated functional signatures of the root surface microbiome." Nat Commun. 5:4950 (2014), 9 pages.
Osborn et al., "Lipopolysaccharide of the gram-negative cell wall." Science. 145:783-9 (1964).
Parks et al., "CheckM: assessing the quality of microbial genomes recovered from isolates, single cells, and metagenomes." Genome Res. 25:1043-1055 (2015).
Peiffer et al., "Diversity and heritability of the maize rhizosphere microbiome under field conditions." Proc Natl Acad Sci U S A. 110:6548-6553 (2013).
Peters et al., "A plant flavone, luteolin, induces expression of Rhizobium meliloti nodulation genes." Science. 233:977-980 (1986).
Pfeilmeier et al., "Bacterial pathogenesis of plants: future challenges from a microbial perspective." Mol Plant Pathol. 17:1298-1313 (2016).
Poggio et al., "A complete set of flagellar genes acquired by horizontal transfer coexists with the endogenous flagellar system in Rhodobacter sphaeroides." J Bacteriol. 189:3208-3216 (2007).

(56) References Cited

OTHER PUBLICATIONS

Price et al., "Molecular mimicry by an F-Box effector of Legionella pneumophila hijacks a conserved polyubiquitination machinery within macrophages and protozoa." PLoS Pathog. 5:e1000704 (2009), 13 pages.
Price et al., "FastTree 2—approximately Maximum-Likelihood trees for large alignments." PLoS One. 5:e9490 (2010), 10 pages.
Ravcheev et al., "Comparative genomics and evolution of regulons of the Lacl-family transcription factors." Front Microbiol. 5:294 (2014), 16 pages.
Rinke et al., "Insights into the phylogeny and coding potential of microbial dark matter." Nature. 499:431-437 (2013).
Rothmeier et al., "Activation of Ran GTPase by a Legionella effector promotes microtubule polymerization, pathogen vacuole motility and infection." PLoS Pathog. 9:e1003598 (2013), 17 pages.
Ruvkun et al., "Directed transposon Tn5 mutagenesis and complementation analysis of Rhizobium meliloti symbiotic nitrogen fixation genes." Cell. 29:551-559 (1982).
Sahly et al., "Surfactant protein D binds selectively to Klebsiella pneumoniae lipopolysaccharides containing mannose-rich O-antigens." J Immunol. 169:3267-3274 (2002).
Santhanam et al., "Native root-associated bacteria rescue a plant from a sudden-wilt disease that emerged during continuous cropping." Proc Natl Acad Sci U S A.112:E5013-E5020 (2015).
Sarris et al., "A plant immune receptor detects pathogen effectors that target WRKY transcription factors." Cell. 161:1089-1100 (2015).
Sarris et al., "Comparative analysis of plant immune receptor architectures uncovers host proteins likely targeted by pathogens." BMC Biol. 14:8. (2016), 19 pages.
Scharf et al., "Chemotaxis signaling systems in model beneficial plant-bacteria associations." Plant Mol Biol. 90:549-559 (2016).
Sen et al., "Phylogeny of the class Actinobacteria revisited in the light of complete genomes." Int J Syst Evol Microbiol. 64:3821-3832 (2014).
Shade et al., "Unexpected diversity during community succession in the apple flower microbiome." MBio. 4:e00602-12 (2013), 12 pages.
Shevchik et al., "Pectate lyase PelI of Erwinia chrysanthemi 3937 belongs to a new family." J Bacteriol. 179:7321-7330 (1997).
Sprent Ji. "60Ma of legume nodulation. What's new? What's changing?" J Exp Bot. 59:1081-1084. (2008).
Stamatakis et al., "A rapid bootstrap algorithm for the RAxML web servers." Syst Biol. 57:758-771 (2008).
Stebbins et al., "Structural mimicry in bacterial virulence." Nature. 412:701-705 (2001).
Tans-Kersten et al., "Ralstonia solanacearum needs motility for invasive virulence on tomato." J Bacteriol. 183:3597-3605 (2001).
Tatusov et al., "The COG database: a tool for genome-scale analysis of protein functions and evolution." Nucleic Acids Res. 28:33-36 (2000).
Tian et al., "The type VI protein secretion system contributes to biofilm formation and seed-to-seedling transmission of Acidovorax citrulli on melon." Mol Plant Pathol. 16:38-47 (2015).
Traore, "Characterization of Type Three Effector Genes of A citrulli, the Causal Agent of Bacterial Fruit Blotch of Cucurbits." Virginia Polytechnic Institute and State University (2014).
Turner et al. "Comparative metatranscriptomics reveals kingdom level changes in the rhizosphere microbiome of plants." ISME J. 7:2248-2258 (2013).
Varghese et al., "Microbial species delineation using whole genome sequences." Nucleic Acids Res. 43:6761-6771 (2015).
Wang et al., "A Phylum-Level Bacterial Phylogenetic Marker Database." Mol Biol Evol. 30:1258-1262 (2013).
Weidenbach et al. "Polarized defense against fungal pathogens is mediated by the Jacalin-related lectin domain of modular Poaceae-specific proteins." Mol Plant. 9:514-527 (2016).
Weller-Stuart et al., "Swimming and twitching motility are essential for attachment and virulence of Pantoea ananatis in onion seedlings." Mol Plant Pathol. 5:734-745 (2016).
Weston et al., "Pseudomonas fluorescens induces strain-dependent and strain-independent host plant responses in defense networks, primary metabolism, photosynthesis, and fitness." Mol Plant-Microbe Interact. 25:765-778 (2012).
Wu et al. "Accounting for alignment uncertainty in phylogenomics." PLoS One. 7:e30288 (2012), 10 pages.
Xiang et al., "A jacalin-related lectin-like gene in wheat is a component of the plant defence system." J Exp Bot. 62:5471-5483 (2011).
Xu et al. "AvrACXcc8004, a Type III Effector with a Leucine-Rich Repeat domain from Xanthomonas campestris Pathovar campestris confers avirulence in vascular tissues of *Arabidopsis thaliana* ecotype Col-0." J Bacteriol. 190:343-355 (2008).
Yamaji et al., "Lectin-mediated resistance impairs plant virus infection at the cellular level." Plant Cell. 24:778-793 (2012).
Yamauchi et al., "NADPH-dependent reductases involved in the detoxification of reactive carbonyls in plants." J Biol Chem. 286:6999-7009 (2011).
Gadjeva et al., "Mannan-binding lectin—a soluble pattern recognition molecule." Mol Immunol. 41:113-121 (2004).
Vimr et al., "To sialylate, or not to sialylate: that is the question." Trends Microbiol. 2002; 10:254-7 (2002).

* cited by examiner

A PA gene according to hypergbin
A PA gene according to phyloglmbin
A PA gene according to Scoary

*Alphaproteobacteria, Bradyrhizobium sp. ARR65*

Figure 2C — Nodulation

*Burkholderiales, Burkholderia kururiensis M130*

Figure 2D — Nitrogen Fixation

*Alphaproteobacteria, Rhizobium* etli bv. mimosae IE4771

*Alphaproteobacteria, Rhizobium* leguminosarum bv. viciae 3841

*Xanthomonadaceae, Xanthomonas* axonopodis pv. vasculorum NCPPB 900
Type III secretion system

***Burkholderiales, Variovorax* sp. Root411**
Type VI secretion system

***Alphaproteobacteria, Ensifer* Rmedicae WSM1115**
Flagellum Biosynthesis

- *Ps. syringae* B728a (pBQ9, SpectR)
- *Ps. tomato* DC3000 (luxCDABE, KanR)
- *R. solanacearum* AW1 (eps-130::lacZ phcB83::Tn5, KanR)
- *Xc. campestris* LMG568 (pTE101_empty)
- *A. tumefaciens* C58 (pTE101_empty)

METHODS AND COMPOSITIONS USEFUL FOR INHIBITING GROWTH OF CERTAIN BACTERIA

CROSS-REFERENCE TO RELATED APPLICATIONS

This application claims priority as a continuation application to PCT International Patent Application No. PCT/US2018/059277, filed Nov. 5, 2018, which claims priority to U.S. Provisional Patent Application Ser. No. 62/581,556, filed on Nov. 3, 2017, which are hereby both incorporated by reference in their entireties.

STATEMENT OF GOVERNMENTAL SUPPORT

The invention was made with government support under Contract Nos. DE-AC02-05CH11231 awarded by the U.S. Department of Energy and Grant No. IOS-1343020 awarded by the National Science Foundation. The government has certain rights in the invention.

FIELD OF THE INVENTION

The present invention is in the field of inhibiting the growth of certain bacteria.

BACKGROUND OF THE INVENTION

The microbiota of plants and animals have co-evolved with their hosts for millions of years[1-3]. Due to photosynthesis, plants serve as a rich source of carbon for diverse bacterial communities. These include mutualists and commensals, as well as pathogens. Phytopathogens and plant growth-promoting bacteria significantly affect plant growth, health, and productivity[4-7]. Except for intensively studied relationships such as root nodulation in legumes[8], T-DNA transfer by *Agrobacterium*[9], and type III secretion-mediated pathogenesis[10], the understanding of molecular mechanisms governing plant-microbe interactions is quite limited. It is therefore important to identify and characterize the bacterial genes and functions that help microbes thrive in the plant environment. Such knowledge should improve our ability to combat plant diseases and harness beneficial bacterial functions for agriculture, directly impacting global food security, bioenergy, and carbon sequestration.

Cultivation-independent methods based on profiling of marker genes or shotgun metagenome sequencing have considerably improved our understanding of microbial ecology in the plant environment[11-15]. In parallel, the reduction of sequencing costs has enabled the genome sequencing of plant-associated (PA) bacterial isolates at a large scale[16]. Importantly, isolates enable functional validation of in silico predictions. Isolate genomes also provide genomic and evolutionary context for individual genes and the ability to access genomes of rare organisms that might be missed by metagenomics due to limited sequencing depth. While metagenome sequencing has the advantage of capturing the DNA of uncultivated organisms, multiple 16S rRNA gene surveys have reproducibly shown that the most common plant-associated bacteria are mainly derived from four phyla[13,17] (Proteobacteria, Actinobacteria, Bacteroidetes, and Firmicutes) that are amenable to cultivation. Thus, bacterial cultivation is not a major limitation when sampling the abundant members of the plant microbiome[16].

SUMMARY OF THE INVENTION

The present invention provides for a composition comprising a purified or isolated Hyde1 gene product, or a functional fragment thereof.

In some embodiments, the Hyde1 gene product comprises an amino acid sequence having at least 70%, 80%, 90%, 95%, or 99% amino acid identity with any one of SEQ ID NOs:1-11. In some embodiments, the Hyde1 gene product comprises one or more of the following conserved amino acid sequences: VYRLE (SEQ ID NO:12), VYRLD (SEQ ID NO:13), QRXXH (SEQ ID NO:14), VRLYRI (SEQ ID NO:15), VRLYRV (SEQ ID NO:16), VRLHRI (SEQ ID NO:17), VRLHRV (SEQ ID NO:18), IRLYRI (SEQ ID NO:19), IRLYRV (SEQ ID NO:21), IRLHRI (SEQ ID NO:22), IRLHRV (SEQ ID NO:23), PXXLLGXSXXVDXW (SEQ ID NO:24), PXXLLGXSXXVDLW (SEQ ID NO:25), and PXXLLGXSXXVDIW (SEQ ID NO:20), wherein X is any naturally occurring amino acid.

In some embodiments, the Hyde1 gene product is Aave_0989, Aave_3191, or any other Hyde1 gene described herein.

In some embodiments, the Hyde1 gene product is capable of killing a broad array of plant pathogenic bacterial species.

The present invention provides for a pharmaceutical composition comprising the composition of claim 1 and a pharmaceutically acceptable carrier.

The present invention provides for a medicant manufactured using the composition of the present invention.

The present invention provides for a modified host cell comprises one or more genes encoding, and/or capable of expressing, a Type VI secretion system (T6SS), Hyde1, and/or Hyde2, or a functional fragment thereof.

The present invention provides for a modified bacterial cell comprises one or more genes encoding, and/or capable of expressing, a Type VI secretion system (T6SS), wherein the bacterial cell is a naturally occurring and pathogenic to a subject but is modified to be not pathogenic to the organism.

In some embodiments, the subject is a plant or a mammal, such as a human. In some embodiments, the subject is known to be, suspected to be, or has a high probability of being infected or contaminated with a pathogenic bacteria. In some embodiments, the subject is a human patient.

In some embodiments, the bacterial cell is modified to reduce expression of, or is knocked out for, a Type III secretion system (T3SS) or Type IV secretion system (T4SS) that the unmodified bacterial cell naturally is capable of expressing.

In some embodiments, the bacterial cell is a Hyde1 positive strain. In some embodiments, the bacterial cell is modified to make it not pathogenic. In some embodiments, the bacterial cell naturally contains or expresses Hyde1, wherein optionally the bacterial cell is modified to make it not pathogenic.

The present invention provides for a method of treating a plant diseases caused all or in part by a bacterial cell, comprising: administering a composition to a plant, or a part thereof, in need thereof.

In some embodiments, the part is a seed, root, stem, stalk, branch, leaf, flower, or fruit.

The present invention provides for a method of treating a disease caused all or in part by a bacterial cell, comprising: administering a pharmaceutical composition or medicant of the present invention to a subject in need thereof.

In some embodiments, the bacterial cell is a human pathogen and the subject is a human patient.

In some embodiments, the bacterial cell is a species from a genus selected from the group consisting of *Escherichia, Enterococcus, Staphylococcus, Klebsiella, Acinetobacter, Pseudomonas*, and *Enterobacter.*

In some embodiments, the bacterial cell is an *Escherichia coli, Enterococcus faecium, Enterobacter cloacae, Enterobacter aerogenes, Staphylococcus aureus, Klebsiella pneumonia, Acinetobacter baumannii*, or *Pseudomonas aeruginosa.*

The present invention provides for a method to limit or reduce growth of a pathogenic bacteria in an environment, comprising: introducing a non-pathogenic bacterial comprising one or more genes encoding, and/or capable of expressing, a Type VI secretion system (T6SS), Hyde1, and/or Hyde2, or functional fragment thereof, to an environment; whereby expression of the Type VI secretion system (T6SS), Hyde1, and/or Hyde2, or functional fragment thereof, limits or reduces growth of a pathogenic bacteria in the environment.

In some embodiments, the environment is an intensive care unit (ICU), or is known to be, suspected to be, or has a high probability of being infected or contaminated with a pathogenic bacteria.

A group of novel proteins (Hyde1 proteins) in the bacterial genus *Acidovorax* are used to kill competing organisms, including bacterial plant pathogens. The proteins are likely injected through type VI secretion system. Most of the organisms encoding for these proteins are plant pathogens but they can be mutated and turned into non-pathogens or transfer the relevant toxic genes into non-pathogenic bacteria. The resulting bacterial strains can be used as biocontrol agents to limit plant pathogens and possibly also human pathogens. 13 out of 16 bacterial strains tested as prey cells are killed in vitro by the *Acidovorax* strain encoding Hyde1 proteins. Bacterial killing of prey cells is significantly reduced when the Hyde proteins are deleted or when T6SS is deleted. It is shown that direct expression of the toxic protein is very toxic to the recipient bacterial cell. Antibacterial properties of Hyde proteins in bacteria dwelling in the plant environments and as a pure protein are tested. Many Hyde-like proteins of potential antimicrobial properties are predicted and identified.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1A:
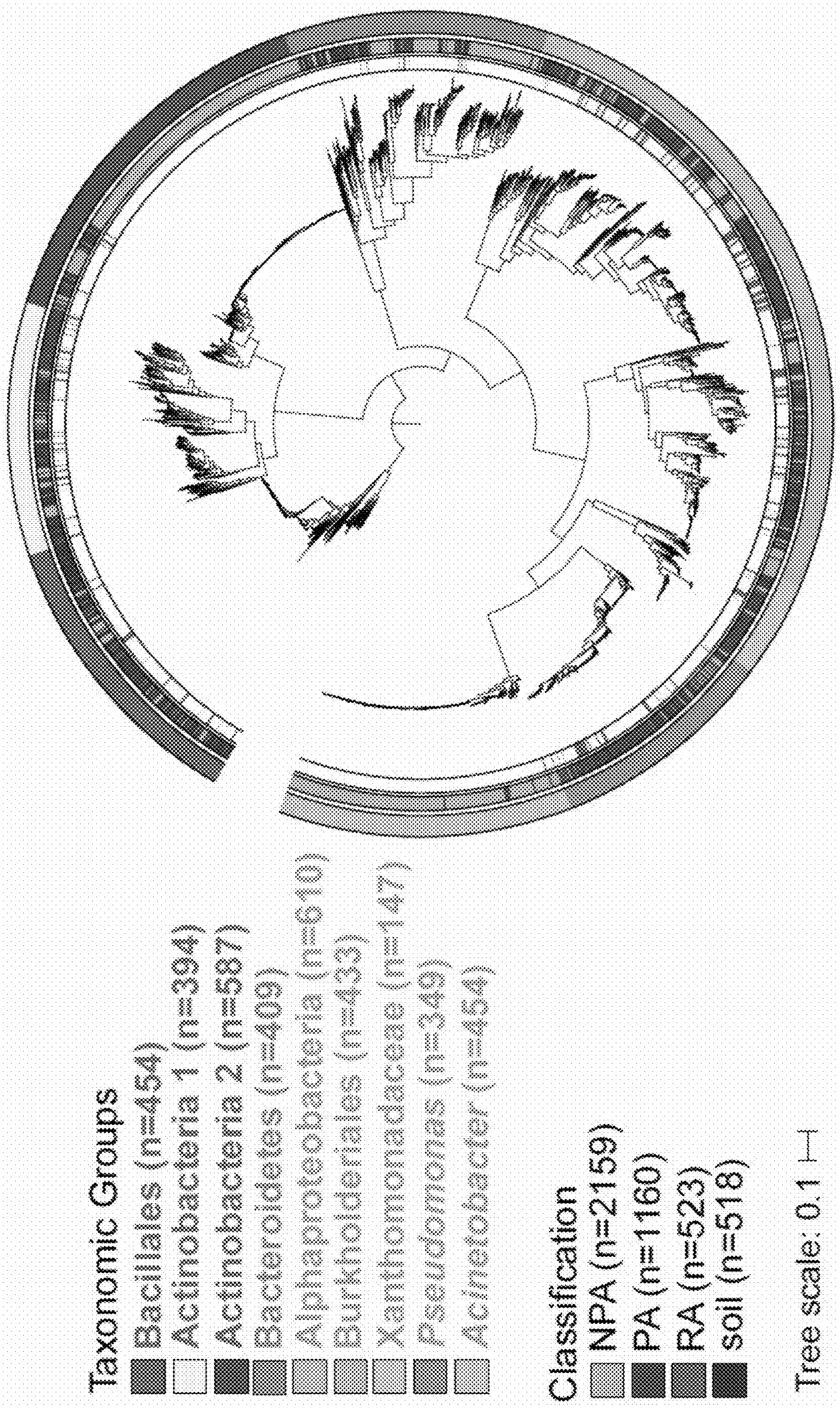
FIG. 1A. Genome dataset used in analysis and differences in gene category abundances. Maximum likelihood phylogenetic tree of 3837 high quality and non-redundant bacterial genomes based on the concatenated alignment of 31 single copy genes. Outer ring denotes the taxonomic group, central ring denotes the isolation source, and inner ring denotes the RA genomes within PA genomes. Taxon names are color-coded based on phylum: green—Proteobacteria, red—Firmicutes, blue—Bacteroidetes, purple—Actinobacteria. See URLs for ITOL interactive phylogenetic tree.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The term "about" refers to a value including 10% more than the stated value and 10% less than the stated value.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

One aspect of the invention comprises the utilization of a bacterial strain that colonizes plants as a way of eradicating plant pathogens (such as, serving as a biocontrol agent).

In some embodiments, the strain is *Acidovorax citrulli* AC000-1 (wild-type strain) which is shown in vitro to kill 13/16 bacterial strains tested when it is co-cultured with a competing bacterial strain for 19 hours.

Using computational biology tools developed, new genes ("Hyde1") are identified as being used in the killing. The genes are genetically associated with the T6SS loci through a putative adaptor gene that we named Hyde2. Two Hyde1 genes, sharing 53 amino acid sequence identity, were tested by expression in *E. coli*, and are shown to be highly toxic to *E. coli*, leading to nearly one million-fold reduction in colony forming units.

The wild-type (WT) and Hyde1 mutant strains are then tested against 16 different plant-associated bacterial strains including the following plant pathogens: *Pseudomonas syringae* B728a, *Pseudomonas syringae tomato* DC3000, *Ralstonia solanacearum* AW1, *Xanthomonas campestris* LMG568, and *Agrobacterium tumefaciens* C58. The WT strain clears 10-10,000 fold more bacteria than the Hyde1 deletion mutant. For example, the plant pathogen *Pseudomonas syringae* B728a is reduced by 10,000 fold when challenged with WT *Acidovorax citrulli* AC000-1. This effect is abolished when Hyde1 proteins are deleted. The most toxic protein may be Aave_0989 as a mutant containing the deletion of this gene abolished the killing of two competing bacterial strains.

The invention encompasses a large number of organisms that encode Hyde1 genes and Hyde1-like genes and may kill other competing pathogens.

In case of plant pathogens the main mechanisms for pathogenesis is known (T3SS and its secreted proteins) and hence, by deleting these genes we can produce non-pathogenic bacterial strains efficient in killing competitor cells.

By using the same computational biology approach described herein, one skilled in the art can predict other novel families of putatively antibacterial effect against other bacteria.

Figure 8:
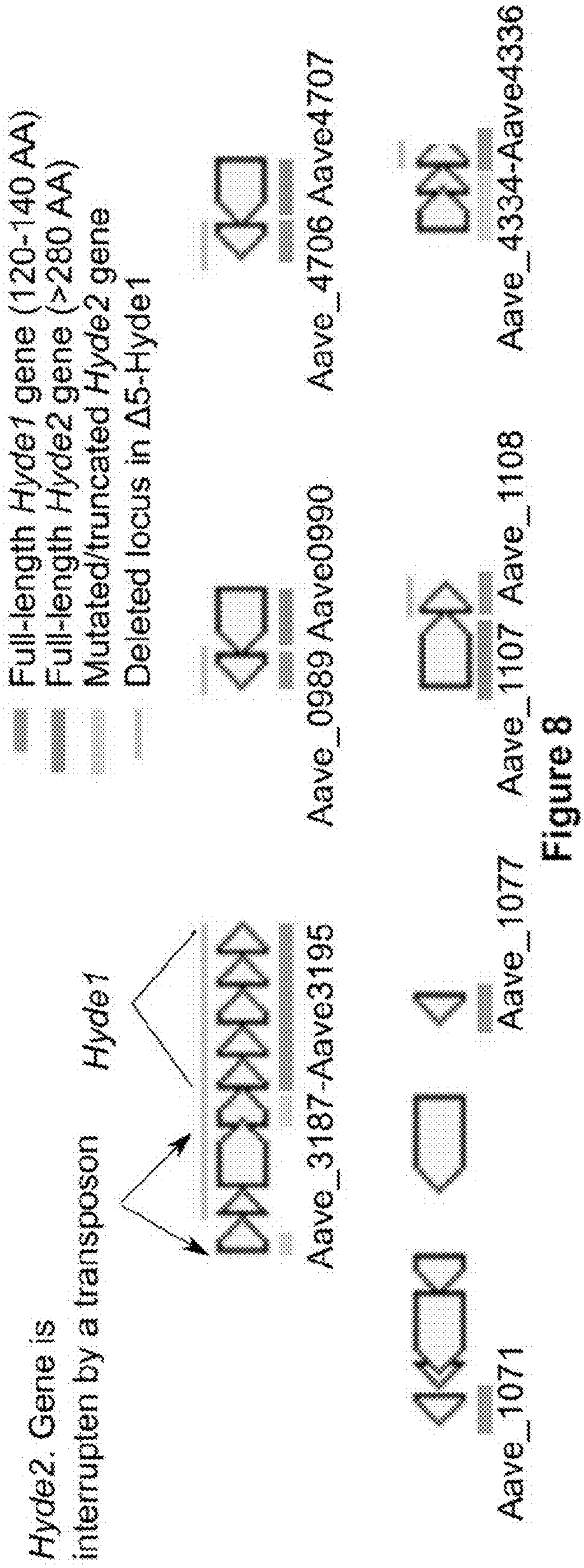
FIG. 8 shows the Hyde loci in strain *Acidovorax avenae citrulli* AAC00-1.

FIG. 8 shows the Hyde loci in strain *Acidovorax avenae citrulli* AAC00-1.

The following are exemplary Hyde1 amino acid sequences, which are all from the *Acidovorax avenae citrulli* AAC00-1 strain.

```
Aave_3191:
>639824391 YP_971528 hypothetical protein
[Acidovorax avenae subsp. citrulli AAC00-1:
NC_008752]
                                    (SEQ ID NO: 1)
MKLSNLKNVPCIVWCLGLNALFLAGWALATPTFADAENSPHRVYRLEFHK

ASFLQRITHPRFKMPYVVRLYRIEPKTLLGQSEVVDLWLNGEIHWYLDPP

VDMNRVRVGRDVLFESIPPECTKEAQIPSCPNTKP

Aave_3192:
>639824392 YP_971529 hypothetical protein
[Acidovorax avenae subsp. citrulli AAC00-1:
NC_008752]
                                    (SEQ ID NO: 2)
MKLSGLKNVPCILWCLALNACVVLGWYATKPTLFNSYNSPRYVYRLELYH

ASLWQRIIHYDQKAPFIVRLHRVDPKELLGESQVVDLWSGIDIDWQLDPL

VQTNKVYVGRDVIFRNIPPECTEAAQLQGCPNTKP

Aave_3193:
>639824393 YP_971530 hypothetical protein
[Acidovorax avenae subsp. citrulli AAC00-1:
NC_008752]
                                    (SEQ ID NO: 3)
MKLPNLKNVPCIVWCLGLNALLLAGWALATPTFADAENSPHRVYRLEFHK

ASFLQRITHPSFKMPYVVRLYRIEPKTLLGQSEVVDLWLNGEIHWYLDPP

VELSRVHVGQDVTFENIPPECTKEAQIPGCPDTKP

Aave_3914:
>639824394 YP_971531 hypothetical protein
[Acidovorax avenae subsp. citrulli AAC00-1:
NC_008752]
                                    (SEQ ID NO: 4)
MNLFNLKNAPCIVWCLALNACVVLGWYATTPTLFMTYNSPHSVYRLEIHR

ASPWQRIVHRDQEAPAIVRLYRIDPKELLGESKVVDLMDGSGIDWQLDPP

VQANKVYVGPGVVFENIPSECTAAGHIPGCPNTKP

Aave_3195:
>639824395 YP_971532 hypothetical protein
[Acidovorax avenae subsp. citrulli AAC00-1:
NC_008752]
                                    (SEQ ID NO: 5)
MKLSHLKKVPCIVWCLGLNALFLAGWALATPTFADAENSPHRVYRLEFHK

ASFLQRITHPRFKMPYVVRLYRIEPKTLLGQSEVVDLWLNGEIQWYLDPP

VDMNRVRVGRDVLFESIPSECSEAAQIPGCPNTKP
```

-continued

```
Aave_0989:
>639822189 YP_969361 hypothetical protein
[Acidovorax avenae subsp. citrulli AAC00-1:
NC_008752]
                                    (SEQ ID NO: 6)
MKLANLKSVPCIVWCLALNACLVLGWYATRPTLFMTYNSPHYVYRLEIYE

ASLWQRIVHHDQRDPGIFRLYEVNHKKLLGESKVVDLEPGIGAIDWYLDP

PMQANKVYAGLGVVFENIPSECPIVGQVPGCLSAKP

Aave_4706:
>639825902 YP_973015 hypothetical protein
[Acidovorax avenae subsp. citrulli AAC00-1:
NC_008752]
                                    (SEQ ID NO: 7)
MNFSQLKKIPCIVWCLAVNALVIMIWCAATPTFFDSENSPHRVYRLEFHK

ASLLQKIAHPTFKMPYIVRLYKIEPKTLLGESEVVDLWLNGEITWYLNSS

VDQNEVRVGRDVVFEKVPPECTPASPLVSCPKP

Aave_1071:
>639822270 YP_969442 hypothetical protein
[Acidovorax avenae subsp. citrulli AAC00-1:
NC_008752]
                                    (SEQ ID NO: 8)
MTTTRRFKVAALLLGIAVVGITLRSLATPEYQRSHYSPRHVYRLDYYEAS

WLQRMAHWDMRYPHVIRLYRIEPPALLGESAVVDLWINGQLYWYLNPPMN

KVRIGRDVVFENIPPECTGCPPLPDSAVMP

Aave_1077:
>639822270 YP_969442 hypothetical protein
[Acidovorax avenae subsp. citrulli AAC00-1:
NC_008752]
                                    (SEQ ID NO: 9)
MTTTRRFKVAALLLGIAVVGITLRSLATPEYQRSHYSPRHVYRLDYYEAS

WLQRMAHWDMRYPHVIRLYRIEPPALLGESAVVDLWINGQLYWYLNPPMN

KVRIGRDVVFENIPPECTGCPPLPDSAVMP

Aave_1108:
>639822305 YP_969477 hypothetical protein
[Acidovorax avenae subsp. citrulli AAC00-1:
NC_008752]
                                   (SEQ ID NO: 10)
MNGKRLVKWAVAAVLSAIVLGYSAIPRYDRSHYSPRHVYRLDYYEASWLQ

RLMHWNMKYPHVIRLYRIEPETLLGESGVVDLWLNGDINWWFDPPLNVVR

IGQDVVFENIPPECVDCPRLPDSVLMP

Aave_4336:
>639825522 YP_972650 hypothetical protein
[Acidovorax avenae subsp. citrulli AAC00-1:
NC_008752]
                                   (SEQ ID NO: 11)
MASNNKKMRTQTLWMVLALGLAAFVWYASKPVFKGSETSPMNVYRIEYYD

ASPIQRILHYQMKTPSFVRLYRIQPETLLGESEIVDIWMNGTLHWWTDPP

AHAVVVGSSVVFENIPAECPAATSCPR
```

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

Bacterial Genes Used in Killing or Inhibiting Growth of Plant Pathogenic Bacteria The present invention provides for a new genetic mechanism that efficiently inhibits growth of different bacteria grown in culture, including of plant pathogens.

The Type VI secretion system (T6SS) is used by bacteria to secrete proteins ("effectors") that are toxic to neighboring cells, mostly bacteria, but occasionally to eukaryotic host cells (plant or animal cells).

A set of new genes (Hyde 1) are discovered in bacteria that are pathogenic to plants (genus *Acidovorax*). The genes are restricted to the *Acidovorax* phytopathogens and are found in all 10 analyzed strains. The strains are originally isolated from the leaves of a large set of plants, including sugarcane, rice, lamb's lettuce, Konjac, watermelon, melon, maize and Citrullus lanatus. The genes are associated with T6SS. This is done by identifying the Hyde1 genes next to a set of other novel genes (hyde2) that are either located next to or within T6SS gene locus, or Hyde2 is fused to T6SS-associated proteins. Hyde2 may be an adaptor gene connecting Hyde1 genes to T6SS.

Figure 11:
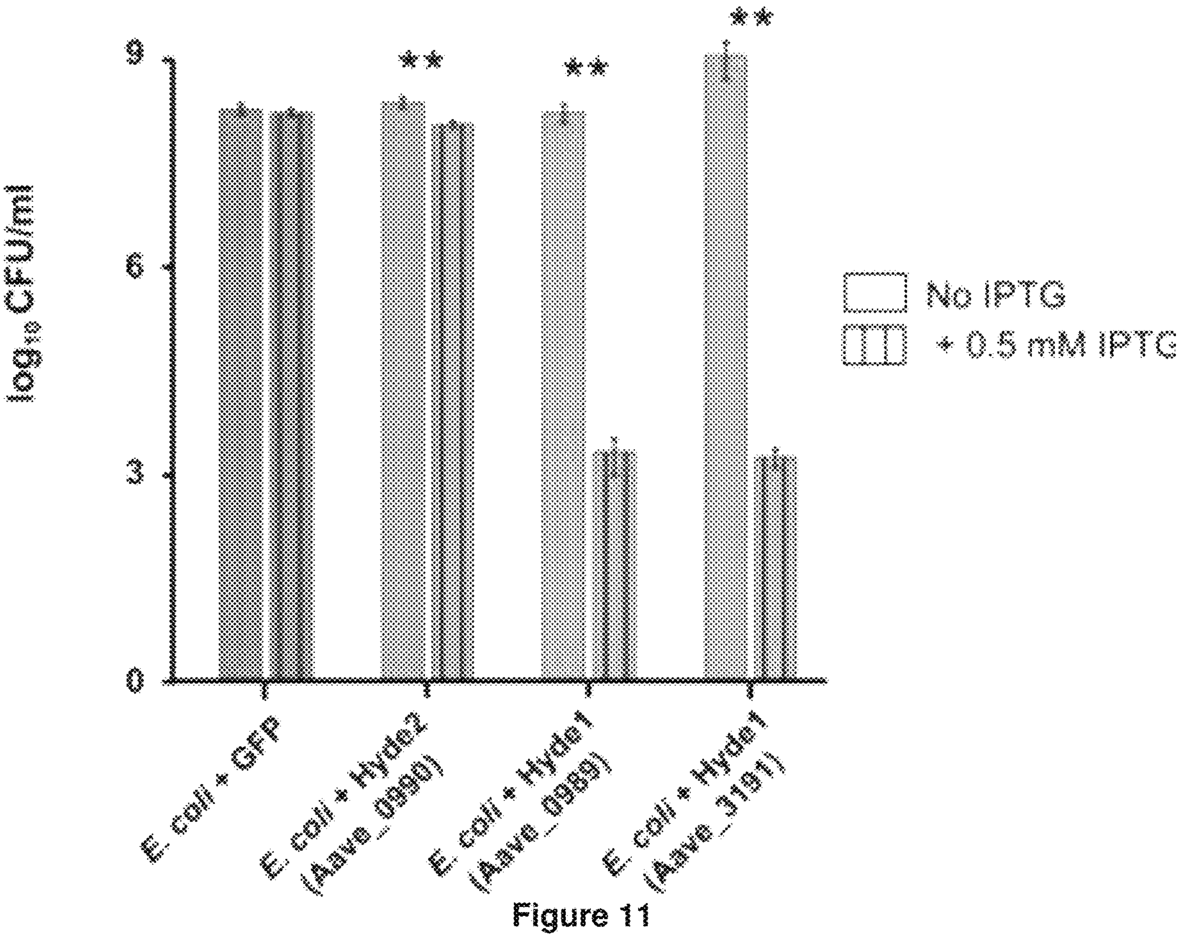
FIG. 11. Toxicity assay of Hyde proteins expressed in *E. coli* GFP, Hyde2-Aave_0990 gene, and two Hyde1 genes from two loci, Aave_0989 and Aave_3191, are cloned into pET28b and transformed into *E. coli* C41 cells. Aave_0989 and Aave_3191 are 53% identical. Bacterial culture (5 μL) from 5 independent colonies are spotted on LB plates with appropriate supplements. Gene expression of the cloned gene is induced using 0.5 mM IPTG. Double asterisks denote whether there is significant difference ($P < 0.05$, t-test).

When expressing two different Hyde1 genes (Aave_0989 and Aave_3191) in E. coli recipient cell, the number of bacterial colonies is reduced by $10^5$ fold in comparison to the expression of a non-toxic gene. The 9/11 Hyde1 genes in *Acidovorax citrulli* AC000-1 is deleted. See FIG. 11.

When co-culturing the wild-type *Acidovorax citrulli* strain (serving as a predator strain) with competing bacteria (serving as prey cells), the viability of the competing bacteria is reduced by up to 105 fold in comparison to the same experiment with deletion mutants either for Hyde1 or for T6SS. This is shown for 7/10 strains of prey cells tested. See FIG. 7B.

Figure 12:
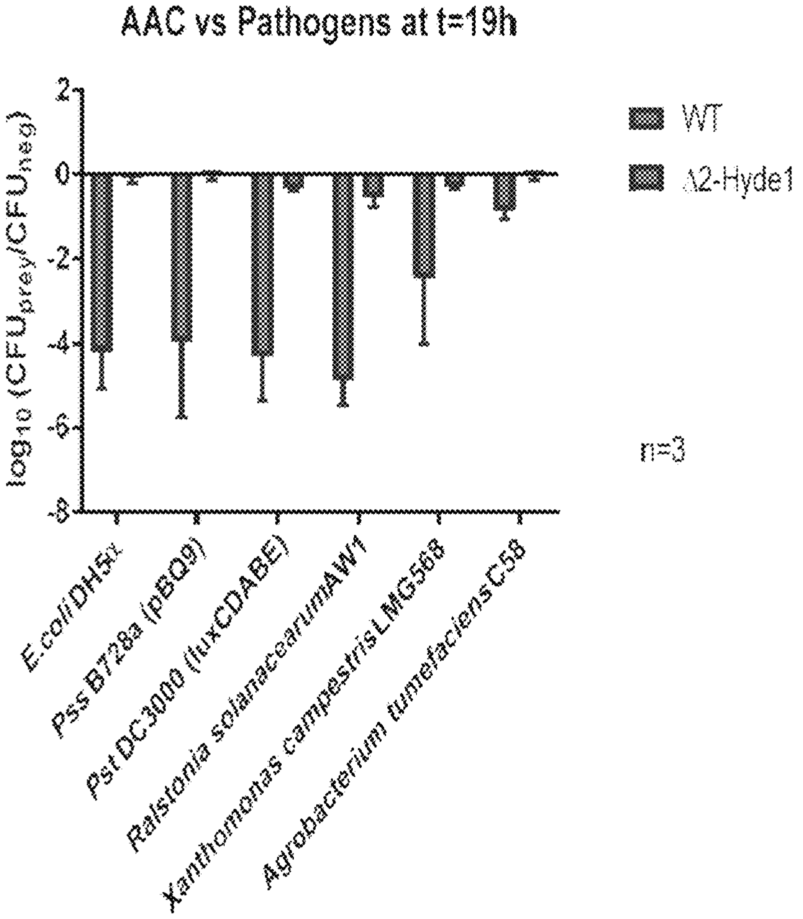
FIG. 12. *Acidovorax citrulli* AAC000-1 versus different pathogens.

*Acidovorax citrulli* AAC00-1 strain also inhibits growth or kill a set of plant pathogens. A deletion mutant for Aave_0989 gene abolished the Hyde1 toxicity against two prey strains (*E. coli* and L434). Hence the Aave_0989 gene demonstrated the strongest antibacterial property of the genes tested. See FIG. 12.

EXAMPLE 2

Genomic Features of Bacterial Adaptation to Plants

Plants intimately associate with diverse bacteria. Plant-associated bacteria have ostensibly evolved genes that enable them to adapt to plant environments. However, the identities of such genes are mostly unknown, and their functions are poorly characterized. 484 genomes of bacterial isolates from roots of Brassicaceae, poplar, and maize are sequenced. 3,837 bacterial genomes are compared to identify thousands of plant-associated gene clusters. Genomes of plant-associated bacteria encode more carbohydrate metabolism functions and fewer mobile elements than related non-plant-associated genomes do. Candidates from two sets of plant-associated genes are experimentally validated: one involved in plant colonization, and the other serving in microbe-microbe competition between plant-associated bacteria. 64 plant-associated protein domains are identified that potentially mimic plant domains; some are shared with plant-associated fungi and oomycetes. This expands the genome-based understanding of plant-microbe interactions and provides potential leads for efficient and sustainable agriculture through microbiome engineering.

An objective was to characterize the genes that contribute to bacterial adaptation to plants (plant-associated genes) and those genes that specifically aid in bacterial root colonization (root-associated genes). The genomes of 484 new bacterial isolates and single bacterial cells from the roots of Brassicaceae, maize, and poplar trees are sequenced. The newly sequenced with existing genomes into a dataset of 3837 high quality, non-redundant genomes are combined. A computational approach to identify plant-associated (PA) genes and root-associated (RA) genes based on comparison of phylogenetically-related genomes with knowledge of the origin of isolation is developed. Two sets of PA genes, including a novel gene family that functions in plant-associated microbe-microbe competition are experimentally validated. In addition, many PA genes that are shared between bacteria of different phyla and even between bacteria and PA eukaryotes are characterized. This represents a comprehensive and unbiased effort to identify and characterize candidate genes required at the bacterial-plant interface.

Results

Expanding the Plant-Associated Bacterial Reference Catalog

To obtain a comprehensive PA bacterial reference genome set, 191, 135, and 51 novel bacterial strains from the roots of Brassicaceae (91% from *Arabidopsis thaliana*), poplar trees (*Populus trichocarpa* and *Populus deltoides*), and maize, respectively, isolated and sequenced (Table 1). The bacteria are specifically isolated from either the root interior (endophytic compartment), the root surface (rhizoplane), or the soil attached to the root (rhizosphere) of plants. In addition, 107 single bacterial cells from surface-sterilized roots of *A. thaliana* are isolated and sequenced. All genomes are assembled, annotated and deposited in public databases and in a dedicated website.

TABLE 1

Novel and previously sequenced and genomes used in this analysis.

| Taxon | Taxonomic rank | # novel Sequenced PA genomes | # scanned genomes | # genomes used in analysis | # PA | # NPA | # Soil | # RA |
|---|---|---|---|---|---|---|---|---|
| Alphaproteobacteria* | Class | 126 | 784 | 610 | 368 | 199 | 43 | 169 |
| Burkholderiales* | Order | 85 | 612 | 433 | 160 | 209 | 64 | 86 |
| *Acinetobacter** | Genus | 4 | 926 | 454 | 7 | 442 | 5 | 3 |
| *Pseudomonas** | Genus | 75 | 506 | 349 | 169 | 137 | 43 | 61 |
| Xanthomonadaceae* | Family | 15 | 264 | 147 | 110 | 26 | 11 | 26 |
| Bacillales** | Order | 54 | 664 | 454 | 97 | 185 | 172 | 54 |

TABLE 1-continued

Novel and previously sequenced and genomes used in this analysis.

| Taxon | Taxonomic rank | # novel Sequenced PA genomes | # scanned genomes | # genomes used in analysis | # PA | # NPA | # Soil | # RA |
|---|---|---|---|---|---|---|---|---|
| Actinobacteria 1† | NA | 69 | 504 | 394 | 164 | 142 | 88 | 89 |
| Actinobacteria 2† | NA | 19 | 845 | 587 | 29 | 526 | 32 | 18 |
| Bacteroidetes†† | Phylum | 37 | 481 | 409 | 56 | 293 | 60 | 17 |
| Total | | 484 | 5586 | 3837 | 1160 | 2159 | 518 | 523 |

Taxon color denotes phylum:
*Proteobacteria,
**Firmicutes,
†Actinobacteria,
††Bacteroidetes.
PA—plant-associated bacteria, NPA—non-plant associated bacteria, soil—soil associated bacteria,RA—root-associated bacteria. NA—not available (an artificial taxon).

A Broad, High-Quality Bacterial Genome Collection

In addition to the newly sequenced genomes noted above, public databases are mined to collect 5587 bacterial genomes belonging to the four most abundant phyla of PA bacteria13 (Methods). Each genome is manually classified as PA, non-plant associated (NPA), or soil-derived based on its unambiguous isolation niche. The PA genomes include organisms isolated from plants or rhizospheres. A subset of the PA bacteria is also annotated as 'RA' when isolated from the rhizoplane or the root endophytic compartment. Genomes from bacteria isolated from soil are considered as a separate group, as it is unknown whether these strains can actively associate with plants. Finally, the remaining genomes are labeled as non-plant associated (NPA) genomes; these are isolated from diverse environments, including humans, animals, air, sediments, and aquatic environments. A stringent quality control process is performed to remove low quality or redundant genomes. This leads to a final dataset of 3837 high quality and non-redundant genomes, including 1160 PA genomes, 523 of which are also RA. These 3837 genomes are grouped into nine monophyletic taxa to allow comparative genomics among phylogenetically-related genomes (FIG. 1A).

To determine whether the genome collection from cultured isolates is representative of plant-associated bacterial communities, cultivation-independent 16S rDNA surveys and metagenomes from the plant environment of *Arabidopsis*11,12, barley18, wheat, and cucumber14 are analyzed. The nine taxa analyzed here account for 33-76% (median 41%, Supplementary Table 4) of the total bacterial communities found in PA environments and therefore represent a significant portion of the plant microbiota, consistent with previous reports13,16,19.

PA Genomes: More Sugar Metabolism, Less Mobile Elements

The genomes of bacteria isolated from plant environments with bacteria of shared ancestry yet isolated from non-plant environments are compared. The two groups should differ in the set of accessory genes that evolved as part of their adaptation to a specific niche. Comparison of the size of PA, soil, and NPA genomes reveal that PA and/or soil genomes are significantly larger than NPA genomes ($P<0.05$, PhyloGLM and t-tests). The trend is observed in 6-7 of the nine analyzed taxa (depending on the test), representing all four phyla. Pangenome analyses within a few genera having PA and NPA isolation sites reveal similar pangenome sizes between PA and NPA genomes.

Figure 1B:
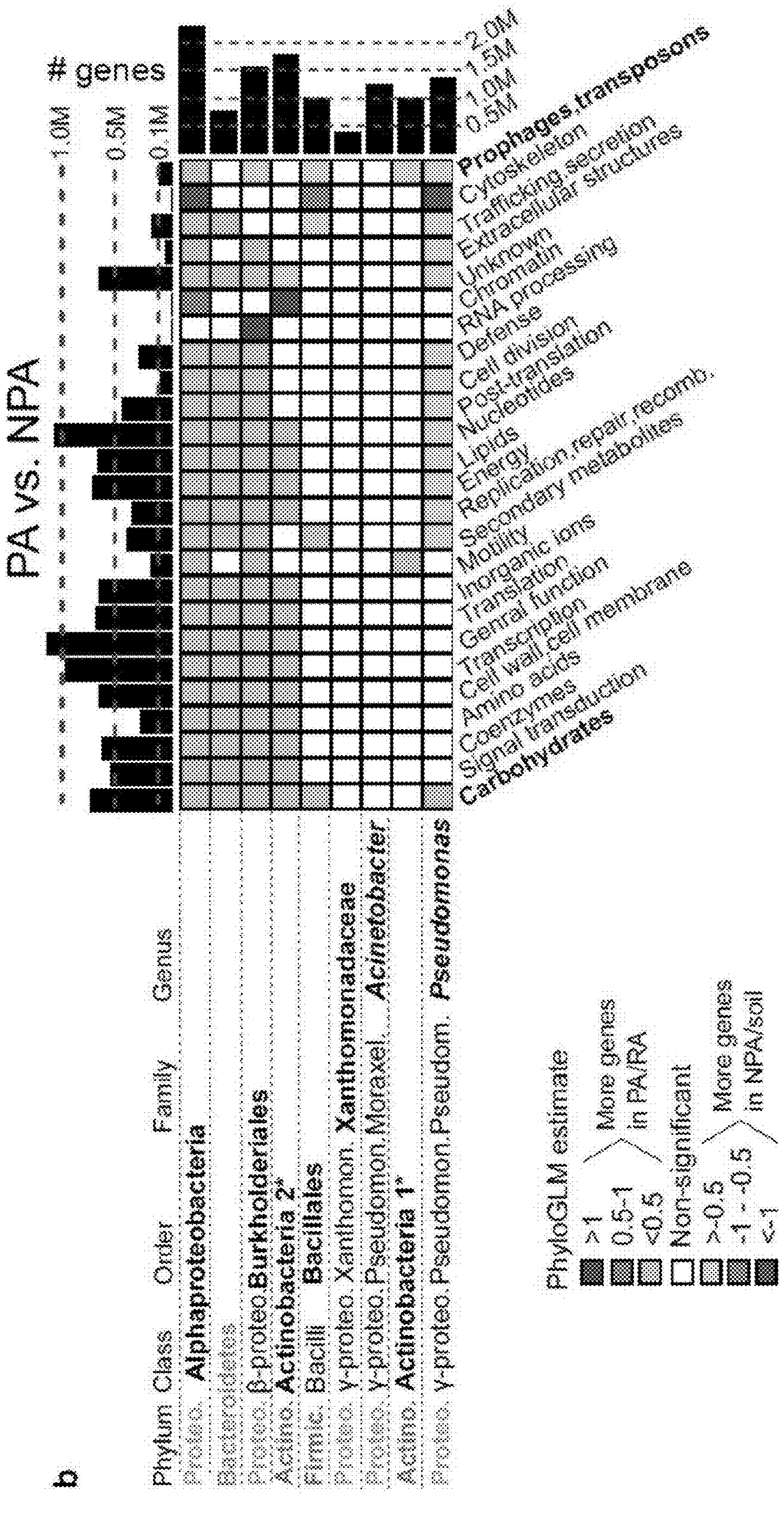
FIG. 1B. Genome dataset used in analysis and differences in gene category abundances. Differences in gene categories between PA/NPA (top panel) and RA/soil (bottom panel) genomes of the same taxon. For both panels, the heat map indicates the level of enrichment or depletion based on a PhyloGLM test. Significant (colored) cells have p value $<0.05$, FDR corrected. Hot colored cells indicate significantly more genes in PA and RA genomes in the upper and lower panels, respectively. Histograms on the upper and right margins represent the total number of genes compared in each column and row, respectively. PA—plant-associated, NPA—non-plant associated, RA—root associated, soil—soil-associated. * not a formal class name. Carbohydrates—Carbohydrate metabolism and transport gene category. Note that cells with high absolute estimate values (dark colors) are based on categories of few genes and are therefore more likely to be less accurate.
Figure 1B:
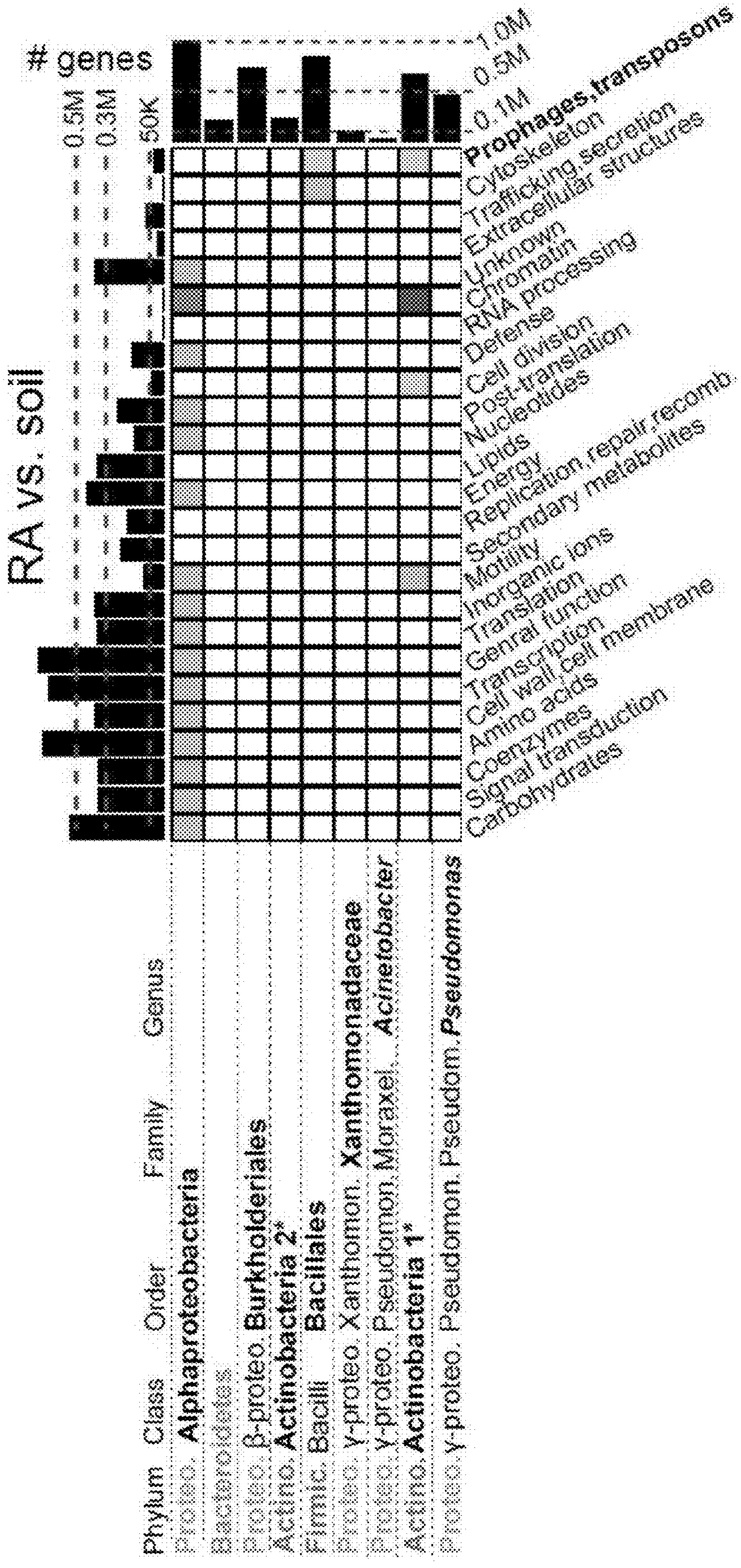

Next, whether certain gene categories are enriched or depleted in PA genomes compared to their NPA counterparts is examined, using 26 broad functional gene categories. Enrichments are detected using the PhyloGLM test (FIG. 1B) and t-test. Two gene categories demonstrate similar phylogeny-independent trends suggestive of an environment-dependent selection process. The "Carbohydrate metabolism and transport" gene category is expanded in the PA organisms of six taxa (FIG. 1B, upper panel). This is the most expanded category in Alphaproteobacteria, Bacteroidetes, Xanthomonadaceae, and *Pseudomonas*. In contrast, mobile genetic elements (phages and transposons) are underrepresented in four PA taxa (FIGS. 1B). Interestingly, PA genomes exhibit increased genome sizes despite a reduction in the mobile elements that often serve as vehicles for horizontal gene transfer and genome expansion. Comparison of RA bacteria to soil bacteria reveal less drastic changes than those seen between PA and NPA groups, as expected for organisms that live in more similar habitats (FIG. 1B).

Identification and Validation of PA and RA Genes

It is sought to identify specific genes that are enriched in PA and RA genomes, compared to NPA and soil-derived genomes, respectively. First, the proteins/protein domains of each taxon are clustered based on homology using different annotation resources: COG20, KEGG Orthology21 and TIGRFAM22, which typically comprise 35%-75% of all genes in bacterial genomes23. In order to capture in the analysis genes that do not have existing functional annotations, Orthofinder24 is used (following benchmarking) to cluster all protein sequences within each taxon into homology-based orthogroups. Finally, protein domains are clustered using Pfam25. These five protein/domain clustering approaches are used in parallel comparative genomics pipelines. Each protein/domain sequence is additionally labeled as originating from either a PA or a NPA genome.

Next, it is tested if protein/domain clusters are significantly associated with a PA lifestyle using five independent statistical approaches: hypergbin, hypergcn (two versions of the Hypergeometric test), phyloglmbin, phyloglmcn (two phylogenetic tests based on PhyloGLM26), and Scoary27, a stringent combined test. These analyses are based on either gene presence/absence or gene copy number. A gene is defined as significantly PA (henceforth "PA gene") if it belonged to a significant PA gene cluster by at least one test, and originated from a PA genome. Significant NPA, RA and soil genes are defined in the same way. Significant gene clusters found using the different methods had varying degrees of overlap. In general, it is noted there is a high degree of overlap between PA and RA genes and an overlap between NPA and soil genes. Overall, PA genes are depleted from NPA genomes from heterogeneous isolation sources. Performing principal coordinates analysis (PCoA) using matrices containing only the PA and NPA genes are derived from each method as features increased the separation of PA from NPA genomes along the first two axes.

Figure 2A:
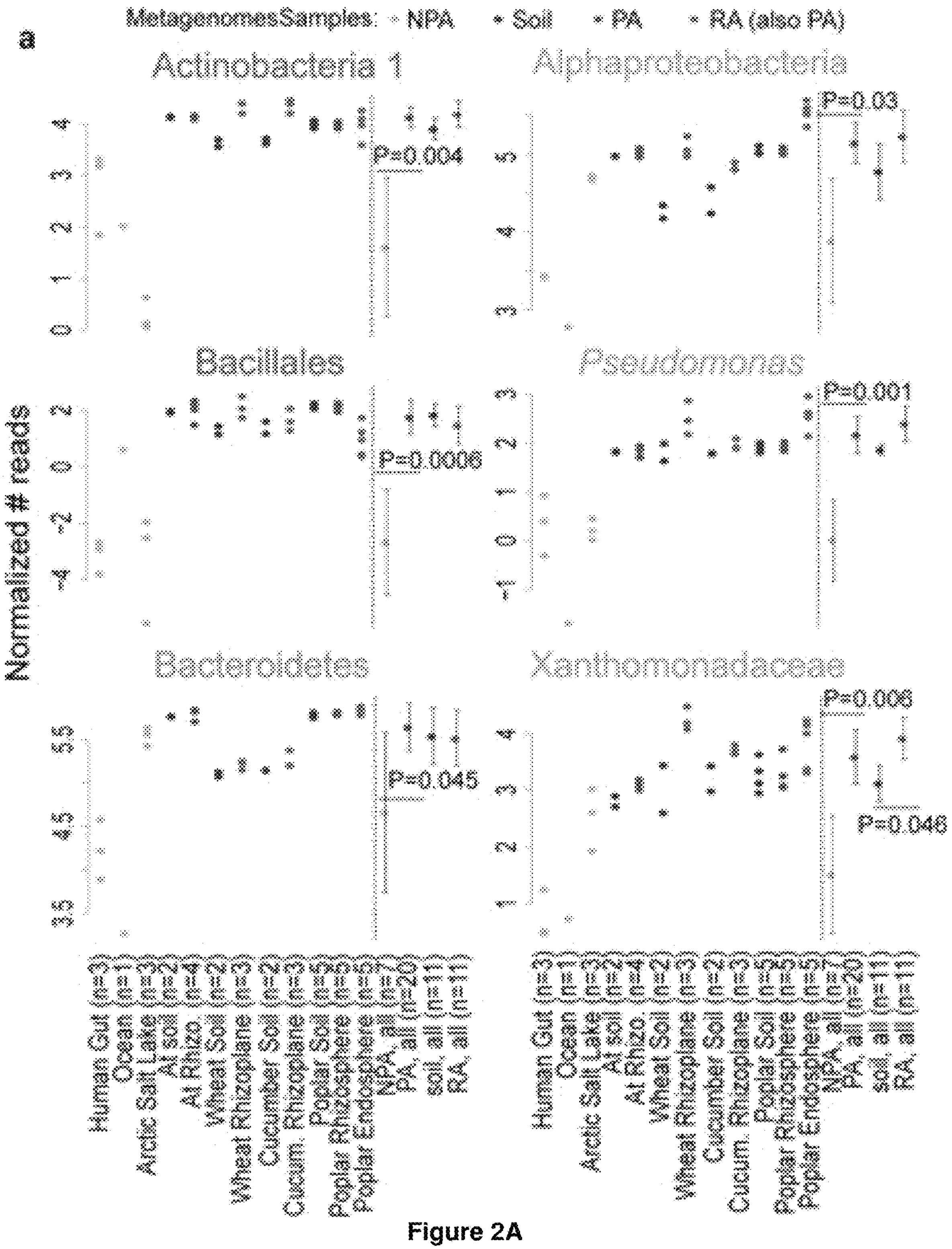
FIG. 2A. Validation of predicted PA genes using multiple approaches. PA genes, which were predicted based on isolate genomes, are more abundant in PA metagenomes than in NPA metagenomes. Reads from 38 shotgun metagenome samples were mapped to significant PA, NPA, RA, and soil genes predicted by Scoary. P values are indicated for the significant differences between the PA and NPA or RA and soil in each taxon (two sided t-test).

As a validation of predictions, the abundance patterns of PA/RA genes in natural environments are assessed. 38 publicly available PA, NPA, RA and soil shotgun metagenomes are retrieved, including some from PA environments that are not used for isolation of the bacteria analyzed here14,28,29. Reads from these culture-independent metagenomes to PA genes from all statistical approaches are mapped. PA genes in up to seven taxa are more abundant ($P<0.05$, t-test) in PA metagenomes than in NPA metagenomes (FIG. 2A). RA, soil-associated and NPA genes, on the other hand, are not necessarily more abundant in their expected environments.

Figure 2B:
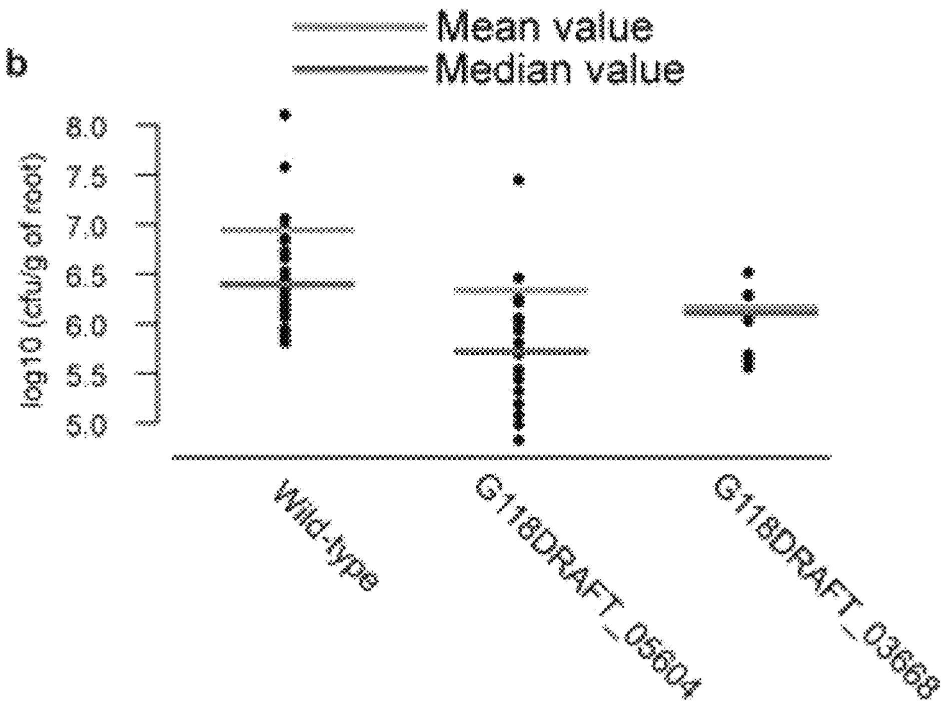
FIG. 2B. Validation of predicted PA genes using multiple approaches. Rice root colonization experiment using wild type *Paraburkholderia kururiensis* M130 or knockout mutants for two predicted PA genes. Two mutants exhibited reduced colonization in comparison to wild type: G118DRAFT_05604 (q-value=0.00013, wilcoxon rank sum test) encodes an outer membrane efflux transporter from the nodT family, and G118DRAFT_03668 (q-value=0.0952, wilcoxon rank sum test), a Tir chaperone protein (CesT). Each point represents the average count of a minimum of 3-6 plates derived from the same plantlet, expressed as cfu/g of root.

In addition, eight genes that were predicted as PA by multiple approaches are selected for experimental validation using an in planta bacterial fitness assay. The roots of surface-sterilized rice seedlings (n=9-30 seedlings/experiment) are inoculated with wild type *Paraburkholderia kururiensis* M130 (a rice endophyte30) or a knock-out mutant strain for each of the eight genes. The plants are grown for 11 days, collected and quantified the bacteria that were tightly attached to the roots. Mutations in two genes lead to four-six fold reduced colonization (FDR corrected Wilcoxon rank sum test, $q<0.1$) relative to wild type bacteria (FIG. 2B) without an observed effect on growth rate. These two genes encode an outer membrane efflux transporter from the nodT family and a Tir chaperone protein (CesT). It is plausible that the other six genes assayed function in facets of plant association not captured in this experimental context.

Figure 2C:
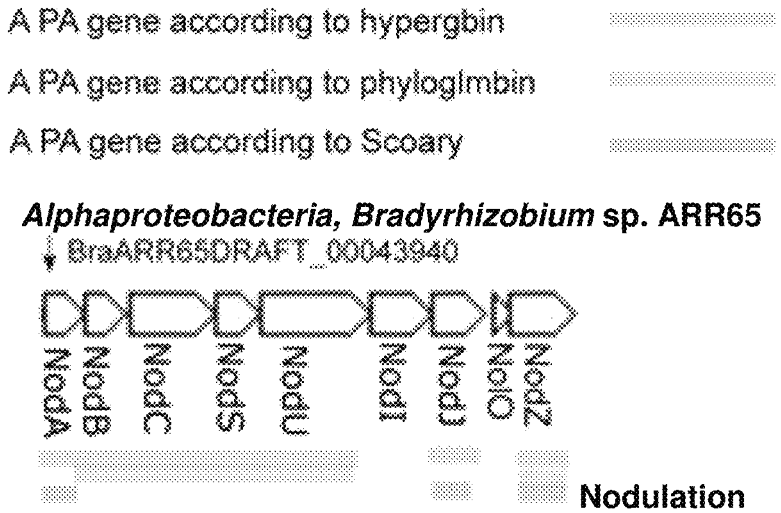
FIG. 2C. Validation of predicted PA genes using multiple approaches. Examples of known functional PA operons captured by different statistical approaches. The PA genes are underlined. Nod genes. Below each gene appears the gene symbol or the protein name where such information was available.
Figure 2D:
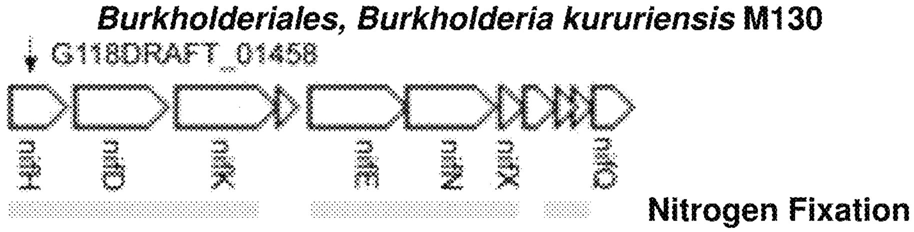
FIG. 2D. Validation of predicted PA genes using multiple approaches. Examples of known functional PA operons captured by different statistical approaches. The PA genes are underlined. NIF genes.
Figure 2E:
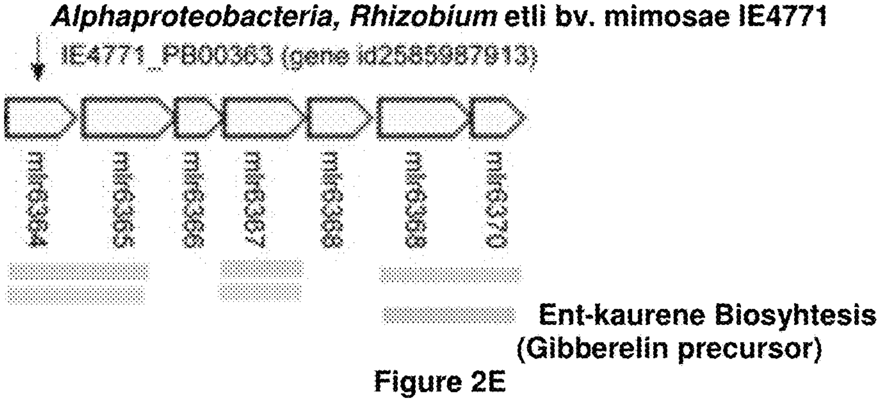
FIG. 2E. Validation of predicted PA genes using multiple approaches. Examples of known functional PA operons captured by different statistical approaches. The PA genes are underlined. ent-kaurene (gibberelin precursor).
Figure 2F:
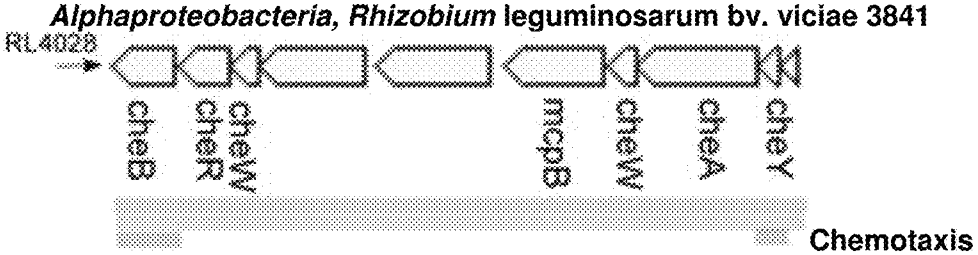
FIG. 2F. Validation of predicted PA genes using multiple approaches. Examples of known functional PA operons captured by different statistical approaches. The PA genes are underlined. Chemotaxis proteins in bacteria from different taxa.
Figure 2G:
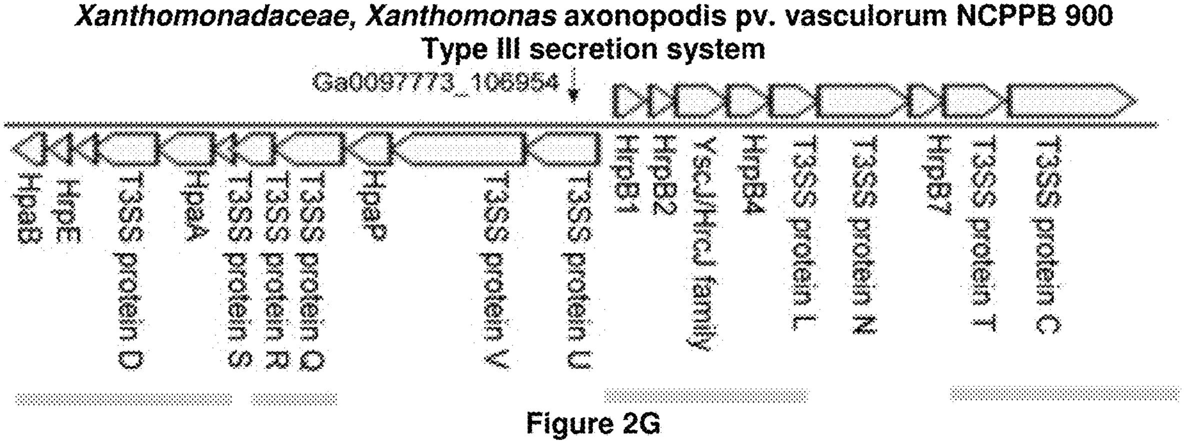
FIG. 2G. Validation of predicted PA genes using multiple approaches. Examples of known functional PA operons captured by different statistical approaches. The PA genes are underlined. Type III secretion system.
Figure 2H:
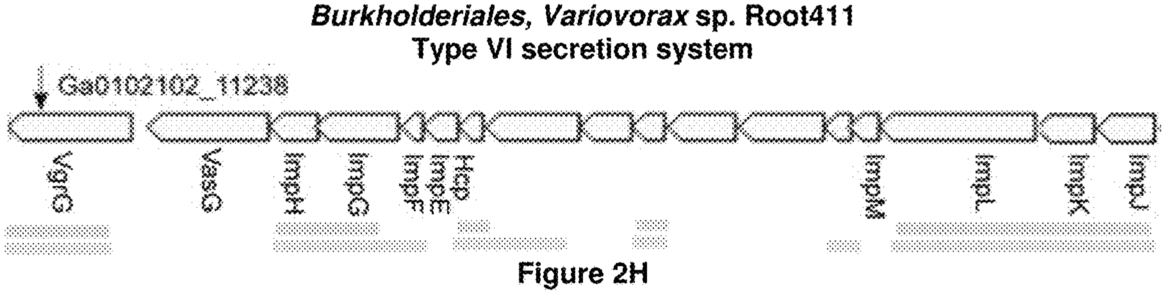
FIG. 2H. Validation of predicted PA genes using multiple approaches. Examples of known functional PA operons captured by different statistical approaches. The PA genes are underlined. Type VI secretion system, including the imp genes (impaired in nodulation).
Figure 2I:
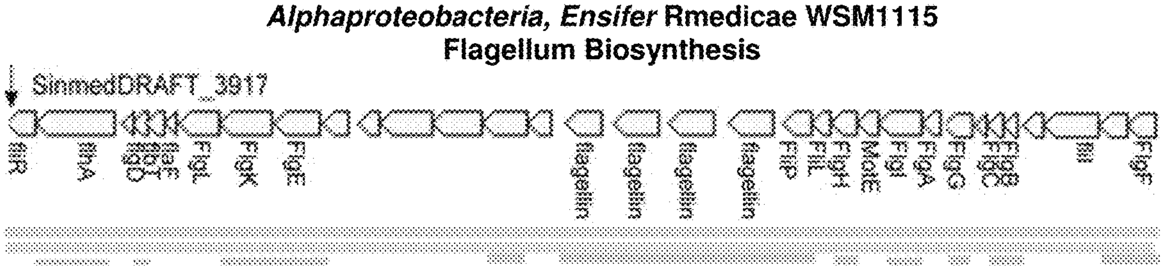
FIG. 2I. Validation of predicted PA genes using multiple approaches. Examples of known functional PA operons captured by different statistical approaches. The PA genes are underlined. Flagellum biosynthesis in Alphaproteobacteria.

Functions for which co-expression and cooperation between different proteins are needed are often encoded by gene operons in bacteria. It is tested whether the methods correctly predict known PA operons. PA and RA genes are grouped into putative PA and RA operons based on their genomic proximity and orientation. This analysis yielded some well-known PA functions, for example, the nodABCSUIJZ and nifHDKENXQ operons (FIGS. 2C and 2D). Nod and Nif proteins are integral for biological nitrogen cycling, mediating root nodulation31 and nitrogen fixation32, respectively. The biosynthetic gene cluster is identified for the precursor of the plant hormone gibberellin33, 34 (FIG. 2E). Other known PA operons identified are related to chemotaxis of diverse bacteria35, secretion systems such as T3SS36 and T6SS37, and flagellum biosyntheis38-40 (FIGS. 2F to 2I).

In summary, thousands of PA and RA gene clusters are identified by five different statistical approaches and validated these by computational and experimental approaches, broadening our understanding of the genetic basis of plant-microbe interactions and providing a valuable resource to drive further experimentation.

Protein Domains Reproducibly Enriched in Diverse PA Genomes

Figure 3A:
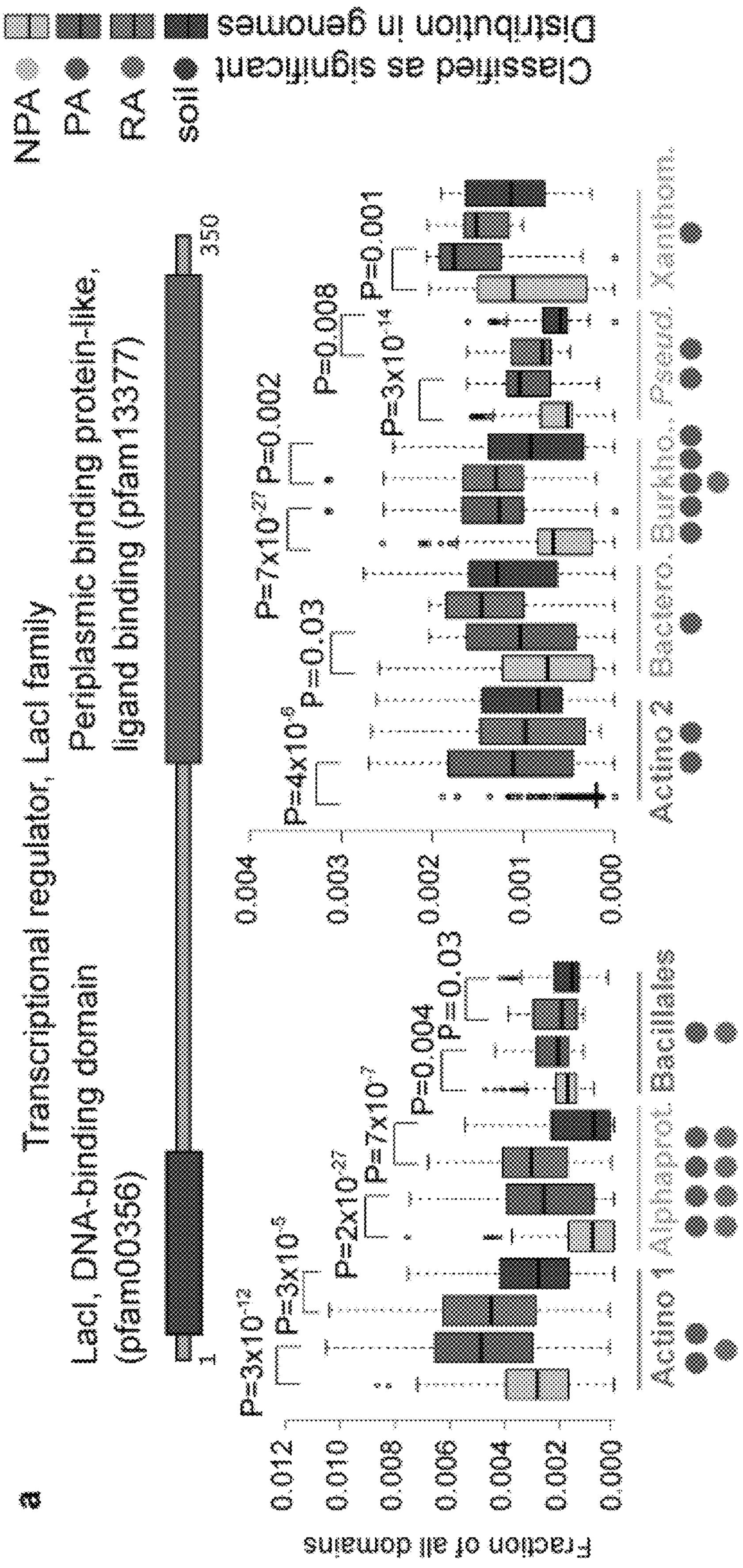
FIG. 3A. Proteins and protein domains that are reproducibly enriched as PA/RA in multiple taxa. Occurrence of protein domains (from Pfam) was compared between PA and NPA bacteria and between RA and soil bacteria. Taxon names are color coded by phyla as in FIGS. 1A and 1B. Transcription factors having LacI (Pfam00356) and periplasmic binding protein domains (Pfam13377). These proteins are often annotated as COG1609. Double panels are due to different scales. Actino.—Actinobacteria, Alphaprot.—Alphaproteobacteria, Bacil.—Bacillales, Burkholder.—Burkholderiales, Bactero.—Bacteroidetes, Pseud.—*Pseudomonas*, Xanthom.—Xanthomonadaceae. Box-and-whisker plots represent median, 25th and 75th percentiles, extreme data points that are within a 1.5 fold the interquartile range from the box, and outliers.

PA and RA proteins and protein domains conserved across evolutionarily diverse taxa are potentially pivotal to the interaction of bacteria with plants. 767 Pfam domains are identified that are significant PA domains in at least three taxa based on multiple tests. Two of these domains, a DNA binding (pfam00356) and a ligand binding (pfam13377) domain, are characteristic of the LacI transcription factor (TF) family. These TFs regulate gene expression in response to different sugars41 and their copy number is expanded in the genomes of PA and RA bacteria of eight of the nine taxa analyzed (FIG. 3A). Examination of the genomic neighbors of lacI family genes revealed a strong enrichment for genes involved in carbohydrate metabolism and transport in all of these taxa, consistent with their expected regulation by a LacI family member41. The promoter regions of these putative regulatory targets of LacI-family TFs are analyzed, and identified three AANCGNTT (SEQ ID NO:17) palindromic octamers that are statistically enriched in all but one taxon, and may serve as the TF binding site. These data suggest that accumulation of a large repertoire of LacI-family controlled regulons is a common strategy across bacterial lineages as they adapt to the plant environment.

Figure 3B:
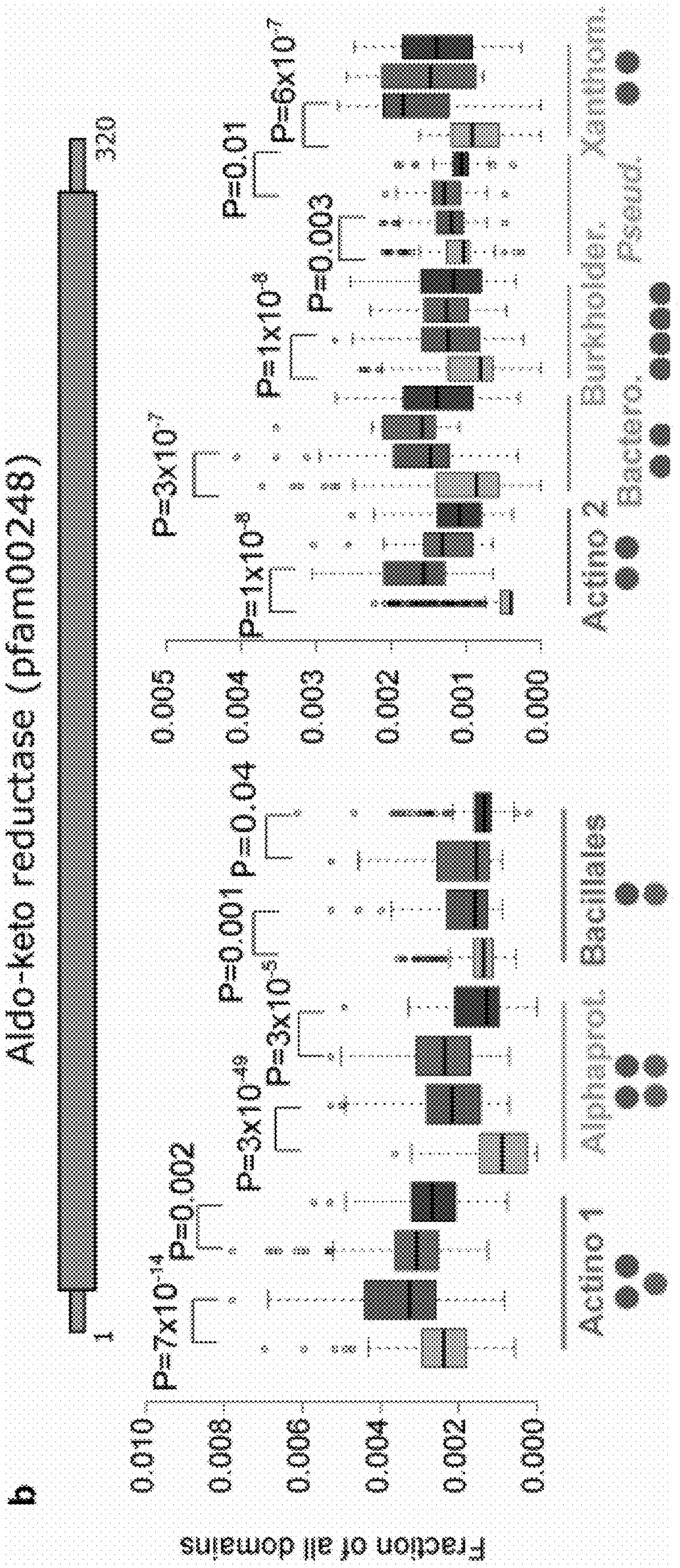
FIG. 3B. Proteins and protein domains that are reproducibly enriched as PA/RA in multiple taxa. Occurrence of protein domains (from Pfam) was compared between PA and NPA bacteria and between RA and soil bacteria. Taxon names are color coded by phyla as in FIGS. 1A and 1B. Aldo-keto reductase domain (Pfam00248). Proteins with this domain are often annotated as COG0667. A two-sided t-test was used for the presence of the genes between the genomes sharing the same label and was used to verify the enrichment reported by the various tests. FDR-corrected P values are indicated for significant results (q value <0.05). Filled circles denote the number of different statistical tests (maximum five) supporting a gene/domain being PA/NPA/RA/soil associated. Gene illustrations above each graph represent random protein models. Color coding of the different labels (PA etc.) is as in FIG. 1A. Double panels are due to different scales. Actino.—Actinobacteria, Alphaprot.—Alphaproteobacteria, Bacil.—Bacillales, Burkholder.—Burkholderiales, Bactero.—Bacteroidetes, Pseud.—*Pseudomonas*, Xanthom.—Xanthomonadaceae. Box-and-whisker plots represent median, 25th and 75th percentiles, extreme data points that are within a 1.5 fold the interquartile range from the box, and outliers.

Another domain, Aldo-keto reductase (pfam00248), is a metabolic domain enriched within the genomes of PA and RA bacteria from eight taxa belonging to all four phyla (FIG. 3B). This domain is involved in the metabolic conversion of a broad range of substrates, including sugars and toxic carbonyl compounds42. Thus, bacteria inhabiting the plant environment may consume similar substrates.

Putative Plant Protein Mimicry By PA and RA Proteins

Convergent evolution or horizontal transfer of protein domains from eukaryotes to bacteria have been suggested for some microbial effector proteins that are secreted into eukaryotic host cells to suppress defense and facilitate microbial proliferation43-45. New candidate effectors or other functional plant protein mimics are searched for. A set of significant PA/RA Pfam domains is retrieved that are reproducibly predicted by multiple approaches or in multiple taxa and cross-referenced these with protein domains that are also more abundant in plant genomes than in bacterial genomes. This analysis yields 64 Plant-Resembling PA and RA Domains (PREPARADOs) encoded by 11,916 genes. The number of PREPARADOs is four-fold higher than the number of domains that overlap with reproducible NPA/soil domains and plant domains (n=15). The PREPARADOs are relatively abundant in genomes of PA Bacteroidetes and Xanthomonadaceae (>0.5% of all domains on average). Some PREPARADOs are previously described as domains within effector proteins, such as Ankyrin repeats46, regulator of chromosome condensation repeat (RCC1)47, Leucine-rich repeat (LRR)48, and pectate lyase49. Intriguingly, PREPARADOs from plant genomes are enriched 3-14-fold ($P<10^{-5}$, Fisher exact test) as domains predicted to be 'integrated effector decoys' when fused to plant intracellular innate immune receptors of the NLR class50-53 (compared against two random domain sets). Surprisingly, 2201 bacterial proteins that encode 17/64 of the PREPARADOs share ≥40% identity across the entire protein sequence with eukaryotic proteins from plants, PA fungi or PA oomycetes, and therefore likely maintain a similar function. The patchy distribution among this class could have resulted from convergent evolution or from cross-kingdom HGT between phylogenetically distant organisms experiencing the shared selective forces of the plant environment.

Seven PREPARADO-containing protein families are characterized by N-terminal eukaryotic or bacterial signal peptides followed by a PREPARADO dedicated to carbohydrate binding or metabolism. One of these domains, Jacalin, is a mannose-binding lectin domain that is found in 48 genes in the *Arabidopsis thaliana* genome compared with three genes in the human genome25. Mannose is found on the cell wall of different bacterial and fungal pathogens and could serve as a microbial-associated molecular pattern (MAMP) that is recognized by the plant immune system54-

Figure 4:
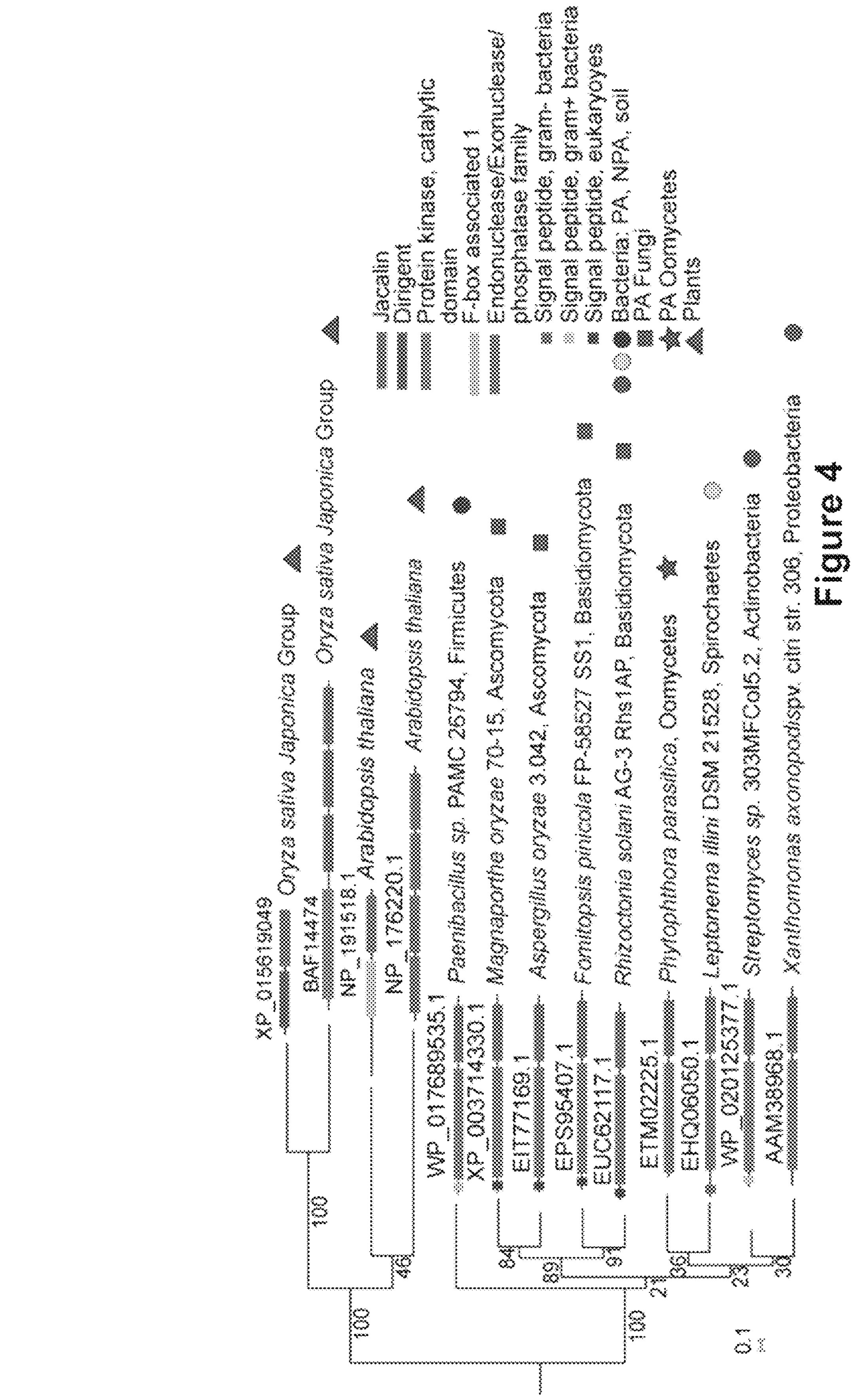
FIG. 4. A protein family shared by PA bacteria, fungi, and oomycetes that resemble plant proteins. Maximum likelihood phylogenetic tree of representative proteins with Jacalin-like domains across plants and PA organisms. Endonuclease/exonuclease/phosphatase (EEP)-Jacalin proteins are present across PA eukaryotes (fungi and oomycetes) and PA bacteria. In most cases these proteins contain a signal peptide in the N-terminus. The Jacalin-like domain is found in many plant proteins, often in multiple copies. Protein accession appears above each protein illustration.

61. A family of ~430 AA long microbial proteins is identified with a signal peptide, followed by a functionally ill-defined endonuclease/exonuclease/phosphatase family domain (pfam03372) and ending with a Jacalin domain (pfam01419). Strikingly, this domain architecture is absent in plants but is distributed across diverse microorganisms, many of which are phytopathogens, including Gram-negative and -positive bacteria, fungi from the Ascomycota and Basidiomycota phyla, and oomycetes (FIG. 4). These microbial lectins may be secreted to outcompete plant immune receptors for mannose binding on the microbial cell wall, effectively serving as camouflage.

To conclude, a large set of protein domains is discovered that are shared between plants and the microbes colonizing them. In many cases the entire protein is conserved across evolutionarily distant PA microorganisms.

Co-Occurrence of PA Gene Clusters

Figure 5A:
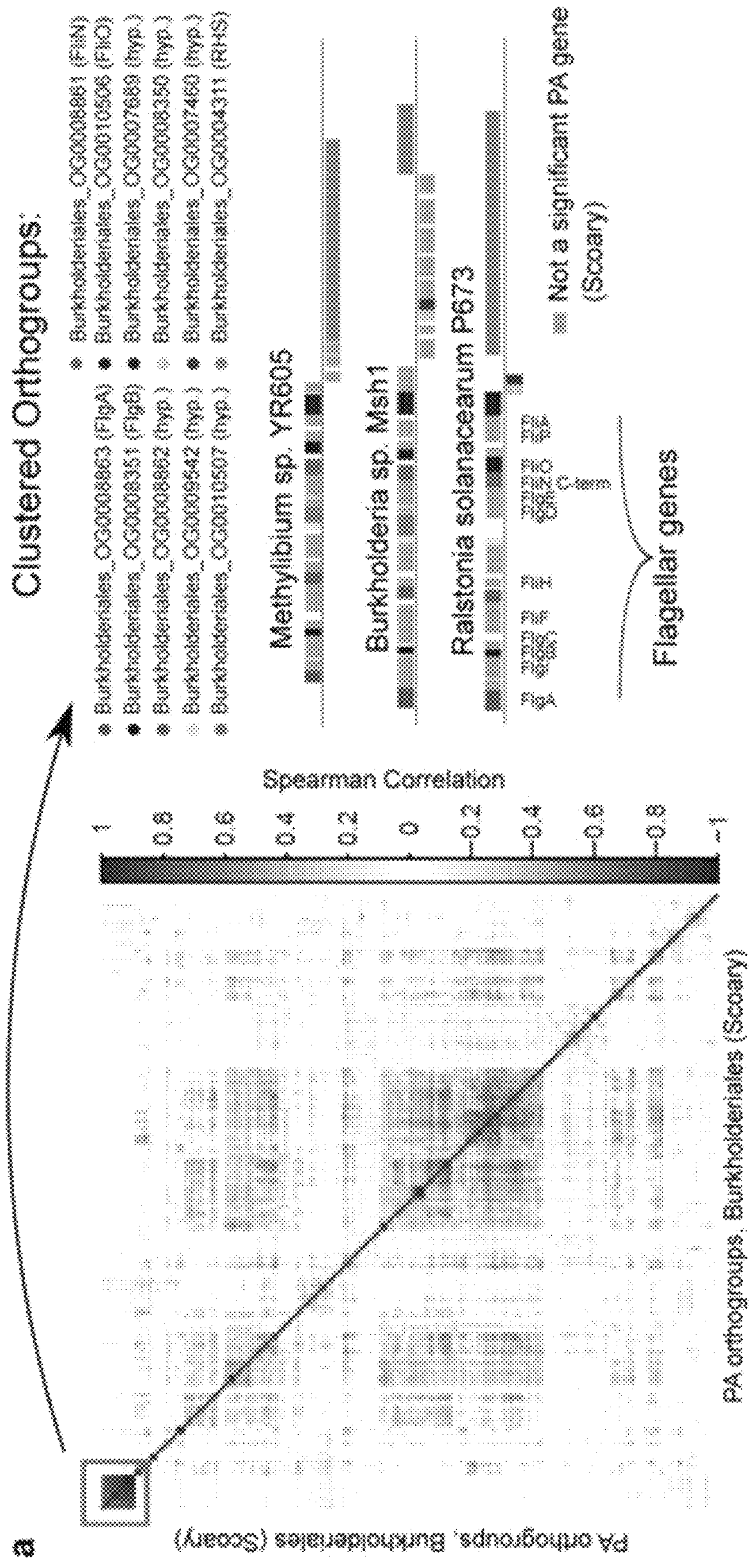
FIG. 5A. Co-occurring PA/soil flagellum-like gene cluster is sporadically distributed across Burkholderiales. Left panel: A hierarchically clustered correlation matrix of all 202 significant PA orthogroups (gene clusters) from Burkholderiales, predicted by Scoary. Right panel: the orthogroups are presented within and adjacent to the flagellar-like locus of different genomes. Gene names based on blast search appears in parentheses. hyp.—a hypothetical protein, RHS—RHS repeat protein. Genes illustrated above and below line are located on the positive and negative strand, respectively. Pillars of filled circles represent the 11 orthogroups. Genus names are shown next to each pillar.
Figure 5B:
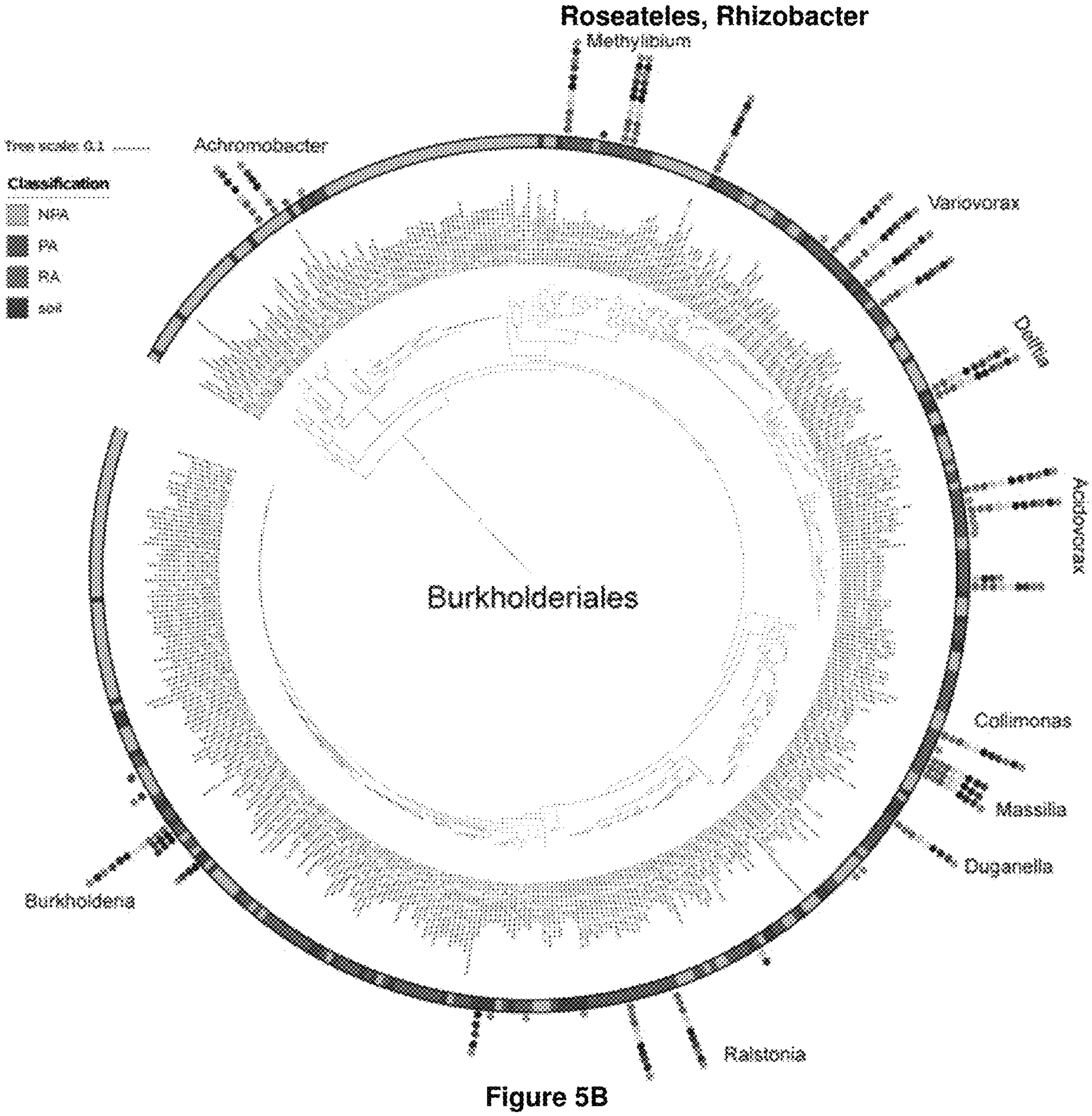
FIG. 5B. Co-occurring PA/soil flagellum-like gene cluster is sporadically distributed across Burkholderiales. The Burkholderiales phylogenetic tree based on the concatenated alignment of 31 single copy genes. Pillars of filled circles represent the 11 orthogroups, using the same color coding as in FIG. 5A. Genus names are shown next to each pillar.

Numerous cases of PA gene clusters (orthogroups) are identified that demonstrate high co-occurrence between genomes. When the PA genes are derived from phylogeny-aware tests (i.e. PhyloGLM and Scoary) they are candidates for inter-taxon HGT events. For example, a cluster predicted by Scoary of up to 11 co-occurring genes (mean pairwise Spearman correlation=0.81) is identified in a flagellum-like locus from sporadically distributed PA/soil genomes across 12 different genera in Burkholderiales (FIGS. 5A and 5B). Two of the annotated flagellar-like proteins, FlgB (COG1815) and FliN (pfam01052), are also PA genes in Actinobacterial and Alphaproteobacteria taxa. Six of the remaining genes encode hypothetical proteins, all but one of which are specific to Betaproteobacteria, suggestive of a flagellar structure variant that evolved in this class in the plant environment. Flagellum-mediated motility or flagellum-derived secretion systems (e.g. T3SS) are important for plant colonization and virulence39,40,62,63 and can be horizontally transferred64.

Novel Putative PA and RA Gene Operons

Figure 6A:
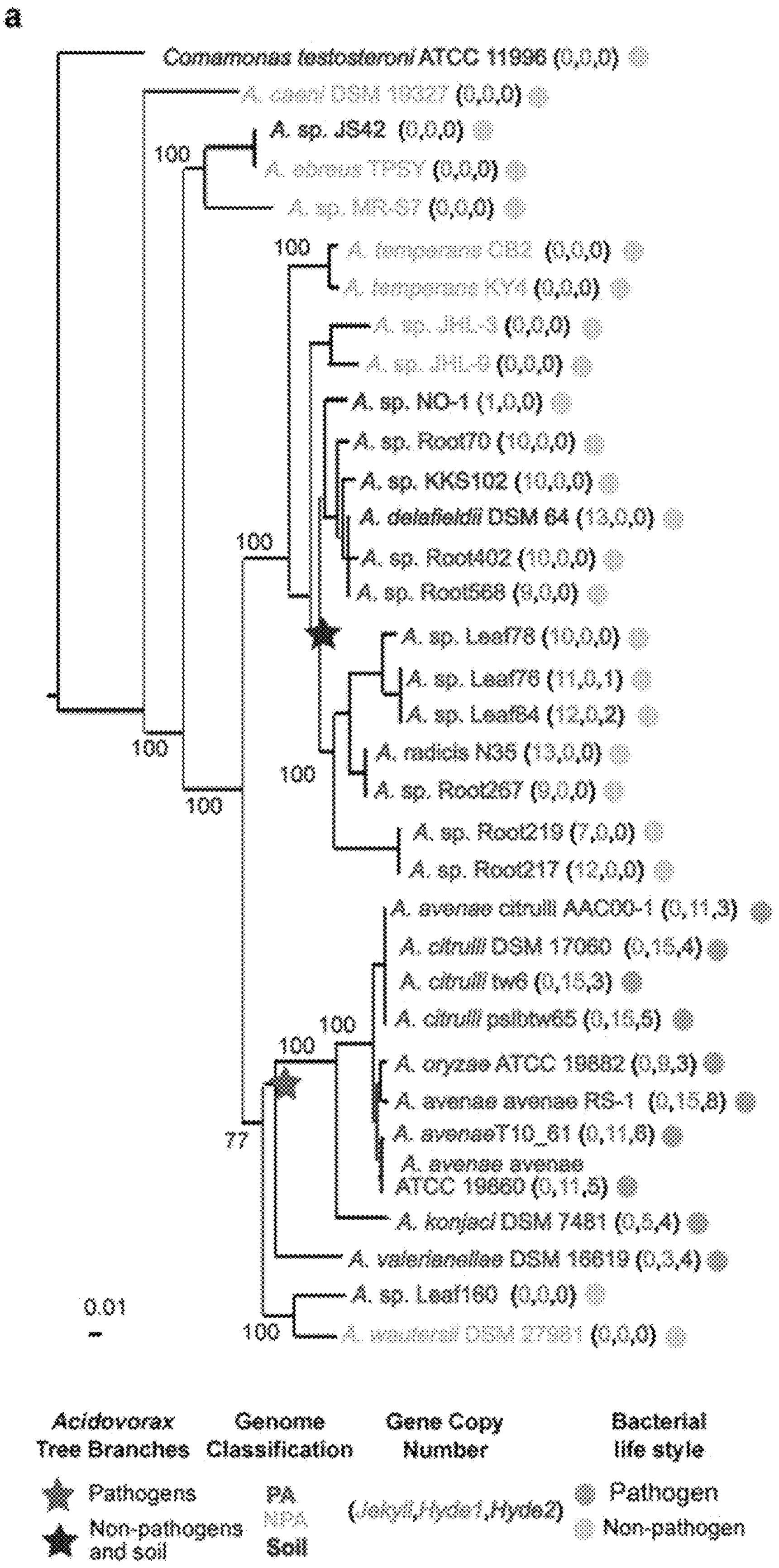
FIG. 6A. Rapidly diversifying, high copy-number Jekyll and Hyde PA genes. Maximum likelihood phylogenetic tree of *Acidovorax* isolates based on concatenation of 35 single-copy genes. The pathogenic and non-pathogenic branches of the tree are perfectly correlated with the presence of Hyde1 and Jekyll genes, respectively.

In addition to successfully capturing several known PA operons (FIGS. 2C to 2I), additional putative PA bacterial operons are also identified. Two previously uncharacterized PA gene families are conspicuous. The genes are organized in multiple loci in PA genomes, each of up to five tandem gene copies. They encode short, highly divergent and high copy number proteins which are predicted to be secreted. Strikingly, these two PA protein families never co-occur in the same genome and their genomic presence is perfectly correlated with pathogenic or non-pathogenic bacterial lifestyles of the genus *Acidovorax* (order Burkholderiales) (FIG. 6A). The gene families Jekyll and Hyde are named for those present in non-pathogens and pathogens, respectively.

Figure 6B:
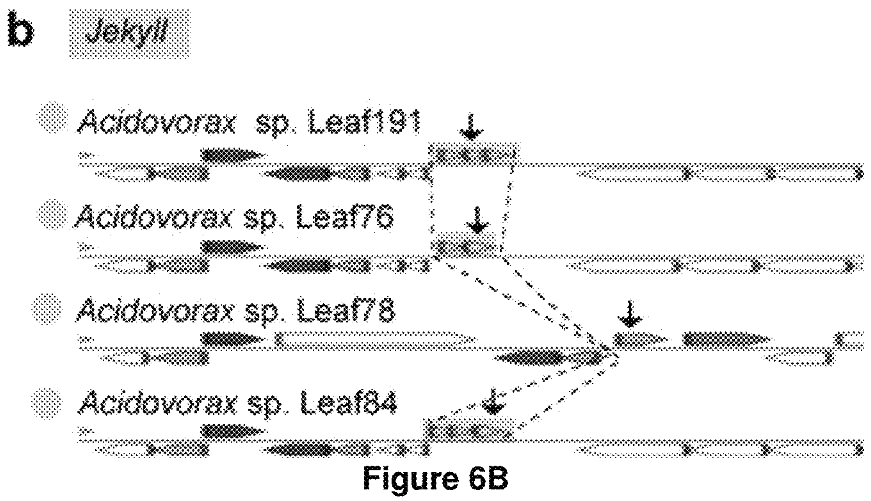
FIG. 6B. Rapidly diversifying, high copy-number Jekyll and Hyde PA genes. An example of a variable Jekyll locus in highly related *Acidovorax* species isolated from leaves of wild *Arabidopsis* from Brugg, Switzerland. Arrows denote the following locus tags (from top to bottom): Ga0102403_10161, Ga0102306_101276, Ga0102307_107159, Ga0102310_10161.

The typical Jekyll gene is 97 AAs long, contains an N-terminal signal peptide, lacks a transmembrane domain, and in 98.5% of cases appears in non-pathogenic PA or soil-associated *Acidovorax* isolates (FIG. 6A). A single genome may encode up to 13 Jekyll gene copies (FIG. 6A) distributed in up to nine loci. Four *Acidovorax* strains are isolated from the leaves of naturally grown *Arabidopsis*16. Even these nearly identical isolates carry hypervariable Jekyll loci that are substantially more divergent than neighboring genes and include copy number variations and various mutations (FIG. 6B).

Figure 6C:
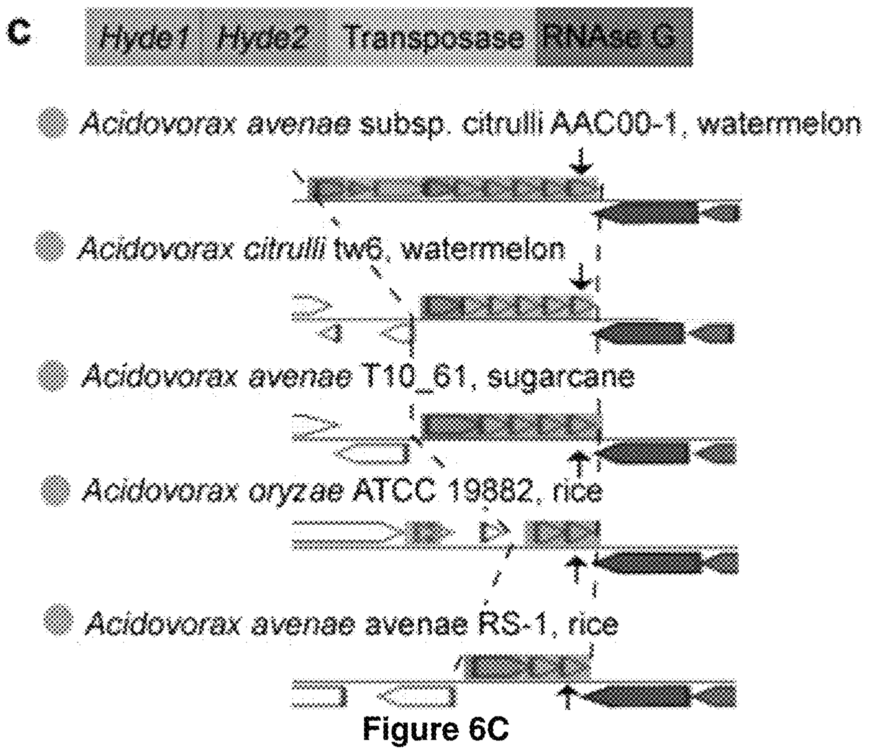
FIG. 6C. Rapidly diversifying, high copy-number Jekyll and Hyde PA genes. An example of a variable Hyde locus from pathogenic *Acidovorax* infecting different plants (host plant appears after species name). The transposase in the first operon fragmented a Hyde2 gene. Arrows denote the following locus tags (from top to bottom): Aave_3195, Ga0078621_123525, Ga0098809_1087148, T336DRAFT_00345, AASARDRAFT_03920.
Figure 6D:
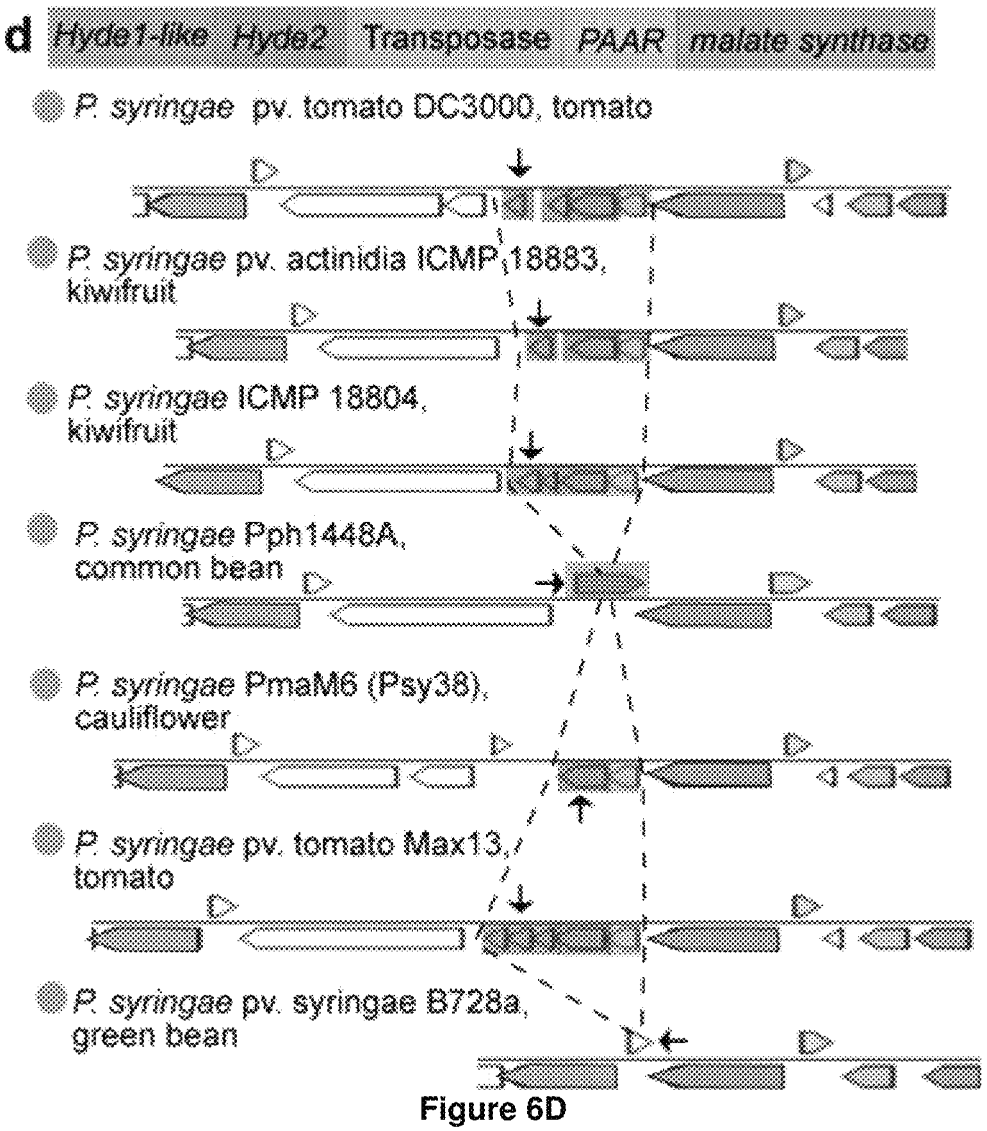
FIG. 6D. Rapidly diversifying, high copy-number Jekyll and Hyde PA genes. An example of a variable Hyde locus from pathogenic *Pseudomonas syringae* infecting different plants. Arrows denote the following locus tags (from top to bottom): PSPTOimg_00004880 (a.k.a PSPTO_0475), A243_06583, NZ4DRAFT_02530, Pphimg_00049570, PmaM6_0066.00000100, PsyrptM_010100007142, Psyr_4701. Genes colored using the same colors in B-D are homologous with the exception of genes colored in ivory (unannotated genes) and Hyde1 and Hyde1-like genes which are analogous by similar size, high diversification rate, position downstream to Hyde2, and a tendency for having a transmembrane domain. PAAR—proline-alanine-alanine-arginine repeat superfamily.

The Hyde putative operons, on the other hand, are composed of two distinct gene families unrelated to Jekyll. A typical Hyde1 protein has 135 AAs and an N-terminal transmembrane helix. Hyde1 proteins are also highly variable as measured by copy number variation, sequence divergence and intra-locus transposon insertions (FIGS. 6A and 6C). Hyde1 is found in 99% of cases in phytopathogenic *Acidovorax*. These genomes carry up to 15 Hyde1 gene copies distributed in up to ten loci (FIG. 6A). In 70% of cases Hyde1 is located directly downstream from a more conserved ~300 AA long PA protein-coding gene that is named Hyde2 (FIGS. 6C and 6D). Loci with Hyde2 followed by Hyde1-like genes are identified in different Proteobacteria. These contain a highly variable Hyde1-like family that only maintains its short length and a transmembrane helix. Hyde-encoding organisms include other phytopathogens, such as *Pseudomonas syringae*, where the Hyde1-like-Hyde2 locus is again highly variable between closely related strains (FIG. 6D). However, the striking Hyde genomic expansion is specific to the phytopathogenic *Acidovorax* lineage. Notably, Hyde genes are often directly preceded by genes encoding core structural T6SS proteins, such as PAAR, VgrG, and Hcp65, or fused to PAAR (FIG. 6D). Hyde1 and/or Hyde2 might constitute a new T6SS effector family.

Figure 7A:
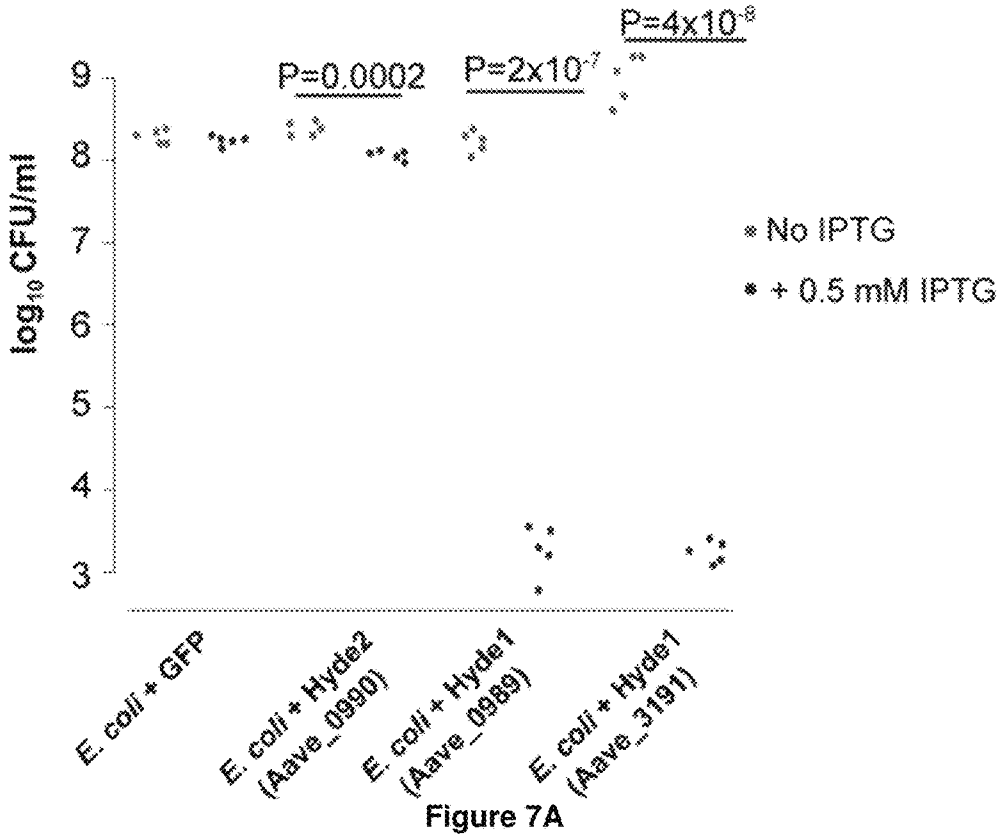
FIG. 7A. Hyde1 proteins of *Acidovorax citrulli* AAC00-1 are toxic to *E. coli* and various PA bacterial strains. Toxicity assay of Hyde proteins expressed in *E. coli*. GFP, Hyde2—Aave_0990, and two Hyde1 genes from two loci, Aave_0989 and Aave_3191, were cloned into pET28b and transformed into *E. coli* C41 cells. Aave_0989 and Aave_3191 proteins are 53% identical. Bacterial cultures from five independent colonies were spotted on LB plate. Gene expression of the cloned genes was induced using 0.5 mM IPTG. P values indicate significant results (two sided t-test).
Figure 7B:
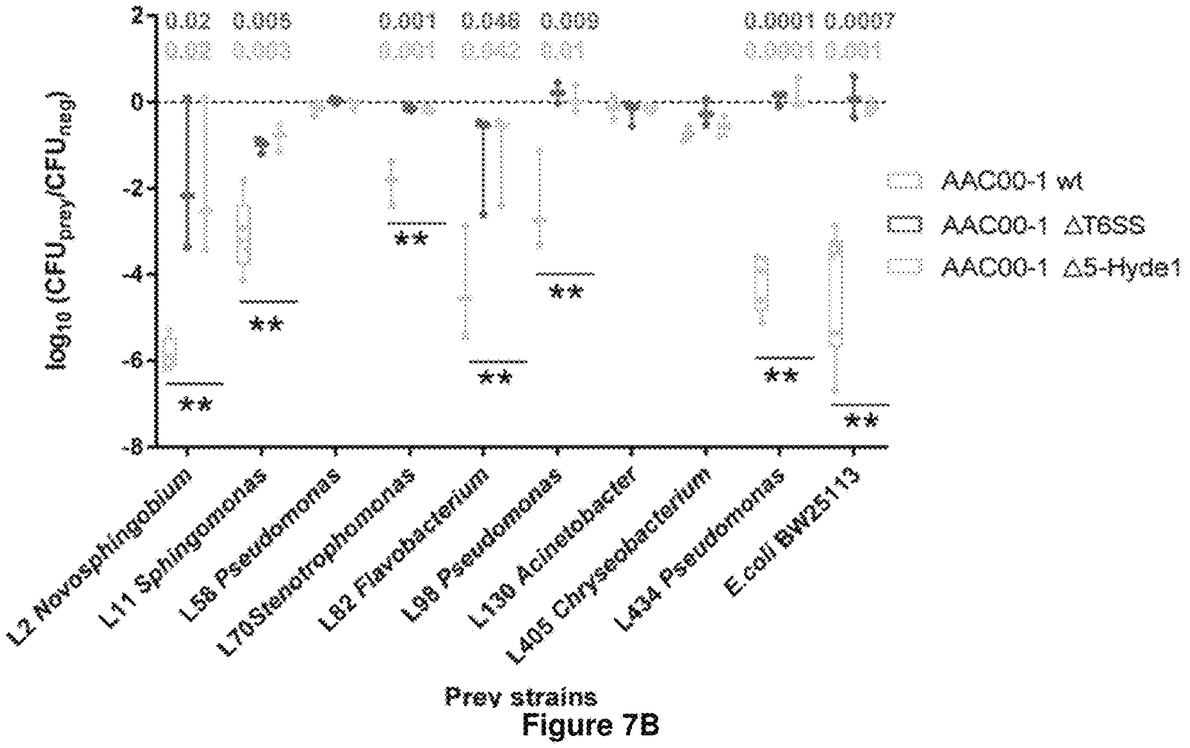
FIG. 7B. Hyde1 proteins of *Acidovorax citrulli* AAC00-1 are toxic to *E. coli* and various PA bacterial strains. Quantification of recovered prey cells after co-incubation with *Acidovorax* aggressor strains. Antibiotic-resistant prey strains *E. coli* BW25113 and nine different *Arabidopsis* leaf isolates were mixed at equal ratios with different aggressor strains or with NB medium (negative control). Δ5-Hyde1 contains deletion of five Hyde1 loci (including nine out of 11 Hyde1 genes). ΔT6SS contains a vasD (Aave_1470) deletion. After co-incubation for 19 hours on NB agar plates, mixed populations were resuspended in NB medium and spotted on selective antibiotic-containing NB agar. Box plots of at least three independent experiments with individual values superimposed as dots are shown. Double asterisks denote a significant difference (one-way ANOVA followed by Tukey's HSD test) between wild type vs. ΔT6SS, and wild type vs. Δ5-Hyde1, with P values denoted on top.

The elevated sequence diversity of Jekyll and Hyde1 genes suggests that these two PA protein families could be involved in molecular arms races with other organisms within the plant environment. Since many type VI effectors are used in inter-bacterial warfare, *Acidovorax* Hyde1 proteins are tested for antibacterial properties. Expression of two variants of the gene in *E. coli* led to 105-106 fold reduction in cell numbers (FIG. 7A). A mutant is constructed deleted for five Hyde1 loci (Δ5-Hyde1; encompassing 9/11 Hyde1 genes) in the phytopathogen *Acidovorax citrulli* AAC00-1. Wild type (WT), Δ5-Hyde1, and T6SS mutant (ΔT6SS) *Acidovorax* strains are co-incubated with an *E. coli* strain that is susceptible to T6SS killing66 and nine phylogenetically diverse *Arabidopsis* leaf bacterial isolates16. Remarkably, survival of wild type *E. coli* and six of the leaf isolates after co-incubation with WT *Acidovorax* is reduced 102-106-fold compared to their co-incubation with Δ5-Hyde1 or ΔT6SS *Acidovorax* (FIG. 7B). Combined with the genomic association of Hyde loci with T6SS, these results suggest that the T6SS antibacterial phenotype of *Acidovorax* is mediated by Hyde proteins and that these toxins are used in competition against other PA organisms. Consistent with a function in microbe-microbe interactions, compromised virulence of Δ5-Hyde1 strain on host plants (watermelon) is did not detect. However, clearing competitors via T6SS can aid in the persistence of *Acidovorax citrulli* on its host67.

Discussion

There is increasing awareness that plant-associated microbial communities play important roles in host growth and health. An understanding of plant-microbe relationships at the genomic level could enable enhancement of agricultural productivity using microbes. Most studies have focused on specific plant microbiomes, with more emphasis on microbial diversity than on gene function12,14,16,18,68-74. Nearly 500 RA bacterial genomes isolated from different plant hosts are sequenced. These new genomes are combined in a collection of 3837 high quality bacterial genomes for comparative analysis. A systematic approach is developed to identify PA and RA genes and putative operons. This method is accurate as reflected by the ability to capture numerous operons previously shown to have a PA function, the enrichment of PA genes in PA metagenomes, the validation of Hyde1 proteins as likely type VI effectors in *Acidovorax* directed against other PA bacteria, and the validation of two new genes in *Paraburkholderia kururiensis* that affect rice root colonization. Bacterial genes that are enriched in genomes from the plant environment are also likely to play a role in adaptation to the many other organisms that share the same niche, as demonstrated for Hyde1.

Five different statistical approaches are used to identify genes significantly associated with the plant/root environment, each with its advantages and disadvantages. The phylogeny-correcting approaches (phyloglmbin, phyloglmcn, and Scoary) allow accurate identification of genes that are polyphyletic and correlate with an environment independently of ancestral state. Based on metagenome validation, the hypergeometric test predicts more genes that are abundant in plant-associated communities than Phyloglm. It also enables identification of monophyletic PA genes but yields more false positives than the phylogenetic tests since in every PA lineage, many lineage-specific genes will be considered PA. Scoary is the most stringent method of all and yields the lowest number of predictions. Future experimental validation should prioritize genes predicted in multiple taxa and/or by multiple approaches.

64 PREPARADOs are discovered. Proteins containing 19 of these domains are predicted to be secreted by Sec or T3SS. Notably, plant proteins carrying 35 of these domains belong to the NLR class of intracellular innate immune receptors. Hence, these PREPARADO protein domains may serve as molecular mimics. Some may interfere with plant immune functions through disruption of key plant protein interactions75,76. Likewise the Jacalin-containing proteins in PA bacteria, fungi and oomycetes may represent a strategy of avoiding MAMP-triggered immunity by binding to extracellular microbial mannose molecules, thereby serving as a molecular invisibility cloak77,78.

Finally, it is demonstrated that numerous PA functions are surprisingly consistent across phylogenetically-diverse bacterial taxa and that some functions are even shared with PA eukaryotes. Some of these traits may facilitate plant colonization by microbes and therefore might prove useful in genome engineering of agricultural inoculants to eventually yield a more efficient and sustainable agriculture.

Figure 9A:
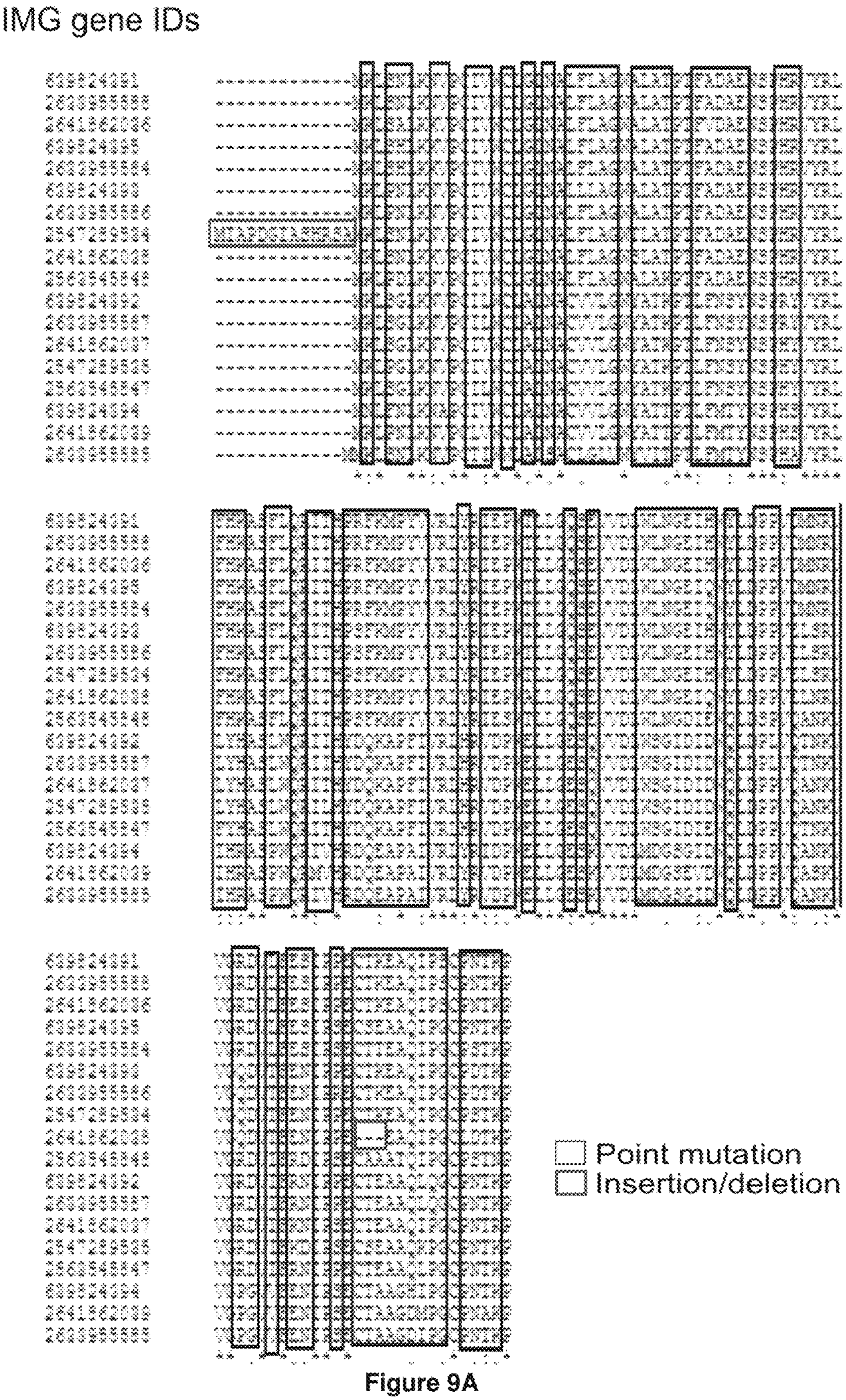
FIG. 9A. Hyde genes variability and protein motifs. Multiple sequence alignment by MAFFT of the Hyde1 proteins presented in FIG. 6C. The sequences are: 639824391(SEQ ID NO:1), 2633955568 (SEQ ID NO:27), 2641862036 (SEQ ID NO:28), 639824395(SEQ ID NO:5), 2633955584 (SEQ ID NO:29), 639824393(SEQ ID NO:3), 2633955586 (SEQ IDNO:30), 2547289534 (SEQ ID NO:31), 2641862038 (SEQ ID NO:32), 2563545848 (SEQ ID NO:33), 639824392(SEQ ID NO:2), 2633955587 (SEQ ID NO:34), 2641862037 (SEQ ID NO:35), 2547289535 (SEQ ID NO:36), 2563545847 (SEQ ID NO:37), 639824394(SEQ ID NO:4), 2641862035 (SEQ ID NO:38), 2633955585 (SEQ ID NO:39).
Figure 9B:
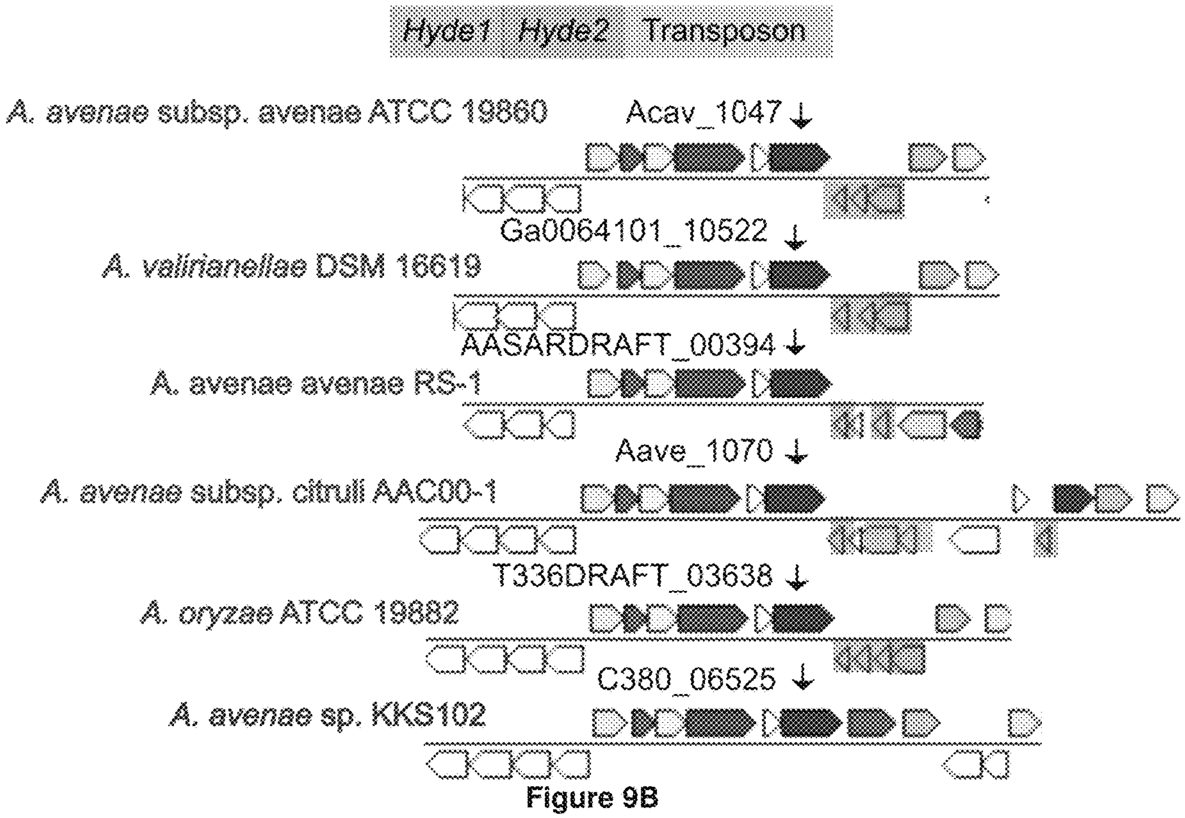
FIG. 9B. Hyde genes variability and protein motifs. A variable Hyde locus. Note the absence of the locus from the last soil-associated isolate despite the conservation of the genomic environment.
Figure 9C:
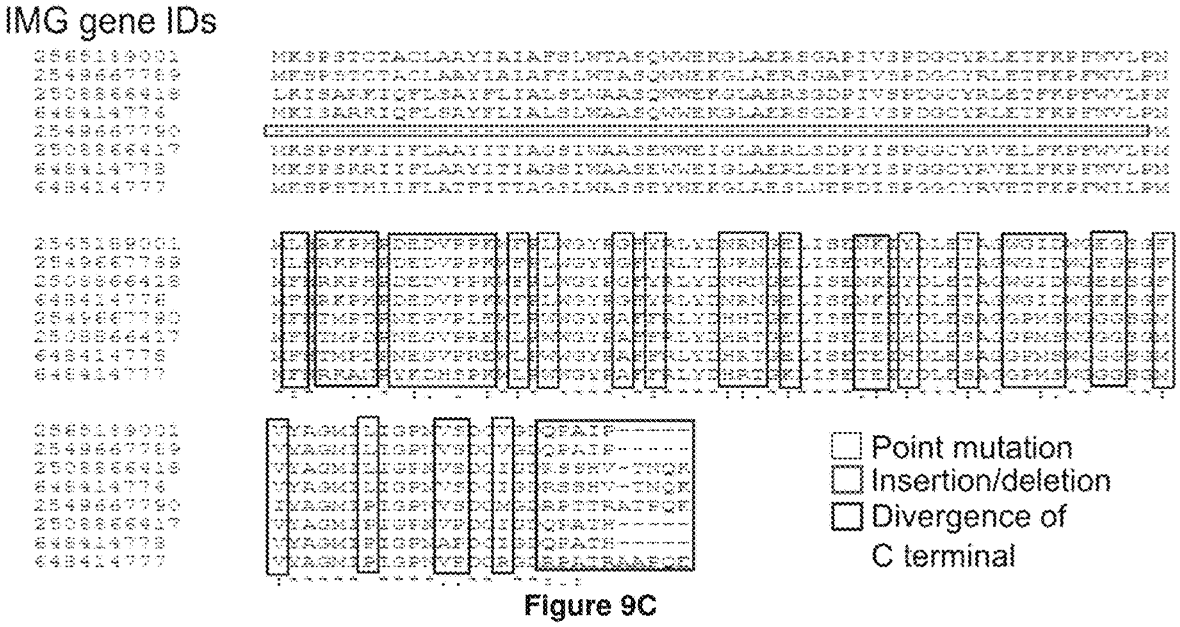
FIG. 9C. Hyde genes variability and protein motifs. Multiple sequence alignment by MAFFT of the Hyde1 proteins presented in FIG. 9B. The sequences are: 2565189001 (SEQ ID NO:40), 2549667789 (SEQ ID NO:41), 2508866418 (SEQ ID NO:42), 648414776 (SEQ ID NO:43), 2549667790 (SEQ ID NO:44), 2508866417 (SEQ ID NO:45), 648414778 (SEQ ID NO:46), and 648414777 (SEQ ID NO:47).
Figure 10A:
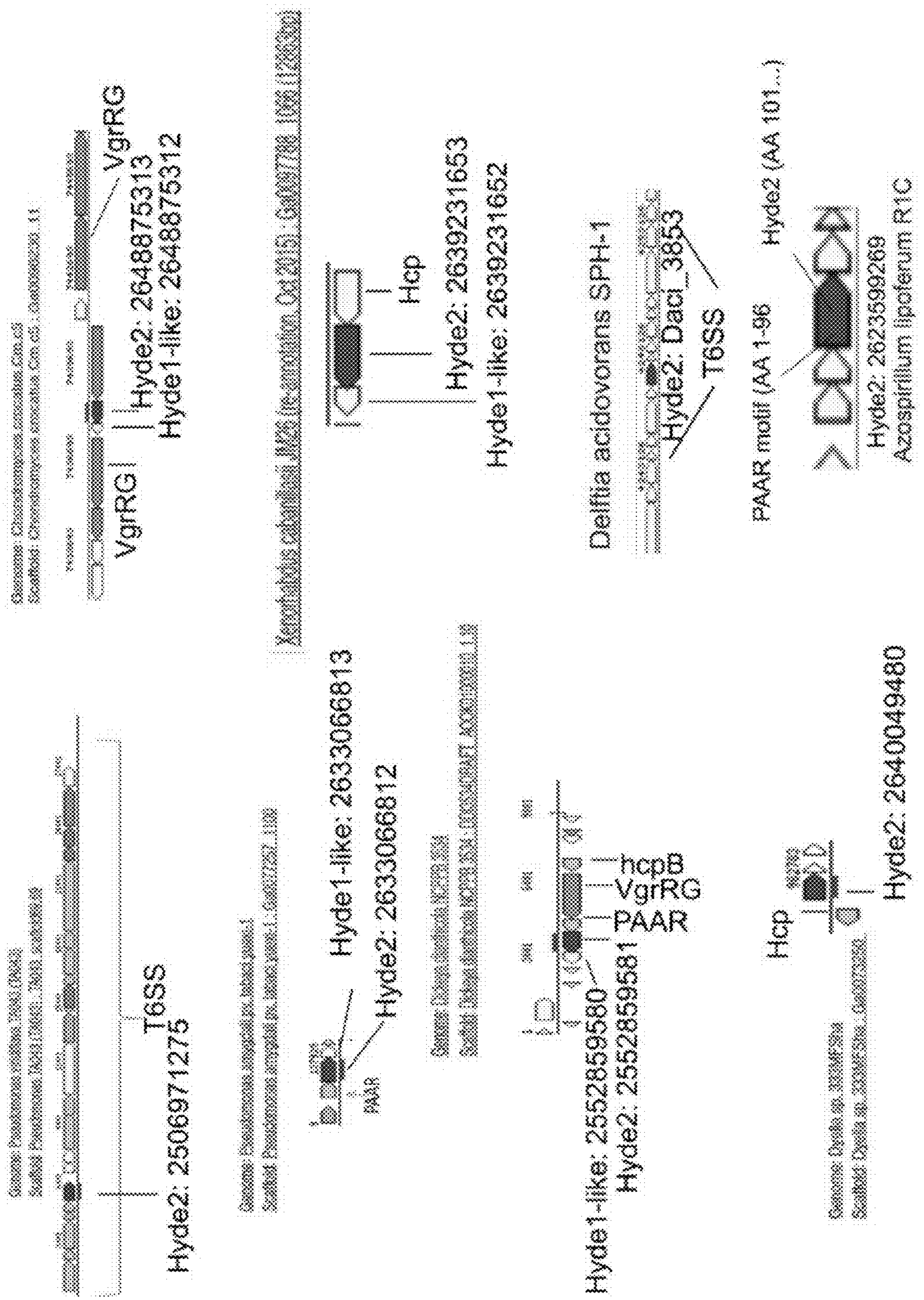
FIG. 10A. Association between Hyde loci and T6SS. Genomic proximity between different Hyde2 proteins (marked in red, number represent IMG gene number) and different T6SS components and a fusion event between Hyde2 and PAAR domain in *Azospirilium*. AA—amino acids.
Figure 10B:
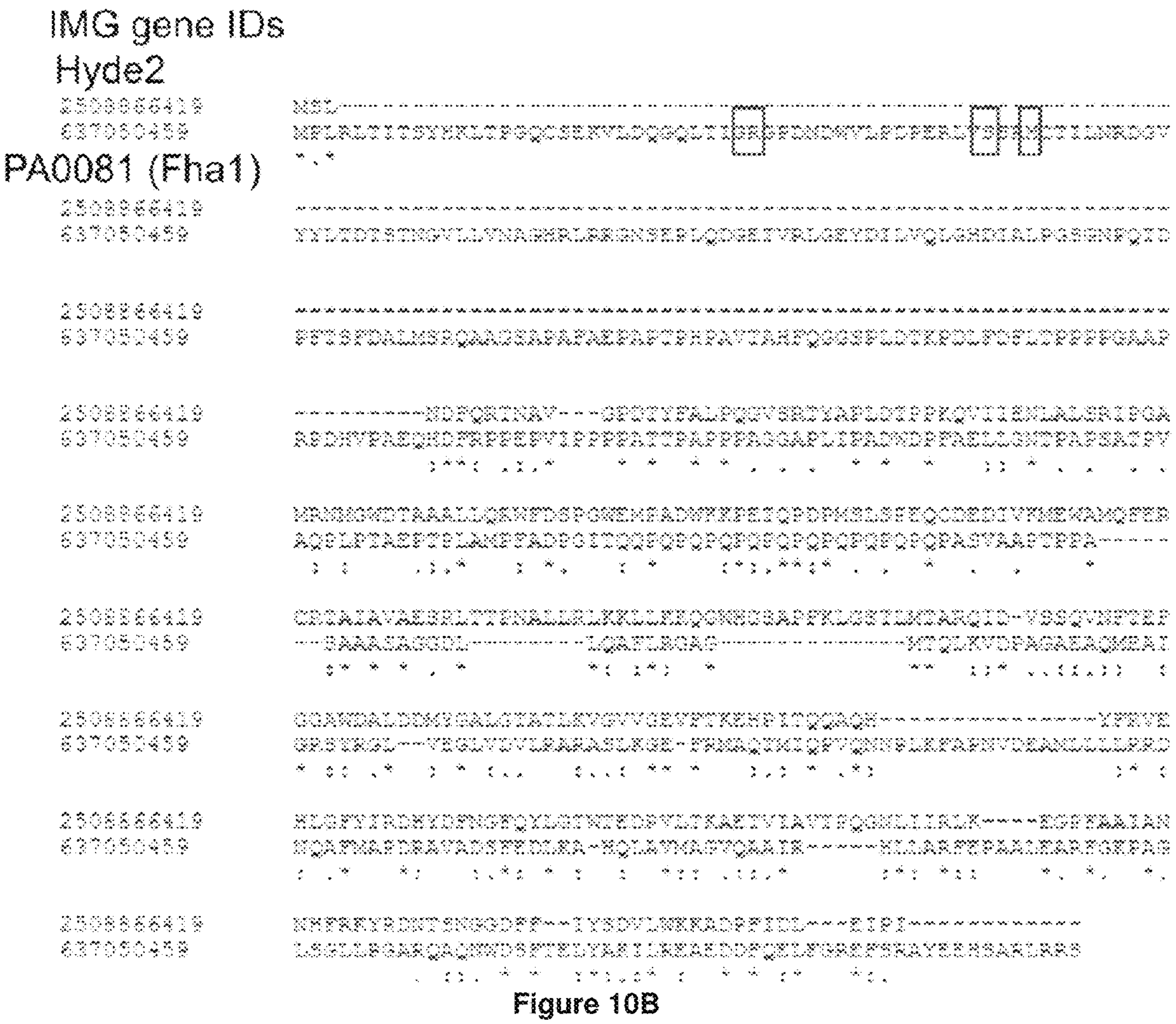
FIG. 10B. Association between Hyde loci and T6SS. Similarity between Hyde2 protein of *Pseudomonas syringae* pv. tomato DC3000 (DC3000 gold standard) (2508866419; SEQ ID NO:47) and FHA1 protein—a core scaffolding protein of the *P. aeruginosa* H-T6SS (637050459; SEQ ID NO:48) that is required for protein secretion by T6SS[36]. The amino acids marked in red are phosphopeptide binding motif. Hyde2 is shorter than the FHA protein and lacks the FHA domain (pfam00498).

FIGS. 9A to 9C show Hyde genes variability and protein motifs. FIGS. 10A and 10B show association between Hyde loci and T6SS.

Bacterial Isolation and Genome Sequencing

Bacterial strains from Brassicaceae and Poplar are isolated using previously described protocols79,80. Poplar strains are cultured from root tissues collected from *Populus deltoides* and *Populus trichocarpa* trees in Tennessee, North Carolina, and Oregon. Root samples are processed as described previously15,81. Briefly, rhizosphere strains are isolated by plating serial dilutions of root wash, while for endosphere strains, surface sterilized roots are pulverized with a sterile mortar and pestle in 10 mL of MgSO4 (10 mM) solution followed by plating serial dilutions. Strains are isolated on R2A agar media, and resulting colonies are picked and re-streaked a minimum of three times to ensure isolation. Isolated strains are identified by 16S rDNA PCR followed by Sanger sequencing.

For maize isolates, soils associated with Il14h and Mo17 maize genotypes grown in Lansing, NY and Urbana, Il. The rhizosphere soil samples of each maize genotype are grown at each location and are collected at week 12 as previously described68. From each rhizosphere soil sample, soil is washed and samples are plated onto *Pseudomonas* Isolation Agar (BD Diagnostic Systems). The plates are incubated at 30° C. until colonies formed and DNA is extracted from cells.

For isolation of single cells, *A. thaliana* accessions Col-0 and Cvi-0 are grown to maturity. Roots are washed in distilled water multiple times. Root surfaces are sterilized using bleach. Surfaced sterilized roots are then ground using a sterile mortar and pestle. Individual cells are isolated using FACS followed by DNA amplification using MDA, and 16S rDNA screening as described previously82.

DNA from isolates and single cells is sequenced using NGS platforms, mostly using the Illumina HiSeq technology. Sequenced genomic DNA is assembled using different assembly methods. Genomes are annotated using the DOE-JGI Microbial Genome Annotation Pipeline (MGAP v.4)23 and are deposited at the IMG database83, ENA or Genbank for public usage.

Data Compilation of 3837 Isolate Genomes and Their Isolation Sites Metadata 5586 bacterial genomes are retrieved from the IMG system. Isolation sites are identified through a manual curation process that included scanning of IMG metadata, DSMZ, ATCC, NCBI Biosample, and the scientific literature. Based on its isolation site, each genome is labeled as one of PA, NPA, or soil. PA organisms are also labeled as RA when isolated from the EC or from the rhizoplane. A stringent quality control is applied to ensure a high quality and minimally biased set of genomes:

a. Known isolation site—genomes with missing isolation site information are filtered out.

b. High genome quality and completeness—all isolate genomes pass this filter if N50 was larger than 50,000 bp. Single amplified genomes pass the quality filter if they had at least 90% of 35 universal single copy COGs84. In addition, CheckM85 is used to assess isolate genome completeness and contamination. Only genomes that are at least 95% complete and no more than 5% contaminated are used.

c. High quality gene annotation—genomes that pass this filter had at least 90% of genome sequence coding for genes with an exceptions: in *Bartonella* genus most genomes have coding base percentages below 90%.

d. Non-redundancy—whole genome with average nucleotide identity (gANI) and alignment fraction (AF) values for each pair of genomes86. When AF exceeded 90% and gANI is higher than 99.995%, the genome pair redundant. In such cases one genome is randomly selected and the other genome is marked as "redundant" and is filtered out.

e. Consistency in the phylogenetic tree—14 bacterial genomes are filtered out that show discrepancy between their given taxonomy and their actual phylogenetic placement in the bacterial tree.

Bacterial Genome Tree Construction

To generate a bacterial phylogenetic tree of the 3837 high-quality and non-redundant genomes, 31 universal single copy genes from each genome are retrieved using AMPHORA287. For each individual marker gene an alignment is constructed using Muscle with default parameters. The 31 alignments are masked using Zorro88 and filtered the low quality columns of the alignment. Finally, the 31 alignments are concatenated into an overall merged alignment from which an approximately-maximum-likelihood phylogenetic tree is built using the WAG model implemented in FastTree 2.189.

Clustering of 3837 Genomes Into Nine Taxa

The dataset is divided into different taxa (taxonomic groups) in order to allow downstream identification of genes enriched in the PA or RA genomes of each taxon over the NPA or soil genomes from the same taxon, respectively. In order to determine the number of taxonomic groups to analyze, the phylogenetic tree is converted into a distance matrix using the cophenetic function implemented in the R package ape. The 3837 genomes are clustered into 9 groups using k-medoids clustering as implemented in the partitioning around medoids (PAM) algorithm from the R package fpc. k-medoids clusters a data set of n objects into k a priori defined clusters. In order to identify the optimal k for the dataset, the silhouette coefficient for values of k ranging from 1 to 30 is compared. A value of k=9 is selected as it yielded the maximal average silhouette coefficient (0.66). In addition, when using a k=9 the taxa are monophyletic, contained hundreds of genomes, and are relatively balanced between PA and NPA genomes in most taxa (Table 1). The resulting genome clusters generally overlap with annotated taxonomic units. One exception is in the Actinobacteria phylum. The clustering divide the genomes into two taxa that named “Actinobacteria 1” and “Actinobacteria 2”. However, this rigorous phylogenetic analysis supports previous suggestions for revisions in the taxonomy of phylum Actinobacteria90.

In addition, the tree revealed very divergent bacterial taxa in the Bacteroidetes phylum that cannot be separated into monophyletic groups. Specifically, the Sphingobacteriales order (from Class Sphingobacteria) and the Cytophagaceae (from class Cytophagia) are paraphyletic. Therefore, all Bacteroidetes are unified into one phylum-level taxon.

Identification of PA, NPA, RA and Soil Genes/Domains

The following description applies to PA, NPA, RA, and soil genes. PA genes are identified using a two-step process that includes protein/domain clustering based on AA sequence similarity and subsequent identification of the protein/domain clusters significantly enriched in protein/domains from PA bacteria. Clustering of genes and protein domains involved five independent methods: Orthofinder24, COG20, Kegg orthology (KO)21, TIGRFAM22, and Pfam25. Orthofinder is selected (following the aforementioned benchmarking) as a clustering approach that included all proteins, including those that lack any functional annotation. First, each taxon is compiled separately, a list of all proteins in the genomes. For COG, KO, TOGRFAM, and Pfam, the existing annotations of IMG genes is used that are based on blast alignments to the different protein/domain models23. This process yielded gene/domain clusters. Next, clusters are tested that are significantly enriched with genes derived from PA genomes. These clusters are termed ‘PA clusters’. In the statistical analysis, only clusters of more than five members are used. P values are corrected with Benjamini-Hochberg FDR and use q<0.05 as significance threshold, unless stated differently. The proteins in each cluster are categorized as either PA or NPA, based on the label of its encoding genome.

Validation of Predicted PA, NPA, RA, and Soil Genes Using Metagenomes

Metagenome samples (n=38) are downloaded from NCBI and GOLD. The reads are translated into proteins and proteins of at least 40 aa long are aligned using HMMsearch95 against the different protein references. The protein references include the predicted PA, RA, soil, and NPA proteins from Orthofinder found significant by the different approaches.

Principal Coordinates Analysis

In order to visualize the overall contribution of statistically significant enriched/depleted orthogroups to the differentiation of PA and NPA genomes, PCoA and logistic regression is utilized. For each of the nine taxa analyzed, this analysis is run over a collection of matrices. The first matrix is the full pan genome matrix; this matrix depicts the distribution of all the orthogroups contained across all the genomes in a given taxon. The subsequent matrices represent subsets of the full pan genome matrix, each of these matrices depict the distribution of only the statistically significant orthogroups as called by one of the five different algorithms utilized to test for the genotype-phenotype association.

The function cmdscale from the R (v 3.3.1) stats package is used to run PCoA over all the Tmatrices described above using the Canberra distance as implemented in the vegdist function from the vegan (v 2.4-2) R package (see URLs). Then, the first two axes output from the PCoA are used as independent variables to fit a logistic regression over the labels of each genome (PA, NPA). Finally, the Akaike Information Criteria (AIC) is computed for each of the different models fitted. Briefly, the AIC estimates how much information is lost when a model is applied to represent the true model of a particular dataset. See URLs for the scripts used to perform the PCoA.

Validation of PA Genes in *Paraburkholderia kururiensis* M130 Affecting Rice Root Colonization Growth and transformation details of *Paraburkholderia kururiensis* M130 are determined.

Mutant Construction

Internal fragments of 200-900 bp from each gene of interest are PCR amplified using primers. Fragments are first cloned in the pGem2T easy vector (Promega) and sequenced (GATC Biotech; Germany), then excised with EcoRI restriction enzyme and cloned in the corresponding site in pKNOCK Km R96. These plasmids are then used as a suicide delivery system in order to create the knockout mutants and transferred to *P. kururiensis* M130 by triparental mating. All the mutants are verified by PCR using primers specific to the pKNOCK-Km vector and to the genomic DNA sequences upstream and downstream from the targeted genes.

Rhizosphere Colonization Experiments with *P. kururiensis* and Mutant Derivatives Seeds of Oryza sativa (BALDO variety) are surface sterilized and are left to germinate in sterile conditions at 30° C. in the dark for seven days. Each seedling is then aseptically transferred into a 50 mL Falcon tube containing 35 mL of half strength Hoagland solution semisolid substrate (0.4% agar). The tubes are then inoculated with 107 cfu of a *P. kururiensis* suspension. Plants are grown for eleven days at 30° C. (16-8 h light-dark cycle). For the determination of the bacterial counts, plants are washed under tap water for 1 min and then cut below the cotyledon to excise the roots. Roots are air dried for 15 min, weighed and then transferred to a sterile tube containing 5 mL of PBS. After vortexing, the suspension is serially diluted to 10-1 and 10-2 in PBS and aliquots are plated on KB plates containing the appropriate antibiotic (Rif 50 μg/mL for the wt, Rif 50 μg/mL and Km 50 μg/mL for the mutants). After three days incubation at 30° C., cfu are counted. Three replicates for each dilution from ten independent plantlets are used to determine the average cfu values.

Plant Mimicking PA and RA Proteins (PREPARADOs)

Pfam25 version 30.0 metadata is downloaded. Protein domains that appear in both Viridiplantae and bacteria and occur at least twice more frequently in Viridiplantae than in bacteria were considered as plant-like domains (n=708). In parallel, the set of significant PA, RA, NPA, soil Pfam protein domains predicted by the five algorithms in the nine taxa are scanned. A list of domains is compiled that are significant PA/RA in at least four tests, and significant NPA/soil in up to two tests (n=1779). The overlap between the first two sets is defined as PREPARADOs (n=64). In parallel, two control sets of 500 random plant-like Pfam domains and 500 random PA/RA Pfam domains are created. Enrichment of PREPARADOs integrated into plant NLR proteins in comparison to the domains in the control groups is tested using the Fisher exact test. In order to identify domains found in plant disease resistance proteins, all proteins are retrieved from Phytozome and BrassicaDB. To identify domains in plant disease resistance proteins, hmmscan is used to search protein sequences for the presence of either NB-ARC (PF00931.20), TIR (PF01582.18), TIR_2 (PF13676.4), or RPW8 (PF05659.9) domains. Bacterial proteins carrying the PREPARADO domains are considered as having full-length identity to fungal, oomycete or plant proteins based on LAST alignments to all Refseq proteins of plants, fungi, and protozoa. Full-length is defined as an alignment length of at least 90% of the length of both query and reference proteins. The threshold used for considering a high amino acid identity was 40%. Explanation about prediction of secretion of proteins with PREPARADOs appears in the Supplementary Information.

Prediction of PA, NPA, RA, and Soil Operons and Their Annotation as Biosynthetic Gene Clusters Significant PA, NPA, RA, and soil genes of each genome are clustered based on genomic distance: genes sharing the same scaffold and strand that were up to 200 bp apart are clustered into the same predicted operon. Up to one spacer gene, which is a non-significant gene, is allowed between each pair of significant genes within an operon. Operons are predicted for the genes in COG and OrthoFinder clusters using all five approaches. Operons are annotated as Biosynthetic Gene Clusters (BGCs) if at least one of the constituent genes is part of a BGC from the IMG-ABC database97.

Jekyll and Hyde Analyses

To find all homologs and paralogs of Jekyll and Hyde genes, IMG blast search with an e value threshold of 1e-5 is used against all IMG isolates. Hyde1 homologs of *Acidovorax*, Hyde1 homologs of *Pseudomonas*, Hyde2, and Jekyll genes are searched using proteins of genes Aave_1071, A243_06583, Ga0078621_123530, and Ga0102403_10160 as the query sequence, respectively. Multiple sequence alignments are done using Mafft98. A phylogenetic tree of *Acidovorax* species is produced using RaxML99 based on concatenation of 35 single copy genes110.

Hyde1 Toxicity Assay

To verify the toxicity of Hyde1 and Hyde2 proteins to *E. coli*, genes encoding proteins Aave_0990 (Hyde2), Aave_0989 (Hyde1) and Aave_3191 (Hyde1) or GFP as a control, are cloned to the inducible pET28b expression vector using the LR reaction. The recombinant vectors are transformed into *E. coli* C41 competent cells using electroporation after sequencing validation. Five colonies are selected and cultured in LB liquid media supplemented with kanamycin with shaking overnight. OD600 of the bacteria culture is adjusted to 1.0 and then diluted by 102, 104, 106 and 108 times successively. Bacteria culture gradients are spotted (5 μL) on LB plates with or without 0.5 mM IPTG to induce gene expression.

Construction of Δ5-Hyde1 Strain

A Δ5-Hyde1 strain is constructed. *Acidovorax citrulli* strain AAC00-1 and its derived mutants are grown on nutrient agar medium supplemented with rifampicin (100 μg/ml). To delete a cluster of five Hyde1 genes (Aave_3191-3195), a marker-exchange mutagenesis is performed as previously described101. The marker-free mutant is designated as Δ1-Hyde1, and its genotype is confirmed by PCR amplification and sequencing. The marker-exchange mutagenesis procedure is repeated to further delete four Hyde1 loci. The final mutant with deletion of 9 out of 11 Hyde1 genes (in five loci) is designated as Δ5-Hyde1 and is used for competition assay. A ΔT6SS mutant was from Ron Walcott's lab.

Competition assay of *Acidovorax citrulli* AAC00-1 Against Different Strains

Bacterial Strains

*E. coli* BW25113 pSEVA381 is grown aerobically in LB broth (5 g/L NaCl) at 37° C. in presence of chloramphenicol. Naturally antibiotic resistant bacterial leaf isolates16 and *Acidovorax* strains are grown aerobically in NB medium (5 g/L NaCl) at 28° C. in presence of the appropriate antibiotic.

Competition Assay

Competition assays are conducted similarly as described elsewhere66,102. Briefly, bacterial overnight cultures are harvested and washed in PBS (pH 7.4) to remove excess antibiotics and resuspended in fresh NB medium to an optical density of 10. Predator and prey strains are mixed at 1:1 ratio and 5 μL of the mixture is spotted onto dry NB agar plates and incubated at 28° C. As a negative control, the same volume of NB medium is mixed with prey cells instead of the predator strain. After 19h of co-incubation, bacterial spots are excised from the agar and resuspended in 500 μL NB medium and are spotted on NB agar containing antibiotic selective for the prey strains. CFUs of recovered prey cells are determined after incubation at 28° C. All assays are performed in at least three biological replicates.

References cited (wherein each reference is incorporated by reference):

1. Ley R E, et al. Evolution of mammals and their gut microbes. Science. 2008; 777:1647-1651.
2. Baumann P. Biology of bacteriocyte-associated endosymbionts of plant sap-sucking insects. Annu Rev Microbiol. 2005; 59:155-189. [PubMed: 16153167]
3. Sprent J I. 60 Ma of legume nodulation. What's new? What's changing? J Exp Bot. 2008; 59:1081-1084. [PubMed: 18209109]
4. Pfeilmeier S, Caly D L, Malone J G. Bacterial pathogenesis of plants: future challenges from a microbial perspective. Mol Plant Pathol. 2016; 17:1298-1313. [PubMed: 27170435]
5. Chowdhury S P, Hartmann A, Gao X, Borriss R. Biocontrol mechanism by root-associated *Bacillus amyloliquefaciens* FZB42—a review. Front Microbiol. 2015; 6:780. [PubMed: 26284057]
6. Fibach-Paldi S, Burdman S, Okon Y. Key physiological properties contributing to rhizosphere adaptation and plant growth promotion abilities of *Azospirillum brasilense*. FEMS Microbiol Lett. 2012; 326:99-108. [PubMed: 22092983]
7. Santhanam R, et al. Native root-associated bacteria rescue a plant from a sudden-wilt disease that emerged during continuous cropping. Proc Natl Acad Sci USA. 2015; 112:E5013-20. [PubMed: 26305938]
8. Peters N K, Frost J W, Long S R. A plant flavone, luteolin, induces expression of Rhizobium meliloti nodulation genes. Science. 1986; 233:977-80. [PubMed: 3738520]
9. Hiei Y, Ohta S, Komari T, Kumashiro T. Efficient transformation of rice (Oryza sativa L) mediated by Agrobacterium and sequence analysis of the boundaries of the T-DNA. Plant J. 1994; 6:271-82. [PubMed: 7920717]
10. Hueck C J. Type III protein secretion systems in bacterial pathogens of animals and plants. Microbiol Mol Biol Rev. 1998; 62:379-433. [PubMed: 9618447]
11. Bulgarelli D, et al. Revealing structure and assembly cues for *Arabidopsis* root-inhabiting bacterial microbiota. Nature. 2012; 488:91-5. [PubMed: 22859207]

12. Lundberg D S, et al. Defining the core *Arabidopsis thaliana* root microbiome. Nature. 2012; 488:86-90. [PubMed: 22859206]
13. Bulgarelli D, Schlaeppi K, Spaepen S, Ver Loren van Themaat E, Schulze-Lefert P. Structure and functions of the bacterial microbiota of plants. Annu Rev Plant Biol. 2013; 64:807-38. [PubMed: 23373698]
14. Ofek-Lalzar M, et al. Niche and host-associated functional signatures of the root surface microbiome. Nat Commun. 2014; 5:4950. [PubMed: 25232638]
15. Gottel N R, et al. Distinct microbial communities within the endosphere and rhizosphere of *Populus deltoides* roots across contrasting soil types. Appl Environ Microbiol. 2011; 77:5934-5944. [PubMed: 21764952]
16. Bal Y, et al. Functional overlap of the *Arabidopsis* leaf and root microbiota. Nature. 2015; 528:364-369. [PubMed: 26633631]
17. Hardoim P R, et al. The hidden world within plants: ecological and evolutionary considerations for defining functioning of microbial endophytes. Microbiol Mol Biol Rev. 2015; 79:293-320. [PubMed: 26136581]
18. Bulgarelli D, et al. Structure and function of the bacterial root microbiota in wild and domesticated barley. Cell Host Microbe. 2015; 17:392-403. [PubMed: 25732064]
19. Hacquard S, et al. Microbiota and host nutrition across plant and animal kingdoms. Cell Host Microbe. 2015; 17:603-616. [PubMed: 25974302]
20. Tatusov R L, Galperin M Y, Natale D A, Koonin E V. The COG database: a tool for genome-scale analysis of protein functions and evolution. Nucleic Acids Res. 2000; 28:33-6. [PubMed: 10592175]
21. Kanehisa M, Sato Y, Kawashima M, Furumichi M, Tanabe M. KEGG as a reference resource for gene and protein annotation. Nucleic Acids Res. 2016; 44:D457-D462. [PubMed: 26476454]
22. Haft D H, Selengut J D, White O. The TIGRFAMs database of protein families. Nucleic Acids Res. 2003; 31:371-3. [PubMed: 12520025]
23. Huntemann M, et al. The standard operating procedure of the DOE-JGI Microbial Genome Annotation Pipeline (MGAP v. 4). Stand Genomic Sci. 2015; 1-6. DOI: 10.1186/s40793-015-0077-y [PubMed: 25678942]
24. Emms D M, Kelly S. OrthoFinder: solving fundamental biases in whole genome comparisons dramatically improves orthogroup inference accuracy. Genome Biol. 2015; 16:157. [PubMed: 26243257]
25. Finn R D, et al. The Pfam protein families database: towards a more sustainable future. Nucleic Acids Res. 2016; 44:D279-85. [PubMed: 26673716]
26. Ives A R, Garland T. Phylogenetic logistic regression for binary dependent variables. Syst Biol. 2010; 59:9-26. [PubMed: 20525617]
27. Brynildsrud O, Bohlin J, Scheffer L, Eldholm V. Rapid scoring of genes in microbial pan-genome-wide association studies with Scoary. Genome Biol. 2016; 17:238. [PubMed: 27887642]
28. Hultman J, et al. Multi-omics of permafrost, active layer and thermokarst bog soil microbiomes. Nature. 2015; 521:208-212. [PubMed: 25739499]
29. Louca S, et al. Integrating biogeochemistry with multiomic sequence information in a model oxygen minimum zone. Proc Natl Acad Sci USA. 2016; 113:E5925-E5933. [PubMed: 27655888]
30. Coutinho B G, Licastro D, Mendonça-Previato L, Cámara M, Venturi V. Plant-Influenced Gene Expression in the Rice Endophyte *Burkholderia kururiensis* M130. Mol Plant-Microbe Interact. 2015; 28:10-21. [PubMed: 25494355]
31. Long S R. Rhizobium-legume nodulation: Life together in the underground. Cell. 1989; 56:203-214. [PubMed: 2643474]
32. Ruvkun G B, Sundaresan V, Ausubel F M. Directed transposon Tn5 mutagenesis and complementation analysis of Rhizobium meliloti symbiotic nitrogen fixation genes. Cell. 1982; 29:551-9. [PubMed: 6288262]
33. Hershey D M, Lu X, Zi J, Peters R J. Functional conservation of the capacity for ent-kaurene biosynthesis and an associated operon in certain rhizobia. J Bacteriol. 2014; 196:100-6. [PubMed: 24142247]
34. Nett R S, et al. Elucidation of gibberellin biosynthesis in bacteria reveals convergent evolution. Nat Chem Biol. 2016; 13:69-74. [PubMed: 27842068]
35. Scharf B E, Hynes M F, Alexandre G M. Chemotaxis signaling systems in model beneficial plant-bacteria associations. Plant Mol Biol. 2016; 90:549-559. [PubMed: 26797793]
36. Buttner D, He S Y. Type III protein secretion in plant pathogenic bacteria. Plant Physiol. 2009; 150:1656-64. [PubMed: 19458111]
37. Gao R, et al. Genome-wide RNA sequencing analysis of quorum sensing-controlled regulons in the plant-associated *Burkholderia glumae* PG1 strain. Appl Environ Microbiol. 2015; 81:7993-8007. [PubMed: 26362987]
38. Weller-Stuart T, Toth I, De Maayer P, Coutinho T. Swimming and twitching motility are essential for attachment and virulence of Pantoea ananatis in onion seedlings. Mol Plant Pathol. 2016; doi: 10.1111/mpp.12432
39. De Weger L A, et al. Flagella of a plant-growth-stimulating *Pseudomonas fluorescens* strain are required for colonization of potato roots. J Bacteriol. 1987; 169: 2769-73. [PubMed: 3294806]
40. De Weert S, et al. Flagella-Driven Chemotaxis Towards Exudate Components Is an Important Trait for Tomato Root Colonization by *Pseudomonas fluorescens*. 2002; 15
41. Ravcheev D A, et al. Comparative genomics and evolution of regulons of the LacI-family transcription factors. Front Microbiol. 2014; 5:294. [PubMed: 24966856]
42. Yamauchi Y, Hasegawa A, Taninaka A, Mizutani M, Sugimoto Y. NADPH-dependent reductases involved in the detoxification of reactive carbonyls in plants. J Biol Chem. 2011; 286:6999-7009. [PubMed: 21169366]
43. Burstein D, et al. Genome-scale identification of *Legionella pneumophila* effectors using a machine learning approach. PLoS Pathog. 2009; 5:e1000508. [PubMed: 19593377]
44. Dean P. Functional domains and motifs of bacterial type III effector proteins and their roles in infection. FEMS Microbiol Rev. 2011; 35:1100-1125. [PubMed: 21517912]
45. Stebbins C E, Galán J E. Structural mimicry in bacterial virulence. Nature. 2001; 412:701-705. [PubMed: 11507631]
46. Price C T, et al. Molecular mimicry by an F-Box effector of *Legionella pneumophila* hijacks a conserved polyubiquitination machinery within macrophages and protozoa. PLoS Pathog. 2009; 5:e1000704. [PubMed: 20041211]
47. Rothmeier E, et al. Activation of Ran GTPase by a *Legionella* effector promotes microtubule polymerization, pathogen vacuole motility and infection. PLoS Pathog. 2013; 9:e1003598. [PubMed: 24068924]
48. Xu R Q, et al. AvrACXcc8004, a Type III Effector with a Leucine-Rich Repeat domain from *Xanthomonas camp-*

*estris Pathovar campestris* confers avirulence in vascular tissues of *Arabidopsis thaliana* ecotype Col-0. J Bacteriol. 2008; 190:343-355. [PubMed: 17951377]

49. Shevchik V E, Robert-Baudouy J, Hugouvieux-Cotte-Pattat N. Pectate lyase Pell of *Erwinia chrysanthemi* 3937 belongs to a new family. J Bacteriol. 1997; 179:7321-30. [PubMed: 9393696]
50. Cesari S, Bernoux M, Moncuquet P, Kroj T, Dodds P N. A novel conserved mechanism for plant NLR protein pairs: the 'integrated decoy'•hypothesis. Front Plant Sci. 2014; 5
51. Sarris P F, et al. A plant immune receptor detects pathogen effectors that target WRKY transcription factors. Cell. 2015; 161:1089-1100. [PubMed: 26000484]
52. Sarris P F, et al. Comparative analysis of plant immune receptor architectures uncovers host proteins likely targeted by pathogens. BMC Biol. 2016; 14:8. [PubMed: 26891798]
53. Le Roux C, et al. A receptor pair with an integrated decoy converts pathogen disabling of transcription factors to immunity. Cell. 2015; 161:1074-1088. [PubMed: 26000483]
54. Immunology of fungal infections. Springer; Netherlands: 2007.
55. Gadjeva M, Takahashi K, Thiel S. Mannan-binding lectin—a soluble pattern recognition molecule. Mol Immunol. 2004; 41:113-21. [PubMed: 15159056]
56. Ma Q H, Tian B, Li Y L. Overexpression of a wheat jasmonate-regulated lectin increases pathogen resistance. Biochimie. 2010; 92:187-193. [PubMed: 19958808]
57. Xiang Y, et al. A jacalin-related lectin-like gene in wheat is a component of the plant defence system. J Exp Bot. 2011; 62:5471-5483. [PubMed: 21862481]
58. Yamaji Y, et al. Lectin-mediated resistance impairs plant virus infection at the cellular level. Plant Cell. 2012; 24:778-93. [PubMed: 22307853]
59. Weidenbach D, et al. Polarized defense against fungal pathogens is mediated by the Jacalin-related lectin domain of modular Poaceae-specific proteins. Mol Plant. 2016; 9:514-527. [PubMed: 26708413]
60. Sahly H, et al. Surfactant protein D binds selectively to *Klebsiella pneumoniae* lipopolysaccharides containing mannose-rich O-antigens. J Immunol. 2002; 169:3267-74. [PubMed: 12218146]
61. Osborn M J, Rosen S M, Rothfield L, Zelenick L D, Horecker B L. Lipopolysaccharide of the gram-negative cell wall. Science. 1964; 145:783-9. [PubMed: 14163315]
62. Tans-Kersten J, Huang H, Allen C. Ralstonia solanacearum needs motility for invasive virulence on tomato. J Bacteriol. 2001; 183:3597-605. [PubMed: 11371523]
63. Cole B J, et al. Genome-wide identification of bacterial plant colonization genes. PLOS Biol. 2017; 15:e2002860. [PubMed: 28938018]
64. Poggio S, et al. A complete set of flagellar genes acquired by horizontal transfer coexists with the endogenous flagellar system in *Rhodobacter sphaeroides*. J Bacteriol. 2007; 189:3208-16. [PubMed: 17293429]
65. Ho B T, Dong T G, Mekalanos J J. A view to a kill: the bacterial type VI secretion system. Cell Host Microbe. 2014; 15:9-21. [PubMed: 24332978]
66. MacIntyre D L, Miyata S T, Kitaoka M, Pukatzki S. The Vibrio cholerae type VI secretion system displays antimicrobial properties. Proc Natl Acad Sci USA. 2010; 107:19520-4. [PubMed: 20974937]
67. Tian Y, et al. The type VI protein secretion system contributes to biofilm formation and seed-to-seedling transmission of *Acidovorax citrulli* on melon. Mol Plant Pathol. 2015; 16:38-47. [PubMed: 24863458]
68. Peiffer J A, et al. Diversity and heritability of the maize rhizosphere microbiome under field conditions. Proc Natl Acad Sci USA. 2013; 110:6548-53. [PubMed: 23576752]
69. Agler M T, et al. Microbial hub taxa link host and abiotic factors to plant microbiome variation. PLOS Biol. 2016; 14:e1002352. [PubMed: 26788878]
70. Bokulich N A, Thorngate J H, Richardson P M, Mills D A. Microbial biogeography of wine grapes is conditioned by cultivar, vintage, and climate. Proc Natl Acad Sci USA. 2014; 111:E139-48. [PubMed: 24277822]
71. Coleman-Derr D, et al. Plant compartment and biogeography affect microbiome composition in cultivated and native *Agave* species. New Phytol. 2016; 209:798-811. [PubMed: 26467257]
72. Shade A, McManus P S, Handelsman J. Unexpected diversity during community succession in the apple flower microbiome. MBio. 2013; 4:e00602-12. [PubMed: 23443006]
73. Turner T R, et al. Comparative metatranscriptomics reveals kingdom level changes in the rhizosphere microbiome of plants. ISME J. 2013; 7:2248-2258. [PubMed: 23864127]
74. Edwards J, et al. Structure, variation, and assembly of the root-associated microbiomes of rice. Proc Natl Acad Sci USA. 2015; 112:E911-20. [PubMed: 25605935]
75. Kroj T, Chanclud E, Michel-Romiti C, Grand X, Morel J B. Integration of decoy domains derived from protein targets of pathogen effectors into plant immune receptors is widespread. New Phytol. 2016; 210:618-26. [PubMed: 26848538]
76. Mukhtar M S, et al. Independently evolved virulence effectors converge onto hubs in a plant immune system network. Science (80-). 2011; 333:596-601.
77. Vimr E, Lichtensteiger C. To sialylate, or not to sialylate: that is the question. Trends Microbiol. 2002; 10:254-7. [PubMed: 12088651]
78. de Jonge R, et al. Conserved fungal LysM efector Ecp6 prevents chitin-triggered immunity in plants. Science (80-). 2010; 329
79. Doty S L, et al. Diazotrophic endophytes of native black cottonwood and willow. Symbiosis. 2009; 47:23-33.
80. Weston D J, et al. *Pseudomonas fluorescens* induces strain-dependent and strain-independent host plant responses in defense networks, primary metabolism, photosynthesis, and fitness. Mol Plant-Microbe Interact. 2012; 25:765-778. [PubMed: 22375709]
81. Rinke C, et al. Insights into the phylogeny and coding potential of microbial dark matter. Nature. 2013; 499:431-437. [PubMed: 23851394]
82. Integrated Microbial Genomes. Available at: the webpage for: img.jgi.doe.gov/cgi-bin/mer/main.cgi.
83. Beszteri B, Temperton B, Frickenhaus S, Giovannoni S J. Average genome size: a potential source of bias in comparative metagenomics. ISME J. 2010; 4:1075-1077. [PubMed: 20336158]
84. Parks D H, Imelfort M, Skennerton C T, Hugenholtz P, Tyson G W. CheckM: assessing the quality of microbial genomes recovered from isolates, single cells, and metagenomes. Genome Res. 2015; 25:1043-55. [PubMed: 25977477]
85. Varghese N J, et al. Microbial species delineation using whole genome sequences. Nucleic Acids Res. 2015; 43:6761-71. [PubMed: 26150420]

86. Kerepesi C, Bánky D, Grolmusz V. AmphoraNet: The webserver implementation of the AMPHORA2 metagenomic workflow suite. Gene. 2014; 533:538-540. [PubMed: 24144838]
87. Wu M, et al. Accounting for alignment uncertainty in phylogenomics. PLoS One. 2012; 7:e30288. [PubMed: 22272325]
88. Price M N, et al. FastTree 2—approximately Maximum-Likelihood trees for large alignments. PLoS One. 2010; 5:e9490. [PubMed: 20224823]
89. Sen A, et al. Phylogeny of the class Actinobacteria revisited in the light of complete genomes. Int J Syst Evol Microbiol. 2014; 64:3821-3832. [PubMed: 25168610]
90. Edgar R C. Search and clustering orders of magnitude faster than BLAST. Bioinformatics. 2010; 26:2460-2461. [PubMed: 20709691]
91. Buchfink B, Xie C, Huson D H. Fast and sensitive protein alignment using DIAMOND. Nat Methods. 2014; 12:59-60. [PubMed: 25402007]
92. Wang Z, Wu M. A Phylum-Level Bacterial Phylogenetic Marker Database. Mol Biol Evol. 2013; 30:1258-1262. [PubMed: 23519313]
93. Benjamini Y, Hochberg Y. Controlling the false discovery rate: A practical and powerful approach to multiple testing. Source J R Stat Soc Ser B J R Stat Soc Ser B J R Stat Soc B. 1995; 57:289-300.
94. Finn R D, et al. HMMER web server: 2015 update. Nucleic Acids Res. 2015; 43:W30-W38. [PubMed: 25943547]
95. Alexeyev M F. The pKNOCK series of broad-host-range mobilizable suicide vectors for gene knockout and targeted DNA insertion into the chromosome of gram-negative bacteria. Biotechniques. 1999; 26828:824-6. [PubMed: 10337469]
96. Hadjithomas M, et al. IMG-ABC: a knowledge base to fuel discovery of biosynthetic gene clusters and novel secondary metabolites. MBio. 2015; 6:e00932. [PubMed: 26173699]
97. Katoh K, Misawa K, Kuma K, Miyata T. MAFFT: a novel method for rapid multiple sequence alignment based on fast Fourier transform. Nucleic Acids Res. 2002; 30:3059-66. [PubMed: 12136088]
98. Stamatakis A, Hoover P, Rougemont J. A rapid bootstrap algorithm for the RAxML web servers. Syst Biol. 2008; 57:758-771. [PubMed: 18853362]
99. Finkel O M, Béjà O, Belkin S. Global abundance of microbial rhodopsins. ISME J. 2013; 7:448-451. [PubMed: 23051692]
100. Traore, S M. Characterization of Type Three Effector Genes of *A. citrulli*, the Causal Agent of Bacterial Fruit Blotch of Cucurbits. Virginia Polytechnic Institute and State University; 2014.
101. Basler M, Ho B T, Mekalanos J J. Tit-for-Tat: Type VI Secretion System Counterattack during Bacterial Cell-Cell Interactions. Cell. 2013; 152:884-894. [PubMed: 23415234]

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a disease caused all or in part by a *Escherichia coli* cell, comprising: administering a pharmaceutical composition comprising a purified or isolated Hyde1 gene product and a pharmaceutically acceptable carrier to a subject in need thereof; wherein the Hyde1 gene product is SEQ ID NO:1, and the *Escherichia coli* cell is a human pathogen and the subject is a human patient.

* * * * *

SEQUENCE LISTING

```
<160> NUMBER OF SEQ ID NOS: 48

<210> SEQ ID NO 1
<211> LENGTH: 135
<212> TYPE: PRT
<213> ORGANISM: Acidovorax avenae

<400> SEQUENCE: 1

Met Lys Leu Ser Asn Leu Lys Asn Val Pro Cys Ile Val Trp Cys Leu
1               5                   10                  15

Gly Leu Asn Ala Leu Phe Leu Ala Gly Trp Ala Leu Ala Thr Pro Thr
            20                  25                  30

Phe Ala Asp Ala Glu Asn Ser Pro His Arg Val Tyr Arg Leu Glu Phe
        35                  40                  45

His Lys Ala Ser Phe Leu Gln Arg Ile Thr His Pro Arg Phe Lys Met
    50                  55                  60

Pro Tyr Val Val Arg Leu Tyr Arg Ile Glu Pro Lys Thr Leu Leu Gly
65                  70                  75                  80

Gln Ser Glu Val Val Asp Leu Trp Leu Asn Gly Glu Ile His Trp Tyr
                85                  90                  95

Leu Asp Pro Pro Val Asp Met Asn Arg Val Arg Val Gly Arg Asp Val
            100                 105                 110

Leu Phe Glu Ser Ile Pro Pro Glu Cys Thr Lys Glu Ala Gln Ile Pro
        115                 120                 125

Ser Cys Pro Asn Thr Lys Pro
    130                 135
```

<210> SEQ ID NO 2
<211> LENGTH: 135
<212> TYPE: PRT
<213> ORGANISM: Acidovorax avenae

<400> SEQUENCE: 2

```
Met Lys Leu Ser Gly Leu Lys Asn Val Pro Cys Ile Leu Trp Cys Leu
1               5                   10                  15

Ala Leu Asn Ala Cys Val Val Leu Gly Trp Tyr Ala Thr Lys Pro Thr
            20                  25                  30

Leu Phe Asn Ser Tyr Asn Ser Pro Arg Tyr Val Tyr Arg Leu Glu Leu
        35                  40                  45

Tyr His Ala Ser Leu Trp Gln Arg Ile Ile His Tyr Asp Gln Lys Ala
    50                  55                  60

Pro Phe Ile Val Arg Leu His Arg Val Asp Pro Lys Glu Leu Leu Gly
65                  70                  75                  80

Glu Ser Gln Val Val Asp Leu Trp Ser Gly Ile Asp Ile Asp Trp Gln
                85                  90                  95

Leu Asp Pro Leu Val Gln Thr Asn Lys Val Tyr Val Gly Arg Asp Val
            100                 105                 110

Ile Phe Arg Asn Ile Pro Pro Glu Cys Thr Glu Ala Ala Gln Leu Gln
        115                 120                 125

Gly Cys Pro Asn Thr Lys Pro
    130                 135
```

<210> SEQ ID NO 3
<211> LENGTH: 135
<212> TYPE: PRT
<213> ORGANISM: Acidovorax avenae

<400> SEQUENCE: 3

```
Met Lys Leu Pro Asn Leu Lys Asn Val Pro Cys Ile Val Trp Cys Leu
1               5                   10                  15

Gly Leu Asn Ala Leu Leu Leu Ala Gly Trp Ala Leu Ala Thr Pro Thr
            20                  25                  30

Phe Ala Asp Ala Glu Asn Ser Pro His Arg Val Tyr Arg Leu Glu Phe
        35                  40                  45

His Lys Ala Ser Phe Leu Gln Arg Ile Thr His Pro Ser Phe Lys Met
    50                  55                  60

Pro Tyr Val Val Arg Leu Tyr Arg Ile Glu Pro Lys Thr Leu Leu Gly
65                  70                  75                  80

Gln Ser Glu Val Val Asp Leu Trp Leu Asn Gly Glu Ile His Trp Tyr
                85                  90                  95

Leu Asp Pro Pro Val Glu Leu Ser Arg Val His Val Gly Gln Asp Val
            100                 105                 110

Thr Phe Glu Asn Ile Pro Pro Glu Cys Thr Lys Glu Ala Gln Ile Pro
        115                 120                 125

Gly Cys Pro Asp Thr Lys Pro
    130                 135
```

<210> SEQ ID NO 4
<211> LENGTH: 135
<212> TYPE: PRT
<213> ORGANISM: Acidovorax avenae

<400> SEQUENCE: 4

```
Met Asn Leu Phe Asn Leu Lys Asn Ala Pro Cys Ile Val Trp Cys Leu
```

-continued

```
1               5                   10                  15

Ala Leu Asn Ala Cys Val Val Leu Gly Trp Tyr Ala Thr Thr Pro Thr
            20                  25                  30

Leu Phe Met Thr Tyr Asn Ser Pro His Ser Val Tyr Arg Leu Glu Ile
        35                  40                  45

His Arg Ala Ser Pro Trp Gln Arg Ile Val His Arg Asp Gln Glu Ala
    50                  55                  60

Pro Ala Ile Val Arg Leu Tyr Arg Ile Asp Pro Lys Glu Leu Leu Gly
65                  70                  75                  80

Glu Ser Lys Val Val Asp Leu Met Asp Gly Ser Gly Ile Asp Trp Gln
                85                  90                  95

Leu Asp Pro Pro Val Gln Ala Asn Lys Val Tyr Val Gly Pro Gly Val
            100                 105                 110

Val Phe Glu Asn Ile Pro Ser Glu Cys Thr Ala Ala Gly His Ile Pro
        115                 120                 125

Gly Cys Pro Asn Thr Lys Pro
    130                 135


<210> SEQ ID NO 5
<211> LENGTH: 135
<212> TYPE: PRT
<213> ORGANISM: Acidovorax avenae

<400> SEQUENCE: 5

Met Lys Leu Ser His Leu Lys Lys Val Pro Cys Ile Val Trp Cys Leu
1               5                   10                  15

Gly Leu Asn Ala Leu Phe Leu Ala Gly Trp Ala Leu Ala Thr Pro Thr
            20                  25                  30

Phe Ala Asp Ala Glu Asn Ser Pro His Arg Val Tyr Arg Leu Glu Phe
        35                  40                  45

His Lys Ala Ser Phe Leu Gln Arg Ile Thr His Pro Arg Phe Lys Met
    50                  55                  60

Pro Tyr Val Val Arg Leu Tyr Arg Ile Glu Pro Lys Thr Leu Leu Gly
65                  70                  75                  80

Gln Ser Glu Val Val Asp Leu Trp Leu Asn Gly Glu Ile Gln Trp Tyr
                85                  90                  95

Leu Asp Pro Pro Val Asp Met Asn Arg Val Arg Val Gly Arg Asp Val
            100                 105                 110

Leu Phe Glu Ser Ile Pro Ser Glu Cys Ser Glu Ala Ala Gln Ile Pro
        115                 120                 125

Gly Cys Pro Asn Thr Lys Pro
    130                 135


<210> SEQ ID NO 6
<211> LENGTH: 136
<212> TYPE: PRT
<213> ORGANISM: Acidovorax avenae

<400> SEQUENCE: 6

Met Lys Leu Ala Asn Leu Lys Ser Val Pro Cys Ile Val Trp Cys Leu
1               5                   10                  15

Ala Leu Asn Ala Cys Leu Val Leu Gly Trp Tyr Ala Thr Arg Pro Thr
            20                  25                  30

Leu Phe Met Thr Tyr Asn Ser Pro His Tyr Val Tyr Arg Leu Glu Ile
        35                  40                  45

Tyr Glu Ala Ser Leu Trp Gln Arg Ile Val His His Asp Gln Arg Asp
```

```
    50                  55                  60

Pro Gly Ile Phe Arg Leu Tyr Glu Val Asn His Lys Lys Leu Leu Gly
65                  70                  75                  80

Glu Ser Lys Val Val Asp Leu Glu Pro Gly Ile Gly Ala Ile Asp Trp
                85                  90                  95

Tyr Leu Asp Pro Pro Met Gln Ala Asn Lys Val Tyr Ala Gly Leu Gly
            100                 105                 110

Val Val Phe Glu Asn Ile Pro Ser Glu Cys Pro Ile Val Gly Gln Val
        115                 120                 125

Pro Gly Cys Leu Ser Ala Lys Pro
    130                 135


<210> SEQ ID NO 7
<211> LENGTH: 133
<212> TYPE: PRT
<213> ORGANISM: Acidovorax avenae

<400> SEQUENCE: 7

Met Asn Phe Ser Gln Leu Lys Lys Ile Pro Cys Ile Val Trp Cys Leu
1               5                   10                  15

Ala Val Asn Ala Leu Val Ile Met Ile Trp Cys Ala Ala Thr Pro Thr
            20                  25                  30

Phe Phe Asp Ser Glu Asn Ser Pro His Arg Val Tyr Arg Leu Glu Phe
        35                  40                  45

His Lys Ala Ser Leu Leu Gln Lys Ile Ala His Pro Thr Phe Lys Met
    50                  55                  60

Pro Tyr Ile Val Arg Leu Tyr Lys Ile Glu Pro Lys Thr Leu Leu Gly
65                  70                  75                  80

Glu Ser Glu Val Val Asp Leu Trp Leu Asn Gly Glu Ile Thr Trp Tyr
                85                  90                  95

Leu Asn Ser Ser Val Asp Gln Asn Glu Val Arg Val Gly Arg Asp Val
            100                 105                 110

Val Phe Glu Lys Val Pro Pro Glu Cys Thr Pro Ala Ser Pro Leu Val
        115                 120                 125

Ser Cys Pro Lys Pro
    130


<210> SEQ ID NO 8
<211> LENGTH: 130
<212> TYPE: PRT
<213> ORGANISM: Acidovorax avenae

<400> SEQUENCE: 8

Met Thr Thr Thr Arg Arg Phe Lys Val Ala Ala Leu Leu Leu Gly Ile
1               5                   10                  15

Ala Val Val Gly Ile Thr Leu Arg Ser Leu Ala Thr Pro Glu Tyr Gln
            20                  25                  30

Arg Ser His Tyr Ser Pro Arg His Val Tyr Arg Leu Asp Tyr Tyr Glu
        35                  40                  45

Ala Ser Trp Leu Gln Arg Met Ala His Trp Asp Met Arg Tyr Pro His
    50                  55                  60

Val Ile Arg Leu Tyr Arg Ile Glu Pro Pro Ala Leu Leu Gly Glu Ser
65                  70                  75                  80

Ala Val Val Asp Leu Trp Ile Asn Gly Gln Leu Tyr Trp Tyr Leu Asn
                85                  90                  95

Pro Pro Met Asn Lys Val Arg Ile Gly Arg Asp Val Val Phe Glu Asn
```

```
            100                 105                 110

Ile Pro Pro Glu Cys Thr Gly Cys Pro Pro Leu Pro Asp Ser Ala Val
        115                 120                 125

Met Pro
    130


<210> SEQ ID NO 9
<211> LENGTH: 130
<212> TYPE: PRT
<213> ORGANISM: Acidovorax avenae

<400> SEQUENCE: 9

Met Thr Thr Thr Arg Arg Phe Lys Val Ala Ala Leu Leu Leu Gly Ile
1               5                   10                  15

Ala Val Val Gly Ile Thr Leu Arg Ser Leu Ala Thr Pro Glu Tyr Gln
            20                  25                  30

Arg Ser His Tyr Ser Pro Arg His Val Tyr Arg Leu Asp Tyr Tyr Glu
        35                  40                  45

Ala Ser Trp Leu Gln Arg Met Ala His Trp Asp Met Arg Tyr Pro His
    50                  55                  60

Val Ile Arg Leu Tyr Arg Ile Glu Pro Pro Ala Leu Leu Gly Glu Ser
65                  70                  75                  80

Ala Val Val Asp Leu Trp Ile Asn Gly Gln Leu Tyr Trp Tyr Leu Asn
                85                  90                  95

Pro Pro Met Asn Lys Val Arg Ile Gly Arg Asp Val Val Phe Glu Asn
            100                 105                 110

Ile Pro Pro Glu Cys Thr Gly Cys Pro Pro Leu Pro Asp Ser Ala Val
        115                 120                 125

Met Pro
    130


<210> SEQ ID NO 10
<211> LENGTH: 127
<212> TYPE: PRT
<213> ORGANISM: Acidovorax avenae

<400> SEQUENCE: 10

Met Asn Gly Lys Arg Leu Val Lys Trp Ala Val Ala Ala Val Leu Ser
1               5                   10                  15

Ala Ile Val Leu Gly Tyr Ser Ala Ile Pro Arg Tyr Asp Arg Ser His
            20                  25                  30

Tyr Ser Pro Arg His Val Tyr Arg Leu Asp Tyr Tyr Glu Ala Ser Trp
        35                  40                  45

Leu Gln Arg Leu Met His Trp Asn Met Lys Tyr Pro His Val Ile Arg
    50                  55                  60

Leu Tyr Arg Ile Glu Pro Glu Thr Leu Leu Gly Glu Ser Gly Val Val
65                  70                  75                  80

Asp Leu Trp Leu Asn Gly Asp Ile Asn Trp Trp Phe Asp Pro Pro Leu
                85                  90                  95

Asn Val Val Arg Ile Gly Gln Asp Val Val Phe Glu Asn Ile Pro Pro
            100                 105                 110

Glu Cys Val Asp Cys Pro Arg Leu Pro Asp Ser Val Leu Met Pro
        115                 120                 125


<210> SEQ ID NO 11
<211> LENGTH: 127
<212> TYPE: PRT
```

<213> ORGANISM: Acidovorax avenae

<400> SEQUENCE: 11

```
Met Ala Ser Asn Asn Lys Lys Met Arg Thr Gln Thr Leu Trp Met Val
1               5                   10                  15

Leu Ala Leu Gly Leu Ala Ala Phe Val Trp Tyr Ala Ser Lys Pro Val
            20                  25                  30

Phe Lys Gly Ser Glu Thr Ser Pro Met Asn Val Tyr Arg Ile Glu Tyr
        35                  40                  45

Tyr Asp Ala Ser Pro Ile Gln Arg Ile Leu His Tyr Gln Met Lys Thr
    50                  55                  60

Pro Ser Phe Val Arg Leu Tyr Arg Ile Gln Pro Glu Thr Leu Leu Gly
65                  70                  75                  80

Glu Ser Glu Ile Val Asp Ile Trp Met Asn Gly Thr Leu His Trp Trp
                85                  90                  95

Thr Asp Pro Pro Ala His Ala Val Val Val Gly Ser Ser Val Val Phe
            100                 105                 110

Glu Asn Ile Pro Ala Glu Cys Pro Ala Ala Thr Ser Cys Pro Arg
        115                 120                 125
```

<210> SEQ ID NO 12
<211> LENGTH: 5
<212> TYPE: PRT
<213> ORGANISM: Acidovorax avenae

<400> SEQUENCE: 12

```
Val Tyr Arg Leu Glu
1               5
```

<210> SEQ ID NO 13
<211> LENGTH: 5
<212> TYPE: PRT
<213> ORGANISM: Acidovorax avenae

<400> SEQUENCE: 13

```
Val Tyr Arg Leu Asp
1               5
```

<210> SEQ ID NO 14
<211> LENGTH: 5
<212> TYPE: PRT
<213> ORGANISM: Acidovorax avenae
<220> FEATURE:
<221> NAME/KEY: misc_feature
<222> LOCATION: (3)..(4)
<223> OTHER INFORMATION: Xaa can be any naturally occurring amino acid

<400> SEQUENCE: 14

```
Gln Arg Xaa Xaa His
1               5
```

<210> SEQ ID NO 15
<211> LENGTH: 6
<212> TYPE: PRT
<213> ORGANISM: Acidovorax avenae

<400> SEQUENCE: 15

```
Val Arg Leu Tyr Arg Ile
1               5
```

<210> SEQ ID NO 16
<211> LENGTH: 6

<212> TYPE: PRT
<213> ORGANISM: Acidovorax avenae

<400> SEQUENCE: 16

Val Arg Leu Tyr Arg Val
1 5

<210> SEQ ID NO 17
<211> LENGTH: 6
<212> TYPE: PRT
<213> ORGANISM: Acidovorax avenae

<400> SEQUENCE: 17

Val Arg Leu His Arg Ile
1 5

<210> SEQ ID NO 18
<211> LENGTH: 6
<212> TYPE: PRT
<213> ORGANISM: Acidovorax avenae

<400> SEQUENCE: 18

Val Arg Leu His Arg Val
1 5

<210> SEQ ID NO 19
<211> LENGTH: 6
<212> TYPE: PRT
<213> ORGANISM: Acidovorax avenae

<400> SEQUENCE: 19

Ile Arg Leu Tyr Arg Ile
1 5

<210> SEQ ID NO 20
<211> LENGTH: 14
<212> TYPE: PRT
<213> ORGANISM: Acidovorax avenae
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 20

Pro Xaa Xaa Leu Leu Gly Xaa Ser Xaa Xaa Val Asp Ile Trp
1 5 10

<210> SEQ ID NO 21
<211> LENGTH: 6
<212> TYPE: PRT
<213> ORGANISM: Acidovorax avenae

<400> SEQUENCE: 21

Ile Arg Leu Tyr Arg Val
1 5

<210> SEQ ID NO 22
<211> LENGTH: 6
<212> TYPE: PRT

<213> ORGANISM: Acidovorax avenae

<400> SEQUENCE: 22

Ile Arg Leu His Arg Ile
1 5

<210> SEQ ID NO 23
<211> LENGTH: 6
<212> TYPE: PRT
<213> ORGANISM: Acidovorax avenae

<400> SEQUENCE: 23

Ile Arg Leu His Arg Val
1 5

<210> SEQ ID NO 24
<211> LENGTH: 14
<212> TYPE: PRT
<213> ORGANISM: Acidovorax avenae
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 24

Pro Xaa Xaa Leu Leu Gly Xaa Ser Xaa Xaa Val Asp Xaa Trp
1 5 10

<210> SEQ ID NO 25
<211> LENGTH: 14
<212> TYPE: PRT
<213> ORGANISM: Acidovorax avenae
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 25

Pro Xaa Xaa Leu Leu Gly Xaa Ser Xaa Xaa Val Asp Leu Trp
1 5 10

<210> SEQ ID NO 26
<211> LENGTH: 147
<212> TYPE: PRT
<213> ORGANISM: Pseudomonas syringae

<400> SEQUENCE: 26

Met Lys Ser Pro Ser Thr His Ile Ile Phe Leu Ala Thr Phe Ile Thr
1 5 10 15

-continued

```
Thr Ala Gly Ser Leu Trp Ala Ser Ser Glu Tyr Trp Glu Lys Gly Leu
            20                  25                  30

Ala Glu Ser Leu Asn Glu Pro Asp Ile Ser Pro Gly Gly Cys Tyr Arg
        35                  40                  45

Val Glu Thr Phe Lys Pro Phe Trp Ile Leu Pro Met Met Phe His Arg
    50                  55                  60

Lys Ala Asn Pro Tyr Lys Asp His Ser Pro Lys Trp Leu Pro Trp Trp
65                  70                  75                  80

Gly Tyr Pro Ala Phe Phe Arg Leu Tyr Asp His Arg Thr Gly Lys Leu
                85                  90                  95

Ile Ser Glu Thr Glu Ile Tyr Asp Leu Glu Ser Ala Gly Gly Pro Met
            100                 105                 110

Ser Trp Gly Gly Gly Ser Gly Met Val Tyr Ala Gly Met Ile Pro Ile
        115                 120                 125

Gly Pro Asn Val Pro Asp Gly Arg Gly Asp Arg Pro Ala Thr Arg Ala
    130                 135                 140

Ala Pro Glu
145


<210> SEQ ID NO 27
<211> LENGTH: 135
<212> TYPE: PRT
<213> ORGANISM: Acidovorax citrulli

<400> SEQUENCE: 27

Met Lys Leu Ser Asn Leu Lys Asn Val Pro Cys Ile Val Trp Cys Leu
1               5                   10                  15

Gly Leu Asn Ala Leu Phe Leu Ala Gly Trp Ala Leu Ala Thr Pro Thr
            20                  25                  30

Phe Ala Asp Ala Glu Asn Ser Pro His Arg Val Tyr Arg Leu Glu Phe
        35                  40                  45

His Lys Ala Ser Phe Leu Gln Arg Ile Thr His Pro Arg Phe Lys Met
    50                  55                  60

Pro Tyr Val Val Arg Leu Tyr Arg Ile Glu Pro Lys Thr Leu Leu Gly
65                  70                  75                  80

Gln Ser Glu Val Val Asp Leu Trp Leu Asn Gly Glu Ile His Trp Tyr
                85                  90                  95

Leu Asp Pro Pro Val Asp Met Asn Arg Val Arg Val Gly Arg Asp Val
            100                 105                 110

Leu Phe Glu Ser Ile Pro Pro Glu Cys Thr Lys Glu Ala Gln Ile Pro
        115                 120                 125

Ser Cys Pro Asn Thr Lys Pro
    130                 135


<210> SEQ ID NO 28
<211> LENGTH: 135
<212> TYPE: PRT
<213> ORGANISM: Acidovorax avenae

<400> SEQUENCE: 28

Met Lys Leu Ser Ala Leu Lys Asn Val Pro Cys Ile Val Trp Cys Leu
1               5                   10                  15

Gly Leu Asn Ala Leu Phe Leu Ala Gly Trp Ala Leu Ala Thr Pro Thr
            20                  25                  30

Phe Val Asp Ala Glu Asn Ser Pro His Arg Val Tyr Arg Leu Glu Phe
        35                  40                  45
```

```
His Lys Ala Ser Phe Leu Gln Arg Ile Ile His Pro Arg Phe Lys Met
    50                  55                  60

Pro Tyr Val Val Arg Leu Tyr Arg Ile Glu Pro Lys Thr Leu Leu Gly
65                  70                  75                  80

Gln Ser Glu Val Val Asp Leu Trp Leu Asn Gly Glu Ile His Trp Tyr
                85                  90                  95

Leu Asp Pro Pro Val Asp Met Asn Arg Val Arg Val Gly Arg Asp Val
            100                 105                 110

Leu Phe Glu Ser Ile Pro Pro Glu Cys Thr Lys Glu Ala Gln Ile Pro
        115                 120                 125

Ser Cys Pro Asn Thr Lys Pro
    130                 135


<210> SEQ ID NO 29
<211> LENGTH: 135
<212> TYPE: PRT
<213> ORGANISM: Acidovorax citrulli

<400> SEQUENCE: 29

Met Lys Leu Ser His Leu Lys Asn Val Pro Cys Ile Val Trp Cys Leu
1               5                   10                  15

Gly Leu Asn Ala Leu Phe Leu Ala Gly Trp Ala Leu Ala Thr Pro Thr
            20                  25                  30

Phe Ala Asp Ala Glu Asn Ser Pro His Arg Val Tyr Arg Leu Glu Phe
        35                  40                  45

His Lys Ala Ser Phe Leu Gln Arg Ile Thr His Pro Arg Phe Lys Met
    50                  55                  60

Pro Tyr Val Val Arg Leu Tyr Arg Ile Glu Pro Lys Thr Leu Leu Gly
65                  70                  75                  80

Gln Ser Glu Val Val Asp Leu Trp Leu Asn Gly Glu Ile Gln Trp Tyr
                85                  90                  95

Leu Asp Pro Pro Val Asp Met Asn Arg Val Arg Val Gly Arg Asp Val
            100                 105                 110

Leu Phe Glu Ser Ile Pro Ser Glu Cys Thr Thr Glu Ala Gln Ile Pro
        115                 120                 125

Gly Cys Pro Ser Thr Lys Pro
    130                 135


<210> SEQ ID NO 30
<211> LENGTH: 135
<212> TYPE: PRT
<213> ORGANISM: Acidovorax citrulli

<400> SEQUENCE: 30

Met Lys Leu Pro Asn Leu Lys Asn Val Pro Cys Ile Val Trp Cys Leu
1               5                   10                  15

Gly Leu Asn Ala Leu Phe Leu Ala Gly Trp Ala Leu Ala Thr Pro Thr
            20                  25                  30

Phe Ala Asp Ala Glu Asn Ser Pro His Arg Val Tyr Arg Leu Glu Phe
        35                  40                  45

His Lys Ala Ser Phe Leu Gln Arg Ile Thr His Pro Ser Phe Lys Met
    50                  55                  60

Pro Tyr Val Val Arg Leu Tyr Arg Ile Glu Pro Lys Thr Leu Leu Gly
65                  70                  75                  80

Gln Ser Glu Val Val Asp Leu Trp Leu Asn Gly Glu Ile His Trp Tyr
                85                  90                  95
```

-continued

```
Leu Asp Pro Pro Val Glu Leu Ser Arg Val Arg Val Gly Gln Asp Val
            100                 105                 110

Ile Phe Glu Asn Ile Pro Arg Glu Cys Thr Lys Glu Ala Gln Ile Pro
        115                 120                 125

Gly Cys Pro Asp Thr Lys Pro
    130                 135


<210> SEQ ID NO 31
<211> LENGTH: 148
<212> TYPE: PRT
<213> ORGANISM: Acidovorax avenae avenae

<400> SEQUENCE: 31

Met Ile Ala Pro Asp Gly Ile Ala Ser His Arg Ser Ala Met Lys Leu
1               5                   10                  15

Ser Asn Leu Lys Asn Val Pro Cys Ile Val Trp Cys Leu Gly Leu Asn
            20                  25                  30

Ala Leu Phe Leu Ala Gly Trp Thr Leu Ala Thr Pro Thr Phe Ala Asp
        35                  40                  45

Ala Glu Asn Ser Pro His Arg Val Tyr Arg Leu Glu Phe His Lys Ala
    50                  55                  60

Ser Phe Leu Gln Arg Ile Thr His Pro Ser Phe Lys Met Pro Tyr Val
65                  70                  75                  80

Val Arg Leu Tyr Arg Ile Glu Pro Lys Thr Leu Leu Gly Gln Ser Glu
                85                  90                  95

Val Val Asp Leu Trp Leu Asn Gly Glu Ile His Trp Tyr Leu Asp Pro
            100                 105                 110

Pro Val Glu Leu Ser Arg Val Arg Val Gly Gln Asp Val Ile Phe Glu
        115                 120                 125

Asn Ile Pro Pro Glu Cys Thr Lys Glu Ala Gln Ile Pro Gly Cys Pro
    130                 135                 140

Ser Thr Lys Pro
145


<210> SEQ ID NO 32
<211> LENGTH: 132
<212> TYPE: PRT
<213> ORGANISM: Acidovorax avenae

<400> SEQUENCE: 32

Met Lys Leu Ser Asn Leu Lys Lys Val Pro Cys Ile Val Trp Cys Leu
1               5                   10                  15

Gly Leu Asn Ala Leu Phe Leu Ala Gly Trp Ser Leu Ala Thr Pro Thr
            20                  25                  30

Phe Ala Asp Ala Glu Asn Ser Pro His Arg Val Tyr Arg Leu Glu Phe
        35                  40                  45

His Lys Ala Ser Phe Leu Gln Arg Ile Thr His Pro Ser Phe Lys Met
    50                  55                  60

Pro Tyr Val Val Arg Leu Tyr Arg Ile Glu Pro Lys Ala Leu Leu Gly
65                  70                  75                  80

Gln Ser Glu Val Val Asp Leu Trp Leu Asn Gly Glu Ile Gln Trp Tyr
                85                  90                  95

Leu Asp Pro Pro Val Glu Leu Asn Arg Val Arg Val Gly Gln Asp Val
            100                 105                 110

Ile Phe Glu Asn Ile Pro Pro Glu Glu Ala Gln Ile Pro Gly Cys Leu
        115                 120                 125
```

Asp Thr Lys Pro
    130

<210> SEQ ID NO 33
<211> LENGTH: 135
<212> TYPE: PRT
<213> ORGANISM: Acidovorax oryzae

<400> SEQUENCE: 33

Met Lys Leu Pro Asp Leu Lys Lys Val Pro Cys Ile Val Trp Cys Leu
1               5                   10                  15

Gly Leu Asn Ala Leu Phe Leu Ala Gly Trp Ala Leu Ala Lys Pro Thr
            20                  25                  30

Phe Ala Asp Ala Glu Asn Ser Pro His Arg Val Tyr Arg Leu Glu Phe
        35                  40                  45

His Lys Ala Ser Phe Leu Gln Arg Ile Thr His Pro Ser Phe Lys Met
    50                  55                  60

Pro Tyr Val Val Arg Leu Tyr Arg Ile Glu Ser Lys Thr Leu Leu Gly
65                  70                  75                  80

Gln Ser Glu Val Val Asp Leu Trp Leu Asn Gly Asp Ile Glu Trp Gln
                85                  90                  95

Leu Asp Ser Pro Val Gln Ala Asn Lys Val Arg Val Gly Arg Asp Val
            100                 105                 110

Ile Phe Arg Asp Ile Pro Ser Glu Cys Ala Ala Ala Thr Gln Ile Pro
        115                 120                 125

Gly Cys Pro Ser Thr Asn Pro
    130                 135

<210> SEQ ID NO 34
<211> LENGTH: 135
<212> TYPE: PRT
<213> ORGANISM: Acidovorax citrulli

<400> SEQUENCE: 34

Met Lys Leu Ser Gly Leu Lys Asn Val Pro Cys Ile Leu Trp Cys Leu
1               5                   10                  15

Ala Leu Asn Ala Cys Val Val Leu Gly Trp Tyr Ala Thr Lys Pro Thr
            20                  25                  30

Leu Phe Asn Ser Tyr Asn Ser Pro Arg Tyr Val Tyr Arg Leu Glu Leu
        35                  40                  45

Tyr His Ala Ser Leu Trp Gln Arg Ile Ile His Tyr Asp Gln Lys Ala
    50                  55                  60

Pro Phe Ile Val Arg Leu His Arg Val Asp Pro Lys Glu Leu Leu Gly
65                  70                  75                  80

Glu Ser Gln Val Val Asp Leu Trp Ser Gly Ile Asp Ile Asp Trp Gln
                85                  90                  95

Leu Asp Pro Leu Val Gln Thr Asn Lys Val Arg Val Gly Arg Asp Val
            100                 105                 110

Ile Phe Arg Asn Ile Pro Pro Glu Cys Thr Glu Ala Ala Gln Leu Gln
        115                 120                 125

Gly Cys Pro Asn Thr Lys Pro
    130                 135

<210> SEQ ID NO 35
<211> LENGTH: 135
<212> TYPE: PRT
<213> ORGANISM: Acidovorax avenae

<400> SEQUENCE: 35

Met Lys Leu Ser Gly Leu Lys Asn Val Pro Cys Ile Val Trp Cys Leu
1 5 10 15

Ala Leu Asn Ala Cys Val Val Leu Gly Trp Tyr Ala Thr Lys Pro Thr
20 25 30

Leu Phe Asn Ser Tyr Asn Ser Pro His Tyr Val Tyr Arg Leu Glu Leu
35 40 45

Tyr His Ala Ser Leu Trp Gln Arg Ile Thr His Tyr Asp Gln Lys Ala
50 55 60

Pro Phe Ile Val Arg Leu His Arg Val Asp Pro Lys Glu Leu Leu Gly
65 70 75 80

Glu Ser Gln Val Val Asp Leu Trp Ser Gly Ile Asp Ile Asp Trp Gln
85 90 95

Leu Asp Pro Pro Val Gln Ala Asn Lys Val Arg Val Gly Arg Asp Val
100 105 110

Ile Phe Lys Asn Ile Pro Ser Glu Cys Thr Glu Ala Ala Gln Ile Pro
115 120 125

Gly Cys Pro Asn Thr Arg Pro
130 135

<210> SEQ ID NO 36
<211> LENGTH: 135
<212> TYPE: PRT
<213> ORGANISM: Acidovorax avenae

<400> SEQUENCE: 36

Met Lys Leu Pro Gly Leu Lys Asn Val Pro Cys Ile Val Trp Cys Leu
1 5 10 15

Ala Leu Asn Ala Cys Val Val Leu Gly Trp Tyr Ala Thr Lys Pro Thr
20 25 30

Leu Phe Asn Ser Tyr Asn Ser Pro His Tyr Val Tyr Arg Leu Glu Leu
35 40 45

Tyr His Ala Ser Leu Trp Gln Arg Ile Leu His Tyr Asp Gln Lys Ala
50 55 60

Pro Phe Ile Val Arg Leu His Arg Val Asp Pro Lys Glu Leu Leu Gly
65 70 75 80

Glu Ser Gln Val Val Asp Leu Trp Ser Gly Ile Asp Ile Asp Trp Gln
85 90 95

Leu Asp Pro Pro Val Gln Ala Asn Lys Val Arg Val Gly Arg Asp Val
100 105 110

Ile Phe Lys Asp Ile Pro Ser Glu Cys Ser Glu Ala Ala Gln Lys Pro
115 120 125

Gly Cys Pro Asn Thr Lys Pro
130 135

<210> SEQ ID NO 37
<211> LENGTH: 135
<212> TYPE: PRT
<213> ORGANISM: Acidovorax oryzae

<400> SEQUENCE: 37

Met Lys Leu Ser Gly Leu Lys Asn Val Pro Cys Ile Leu Trp Cys Leu
1 5 10 15

Ala Leu Asn Ala Cys Val Val Leu Gly Trp Tyr Ala Thr Lys Pro Thr
20 25 30

Leu Phe Asn Ser Tyr Asn Ser Pro His Tyr Val Tyr Arg Leu Glu Phe

```
        35                  40                  45

Tyr His Ala Ser Leu Trp Gln Arg Ile Thr His Tyr Asp Gln Lys Ala
    50                  55                  60

Pro Phe Ile Val Arg Leu His Arg Val Asp Pro Lys Glu Leu Leu Gly
65                  70                  75                  80

Glu Ser Gln Val Val Asp Leu Trp Ser Gly Ile Asp Ile Glu Trp Gln
                85                  90                  95

Leu Asp Pro Pro Val Gln Thr Asn Lys Val Arg Val Gly Arg Asp Val
            100                 105                 110

Ile Phe Arg Asn Ile Pro Pro Glu Cys Thr Glu Ala Ala Gln Leu Pro
        115                 120                 125

Gly Cys Pro Asn Thr Lys Pro
    130                 135


<210> SEQ ID NO 38
<211> LENGTH: 135
<212> TYPE: PRT
<213> ORGANISM: Acidovorax avenae

<400> SEQUENCE: 38

Met Lys Leu Pro Asn Leu Lys Asn Val Pro Cys Leu Val Trp Cys Leu
1               5                   10                  15

Ala Leu Asn Ala Cys Val Val Leu Gly Trp Tyr Ala Thr Thr Pro Thr
            20                  25                  30

Leu Phe Met Thr Tyr Asn Ser Pro His Ser Val Tyr Arg Leu Glu Ile
        35                  40                  45

His Arg Ala Ser Pro Trp Gln Arg Met Val His Arg Asp Gln Glu Ala
    50                  55                  60

Pro Ala Ile Val Arg Leu Tyr Arg Val Asp Pro Lys Glu Leu Leu Gly
65                  70                  75                  80

Glu Ser Lys Val Val Asp Leu Met Asp Gly Ser Glu Val Asp Trp Gln
                85                  90                  95

Leu Asp Pro Pro Val Gln Ala Ser Lys Val Arg Val Gly Pro Gly Val
            100                 105                 110

Val Phe Glu Asn Ile Pro Ser Glu Cys Thr Ala Ala Gly Asp Met Pro
        115                 120                 125

Gly Cys Pro Asn Ala Lys Pro
    130                 135


<210> SEQ ID NO 39
<211> LENGTH: 136
<212> TYPE: PRT
<213> ORGANISM: Acidovorax citrulli

<400> SEQUENCE: 39

Met Met Lys Leu Ser Asn Leu Lys Asn Val Pro Cys Ile Ile Trp Trp
1               5                   10                  15

Leu Ala Asp Ser Ala Cys Leu Gly Leu Val Trp Tyr Val Ile Thr Pro
            20                  25                  30

Thr Leu Phe Met Thr Tyr Asn Ser Pro His Ala Val Tyr Arg Leu Glu
        35                  40                  45

Ile His Arg Ala Ser Pro Trp Gln Arg Ile Val His Arg Asp Gln Glu
    50                  55                  60

Ala Pro Ala Ile Val Arg Leu Tyr Arg Val Asp Pro Lys Glu Leu Leu
65                  70                  75                  80

Gly Glu Ser Lys Val Val Asp Leu Met Asp Gly Ser Gly Val Asp Trp
```

```
                85                  90                  95

Gln Leu Asp Pro Pro Val Gln Ala Asn Lys Val Arg Val Gly Pro Gly
            100                 105                 110

Val Val Phe Glu Asn Ile Pro Ser Glu Cys Thr Ala Ala Gly Asp Ile
        115                 120                 125

Pro Gly Cys Pro Asn Thr Lys Pro
    130                 135


<210> SEQ ID NO 40
<211> LENGTH: 143
<212> TYPE: PRT
<213> ORGANISM: Pseudomonas syringae

<400> SEQUENCE: 40

Met Lys Ser Pro Ser Thr Cys Thr Ala Cys Leu Ala Ala Tyr Ile Ala
1               5                   10                  15

Ile Ala Phe Ser Leu Trp Thr Ala Ser Gln Trp Trp Glu Lys Gly Leu
            20                  25                  30

Ala Glu Arg Ser Gly Ala Pro Ile Val Ser Pro Asp Gly Cys Tyr Arg
        35                  40                  45

Leu Glu Thr Phe Lys Pro Phe Trp Val Leu Pro Asn Met Leu His Arg
    50                  55                  60

Lys Pro His Pro Asp Glu Asp Val Pro Pro Lys Trp Phe Pro Leu Trp
65                  70                  75                  80

Gly Tyr Arg Gly Phe Tyr Arg Leu Tyr Asp Asn Arg Asn Gly Glu Leu
                85                  90                  95

Ile Ser Glu Asn Lys Ile Tyr Asp Leu Glu Thr Ala Gly Trp Gly Ile
            100                 105                 110

Asp Trp Gly Glu Gly Ser Gly Phe Val Tyr Ala Gly Met Ile Leu Ile
        115                 120                 125

Gly Pro Asn Val Ser Asp Gly Val Gly Asp Gln Pro Ala Ile Pro
    130                 135                 140


<210> SEQ ID NO 41
<211> LENGTH: 143
<212> TYPE: PRT
<213> ORGANISM: Pseudomonas syringae

<400> SEQUENCE: 41

Met Lys Ser Pro Ser Thr Cys Thr Ala Cys Leu Ala Ala Tyr Ile Ala
1               5                   10                  15

Ile Ala Phe Ser Leu Trp Thr Ala Ser Gln Trp Trp Glu Lys Gly Leu
            20                  25                  30

Ala Glu Arg Ser Gly Ala Pro Ile Val Ser Pro Asp Gly Cys Tyr Arg
        35                  40                  45

Leu Glu Thr Phe Lys Pro Phe Trp Val Leu Pro Asn Met Leu His Arg
    50                  55                  60

Lys Pro His Pro Asp Glu Asp Val Pro Pro Lys Trp Phe Pro Leu Trp
65                  70                  75                  80

Gly Tyr Arg Gly Phe Tyr Arg Leu Tyr Asp Asn Arg Asn Gly Glu Leu
                85                  90                  95

Ile Ser Glu Asn Lys Ile Tyr Asp Leu Glu Thr Ala Gly Trp Gly Ile
            100                 105                 110

Asp Trp Gly Glu Gly Ser Gly Phe Val Tyr Ala Gly Met Ile Leu Ile
        115                 120                 125

Gly Pro Asn Val Ser Asp Gly Val Gly Asp Gln Pro Ala Ile Pro
```

130 135 140

<210> SEQ ID NO 42
<211> LENGTH: 147
<212> TYPE: PRT
<213> ORGANISM: Pseudomonas syringae

<400> SEQUENCE: 42

Leu Lys Ile Ser Ala Arg Lys Ile Gln Phe Leu Ser Ala Tyr Phe Leu
1 5 10 15

Ile Ala Leu Ser Leu Trp Ala Ala Ser Gln Trp Trp Glu Lys Gly Leu
20 25 30

Ala Glu Arg Ser Gly Asp Pro Ile Val Ser Pro Asp Gly Cys Tyr Arg
35 40 45

Leu Glu Thr Phe Lys Pro Phe Trp Val Leu Pro Asn Met Phe His Arg
50 55 60

Lys Pro His Pro Asp Glu Asp Val Pro Pro Lys Trp Phe Pro Leu Trp
65 70 75 80

Gly Tyr Arg Gly Phe Tyr Arg Leu Tyr Asp Asn Arg Asn Gly Glu Leu
85 90 95

Ile Ser Glu Asn Lys Ile Tyr Asp Leu Glu Thr Ala Gly Trp Gly Ile
100 105 110

Asp Trp Gly Glu Glu Ser Gly Phe Val Tyr Ala Gly Met Ile Leu Ile
115 120 125

Gly Pro Asn Val Ser Asp Gly Ile Gly Asp Arg Ser Ser His Val Thr
130 135 140

Asn Gln Lys
145

<210> SEQ ID NO 43
<211> LENGTH: 147
<212> TYPE: PRT
<213> ORGANISM: Pseudomonas syringae

<400> SEQUENCE: 43

Met Lys Ile Ser Ala Arg Lys Ile Gln Phe Leu Ser Ala Tyr Phe Leu
1 5 10 15

Ile Ala Leu Ser Leu Trp Ala Ala Ser Gln Trp Trp Glu Lys Gly Leu
20 25 30

Ala Glu Arg Ser Gly Asp Pro Ile Val Ser Pro Asp Gly Cys Tyr Arg
35 40 45

Leu Glu Thr Phe Lys Pro Phe Trp Val Leu Pro Asn Met Phe His Arg
50 55 60

Lys Pro His Pro Asp Glu Asp Val Pro Pro Lys Trp Phe Pro Leu Trp
65 70 75 80

Gly Tyr Arg Gly Phe Tyr Arg Leu Tyr Asp Asn Arg Asn Gly Glu Leu
85 90 95

Ile Ser Glu Asn Lys Ile Tyr Asp Leu Glu Thr Ala Gly Trp Gly Ile
100 105 110

Asp Trp Gly Glu Glu Ser Gly Phe Val Tyr Ala Gly Met Ile Leu Ile
115 120 125

Gly Pro Asn Val Ser Asp Gly Ile Gly Asp Arg Ser Ser His Val Thr
130 135 140

Asn Gln Lys
145

<210> SEQ ID NO 44
<211> LENGTH: 89
<212> TYPE: PRT
<213> ORGANISM: Pseudomonas syringae

<400> SEQUENCE: 44

Met Met Phe His Thr Met Pro Asp Pro Asn Glu Gly Val Pro Leu Glu
1               5                   10                  15

Trp Leu Pro Trp Trp Gly Tyr Arg Ala Phe Phe Arg Leu Tyr Asp His
            20                  25                  30

His Thr Gly Glu Leu Ile Ser Glu Thr Glu Ile Tyr Asp Leu Glu Ser
        35                  40                  45

Ala Gly Gly Pro Met Ser Trp Gly Gly Gly Ser Gly Met Ile Tyr Ala
    50                  55                  60

Gly Met Ile Pro Ile Gly Pro Asn Val Ser Asp Gly Met Gly Asp Arg
65                  70                  75                  80

Pro Thr Thr Arg Ala Thr Pro Gln Lys
                85

<210> SEQ ID NO 45
<211> LENGTH: 143
<212> TYPE: PRT
<213> ORGANISM: Pseudomonas syringae

<400> SEQUENCE: 45

Met Lys Ser Pro Ser Lys Arg Ile Ile Phe Leu Ala Ala Tyr Ile Thr
1               5                   10                  15

Ile Ala Gly Ser Ile Trp Ala Ala Ser Glu Trp Trp Glu Ile Gly Leu
            20                  25                  30

Ala Glu Arg Leu Ser Asp Pro Tyr Ile Ser Pro Gly Gly Cys Tyr Arg
        35                  40                  45

Val Glu Leu Phe Lys Pro Phe Trp Val Leu Pro Met Met Phe His Thr
    50                  55                  60

Met Pro Asp Pro Asn Glu Gly Val Pro Arg Glu Trp Leu Pro Trp Trp
65                  70                  75                  80

Gly Tyr Arg Ala Phe Phe Arg Leu Tyr Asp His Arg Thr Gly Glu Leu
                85                  90                  95

Ile Ser Glu Thr Glu Ile His Asp Leu Glu Ser Ala Gly Gly Pro Met
            100                 105                 110

Ser Trp Gly Gly Gly Ser Gly Met Val Tyr Ala Gly Met Ile Pro Ile
        115                 120                 125

Gly Pro Asn Val Pro Asp Gly Ile Gly Asp Gln Pro Ala Thr His
    130                 135                 140

<210> SEQ ID NO 46
<211> LENGTH: 143
<212> TYPE: PRT
<213> ORGANISM: Pseudomonas syringae

<400> SEQUENCE: 46

Met Lys Ser Pro Ser Lys Arg Ile Ile Phe Leu Ala Ala Tyr Ile Thr
1               5                   10                  15

Ile Ala Gly Ser Ile Trp Ala Ala Ser Glu Trp Trp Glu Ile Gly Leu
            20                  25                  30

Ala Glu Arg Leu Ser Asp Pro Tyr Ile Ser Pro Gly Gly Cys Tyr Arg
        35                  40                  45

Val Glu Leu Phe Lys Pro Phe Trp Val Leu Pro Met Met Phe His Thr
    50                  55                  60

```
Met Pro Asp Pro Asn Glu Gly Val Pro Arg Glu Trp Leu Pro Trp Trp
65                  70                  75                  80

Gly Tyr Arg Ala Phe Phe Arg Leu Tyr Asp His Arg Thr Gly Glu Leu
                85                  90                  95

Ile Ser Glu Thr Glu Ile His Asp Leu Glu Ser Ala Gly Gly Pro Met
            100                 105                 110

Ser Trp Gly Gly Gly Ser Gly Met Val Tyr Ala Gly Met Ile Pro Ile
        115                 120                 125

Gly Pro Asn Ala Pro Asp Gly Ile Gly Asp Gln Pro Ala Thr His
    130                 135                 140


<210> SEQ ID NO 47
<211> LENGTH: 308
<212> TYPE: PRT
<213> ORGANISM: Pseudomonas syringae

<400> SEQUENCE: 47

Met Ser Leu Asn Asp Phe Gln Arg Thr Asn Ala Val Gly Pro Asp Thr
1               5                   10                  15

Tyr Phe Ala Leu Pro Gln Gly Val Ser Arg Thr Tyr Ala Pro Leu Asp
            20                  25                  30

Thr Pro Pro Lys Gln Val Ile Ile Glu Asn Leu Ala Leu Ser Arg Ile
        35                  40                  45

Pro Gly Ala Met Arg Asn Met Gly Trp Asp Thr Ala Ala Ala Leu Leu
    50                  55                  60

Gln Arg Trp Phe Asp Ser Pro Gly Trp Glu Met Pro Ala Asp Trp Lys
65                  70                  75                  80

Lys Pro Glu Thr Gln Pro Asp Pro Met Ser Leu Ser Pro Glu Gln Cys
                85                  90                  95

Asp Glu Asp Ile Val Lys Met Glu Trp Ala Met Gln Phe Glu Arg Cys
            100                 105                 110

Arg Thr Ala Ile Ala Val Ala Glu Ser Arg Leu Thr Thr Pro Asn Ala
        115                 120                 125

Leu Leu Arg Leu Lys Lys Leu Leu Lys Lys Gln Gly Trp His Gly Ser
    130                 135                 140

Ala Pro Phe Lys Leu Gly Ser Thr Leu Met Thr Ala Arg Gln Ile Asp
145                 150                 155                 160

Val Ser Ser Gln Val Asn Phe Thr Glu Phe Gly Gly Ala Trp Asp Ala
                165                 170                 175

Leu Asp Asp Met Tyr Gly Ala Leu Gly Thr Ala Thr Leu Lys Val Gly
            180                 185                 190

Val Val Gly Glu Val Phe Thr Lys Glu His Pro Ile Thr Gln Gln Ala
        195                 200                 205

Gln His Tyr Phe Arg Val Glu Met Leu Gly Phe Tyr Ile Arg Asp His
    210                 215                 220

Tyr Asp Phe Asn Gly Phe Gln Tyr Leu Gly Thr Trp Thr Glu Asp Arg
225                 230                 235                 240

Val Leu Thr Lys Ala Glu Thr Val Ile Ala Val Ile Pro Gln Gly Asn
                245                 250                 255

Leu Ile Ile Arg Leu Lys Glu Gly Pro Phe Ala Ala Ile Ala Asn Asn
            260                 265                 270

Met Phe Arg Lys Tyr Arg Asp Asn Thr Ser Asn Gly Gly Asp Phe Phe
        275                 280                 285

Ile Tyr Ser Asp Val Leu Trp Lys Lys Ala Asp Pro Phe Ile Asp Leu
```

```
    290                 295                 300

Glu Ile Pro Thr
305


<210> SEQ ID NO 48
<211> LENGTH: 497
<212> TYPE: PRT
<213> ORGANISM: Pseudomonas aeruginosa

<400> SEQUENCE: 48

Met Pro Leu Arg Leu Thr Ile Thr Ser Tyr Met Lys Leu Thr Pro Gly
1               5                   10                  15

Gln Cys Ser Glu Lys Val Leu Asp Gln Gly Gln Leu Thr Ile Gly Arg
            20                  25                  30

Gly Pro Asp Asn Asp Trp Val Leu Pro Asp Pro Glu Arg Leu Val Ser
        35                  40                  45

Ser Arg Met Cys Thr Ile Leu Asn Arg Asp Gly Val Tyr Tyr Leu Thr
    50                  55                  60

Asp Thr Ser Thr Asn Gly Val Leu Leu Val Asn Ala Gly Met Arg Leu
65                  70                  75                  80

Arg Arg Gly Asn Ser Glu Pro Leu Gln Asp Gly Glu Thr Val Arg Leu
                85                  90                  95

Gly Glu Tyr Asp Ile Leu Val Gln Leu Gly His Asp Ile Ala Leu Pro
            100                 105                 110

Gly Ser Gly Asn Pro Gln Thr Asp Pro Phe Thr Ser Phe Asp Ala Leu
        115                 120                 125

Met Ser Arg Gln Ala Ala Gly Ser Ala Pro Ala Phe Ala Glu Pro Ala
    130                 135                 140

Pro Thr Pro Met Pro Ala Val Thr Ala His Phe Gln Gly Gly Ser Pro
145                 150                 155                 160

Leu Asp Thr Lys Pro Asp Leu Phe Asp Phe Leu Thr Pro Pro Pro Pro
                165                 170                 175

Gly Ala Ala Pro Arg Pro Asp His Val Pro Ala Glu Gln His Asp Phe
            180                 185                 190

Arg Pro Pro Glu Pro Val Ile Pro Pro Pro Pro Ala Thr Thr Pro Ala
        195                 200                 205

Pro Pro Pro Ala Gly Gly Ala Pro Leu Ile Pro Ala Asp Trp Asp Pro
    210                 215                 220

Phe Ala Glu Leu Leu Gly Asn Thr Pro Ala Pro Ser Ala Thr Pro Val
225                 230                 235                 240

Ala Gln Pro Leu Pro Thr Ala Glu Pro Thr Pro Leu Ala Met Pro Phe
                245                 250                 255

Ala Asp Pro Gly Ile Thr Gln Gln Pro Gln Pro Gln Pro Gln Pro Gln
            260                 265                 270

Pro Gln Pro Gln Pro Gln Pro Gln Pro Gln Pro Gln Pro Ala Ser Val
        275                 280                 285

Ala Ala Pro Thr Pro Pro Ala Ser Ala Ala Ala Ser Ala Gly Gly Asp
    290                 295                 300

Leu Leu Gln Ala Phe Leu Arg Gly Ala Gly Met Thr Gln Leu Lys Val
305                 310                 315                 320

Asp Pro Ala Gly Ala Glu Ala Gln Met Glu Ala Ile Gly Arg Ser Tyr
                325                 330                 335

Arg Gly Leu Val Glu Gly Leu Val Asp Val Leu Arg Ala Arg Ala Ser
            340                 345                 350
```

-continued

```
Leu Lys Gly Glu Phe Arg Met Ala Gln Thr Met Ile Gln Pro Val Gln
        355                 360                 365

Asn Asn Pro Leu Lys Phe Ala Pro Asn Val Asp Glu Ala Met Leu Leu
    370                 375                 380

Leu Leu Arg Arg Asp Asn Gln Ala Phe Met Ala Pro Asp Arg Ala Val
385                 390                 395                 400

Ala Asp Ser Phe Glu Asp Leu Lys Ala His Gln Leu Ala Val Met Ala
                405                 410                 415

Gly Val Gln Ala Ala Ile Arg His Leu Leu Ala Arg Phe Glu Pro Ala
            420                 425                 430

Ala Leu Glu Ala Arg Phe Gly Lys Pro Ala Gly Leu Ser Gly Leu Leu
        435                 440                 445

Pro Gly Ala Arg Gln Ala Gln Asn Trp Asp Ser Phe Thr Glu Leu Tyr
    450                 455                 460

Ala Lys Ile Leu Arg Glu Ala Glu Asp Asp Phe Gln Glu Leu Phe Gly
465                 470                 475                 480

Arg Glu Phe Ser Arg Ala Tyr Glu Glu His Ser Ala Arg Leu Arg Arg
                485                 490                 495

Ser
```